United States Patent
Tokoyoda et al.

(10) Patent No.: US 11,261,220 B2
(45) Date of Patent: Mar. 1, 2022

(54) *SALMONELLA SIIE*-DERIVED PEPTIDES FOR MANIPULATION OF LONG-LIVED PLASMA CELLS

(71) Applicant: DEUTSCHES RHEUMA-FORSCHUNGSZENTRUM BERLIN, Berlin (DE)

(72) Inventors: Koji Tokoyoda, Berlin (DE); Akiko Takaya, Chiba (JP)

(73) Assignee: DEUTSCHES RHEUMA-FORSCHUNG-SZENTRUM BERLIN, Berlin (DE)

( * ) Notice: Subject to any disclaimer, the term of this patent is extended or adjusted under 35 U.S.C. 154(b) by 0 days.

(21) Appl. No.: 16/644,852

(22) PCT Filed: Sep. 6, 2018

(86) PCT No.: PCT/EP2018/073992
§ 371 (c)(1),
(2) Date: Mar. 5, 2020

(87) PCT Pub. No.: WO2019/048540
PCT Pub. Date: Mar. 14, 2019

(65) Prior Publication Data
US 2021/0070813 A1    Mar. 11, 2021

(30) Foreign Application Priority Data

Sep. 8, 2017   (EP) .................................... 17190133
Nov. 1, 2017   (EP) .................................... 17199568

(51) Int. Cl.
*C07K 14/255*   (2006.01)
*A61P 37/06*    (2006.01)
*A61K 38/00*    (2006.01)
*A61K 39/00*    (2006.01)

(52) U.S. Cl.
CPC ............ *C07K 14/255* (2013.01); *A61K 38/00* (2013.01); *A61K 39/00* (2013.01); *A61P 37/06* (2018.01)

(58) Field of Classification Search
None
See application file for complete search history.

(56) References Cited

U.S. PATENT DOCUMENTS 8,771,669 B1   7/2014   Bermudes

FOREIGN PATENT DOCUMENTS

WO    WO 02/077183 A2    10/2002

OTHER PUBLICATIONS

Devos et al. (Proteins: Structure, Function and Genetics, 2000, vol. 41: 98-107 (Year: 2000).*
Whisstock et al., (Quarterly Reviews of Biophysics 2003, vol. 36 (3): 307-340 )) (Year: 2003).*
Houghten et al. (Vaccines, 1986, Edited by Fred Brown: Cold Spring Harbor Laboratory) (Year: 1986).*
International Search Report and Written Opinion, PCT/EP2018/073992, dated Oct. 8, 2018.
Morgan, Eirwen, et al., 2007 "SiiE is Secreted by the *Salmonella enterica* Serovar Typhimurium Pathogenicity Island 4-Encoded Secretion System and Conributes to Intestinal Colonization in Cattle", Infection and Immunity, 75(3): 1524-1533.

* cited by examiner

*Primary Examiner* — Padmavathi Baskar
(74) *Attorney, Agent, or Firm* — Knobbe, Martens, Olson & Bear, LLP

(57) ABSTRACT

An isolated polypeptide includes the amino acid sequence EEAEKAKEAAEKALNEAFE or an amino acid sequence with a sequence identity of least 70%, 80%, or 90% identity to that sequence. The polypeptide is no longer than 200 or 170 amino acids. A nucleic acid encodes the polypeptide, a gene therapy vector includes the nucleic acid and genetically modified cells express the polypeptide. The polypeptide, the nucleic acid, the gene therapy vector and/or the cell can be used for the treatment of a disease associated with pathogenic long-lived plasma cells.

15 Claims, 11 Drawing Sheets

Specification includes a Sequence Listing.

NZB/W F1 female: Murine Models of Systemic Lupus Erythematosus

SEQUENCE LISTING

<160> NUMBER OF SEQ ID NOS: 27

<210> SEQ ID NO 1
<211> LENGTH: 19
<212> TYPE: PRT
<213> ORGANISM: Salmonella enterica

<400> SEQUENCE: 1

Glu Glu Ala Glu Lys Ala Lys Glu Ala Ala Glu Lys Ala Leu Asn Glu

```
1               5                   10                  15

Ala Phe Glu

<210> SEQ ID NO 2
<211> LENGTH: 40
<212> TYPE: PRT
<213> ORGANISM: Salmonella enterica

<400> SEQUENCE: 2

Lys Glu Ala Asp Lys Ala Lys Glu Glu Ala Lys Ala Lys Glu Ala
1               5                   10                  15

Ala Glu Lys Ala Leu Asn Glu Ala Phe Glu Val Gln Asn Ser Ser Lys
        20                  25                  30

Gln Ile Glu Glu Met Leu Gln Asn
        35                  40

<210> SEQ ID NO 3
<211> LENGTH: 74
<212> TYPE: PRT
<213> ORGANISM: Salmonella enterica

<400> SEQUENCE: 3

Ser Ala Gln Val Glu Lys Lys Gly Asn Gly Lys Arg Arg Asn Lys Lys
1               5                   10                  15

Glu Glu Glu Glu Leu Lys Lys Gln Leu Asp Asp Ala Glu Asn Ala Lys
        20                  25                  30

Lys Glu Ala Asp Lys Ala Lys Glu Glu Ala Lys Ala Lys Glu Ala
        35                  40                  45

Ala Glu Lys Ala Leu Asn Glu Ala Phe Glu Val Gln Asn Ser Ser Lys
        50                  55                  60

Gln Ile Glu Glu Met Leu Gln Asn Phe Leu
65                  70

<210> SEQ ID NO 4
<211> LENGTH: 170
<212> TYPE: PRT
<213> ORGANISM: Salmonella enterica

<400> SEQUENCE: 4

Met Gly Asn Lys Ser Ile Gln Lys Phe Phe Ala Asp Gln Asn Ser Val
1               5                   10                  15

Ile Asp Leu Ser Ser Leu Gly Asn Ala Lys Gly Ala Lys Val Ser Leu
        20                  25                  30

Ser Gly Pro Asp Met Asn Ile Thr Thr Pro Arg Gly Ser Val Ile Ile
        35                  40                  45

Val Asn Gly Ala Leu Tyr Ser Ser Ile Lys Gly Asn Asn Leu Ala Val
        50                  55                  60

Lys Phe Lys Asp Lys Thr Ile Thr Gly Ala Lys Ile Leu Gly Ser Val
65                  70                  75                  80

Asp Leu Lys Asp Ile Gln Leu Glu Arg Ile Asp Ser Ser Leu Val Asp
                85                  90                  95

Ser Ala Gln Val Glu Lys Lys Gly Asn Gly Lys Arg Arg Asn Lys Lys
                100                 105                 110

Glu Glu Glu Glu Leu Lys Lys Gln Leu Asp Asp Ala Glu Asn Ala Lys
            115                 120                 125

Lys Glu Ala Asp Lys Ala Lys Glu Glu Ala Lys Ala Lys Glu Ala
        130                 135                 140
```

-continued

```
Ala Glu Lys Ala Leu Asn Glu Ala Phe Glu Val Gln Asn Ser Ser Lys
145                 150                 155                 160

Gln Ile Glu Glu Met Leu Gln Asn Phe Leu
                165                 170

<210> SEQ ID NO 5
<211> LENGTH: 5559
<212> TYPE: PRT
<213> ORGANISM: Salmonella enterica

<400> SEQUENCE: 5

Met Gly Asn Lys Ser Ile Gln Lys Phe Phe Ala Asp Gln Asn Ser Val
1               5                   10                  15

Ile Asp Leu Ser Ser Leu Gly Asn Ala Lys Gly Ala Lys Val Ser Leu
            20                  25                  30

Ser Gly Pro Asp Met Asn Ile Thr Thr Pro Arg Gly Ser Val Ile Ile
        35                  40                  45

Val Asn Gly Ala Leu Tyr Ser Ser Ile Lys Gly Asn Asn Leu Ala Val
    50                  55                  60

Lys Phe Lys Asp Lys Thr Ile Thr Gly Ala Lys Ile Leu Gly Ser Val
65              70                  75                  80

Asp Leu Lys Asp Ile Gln Leu Glu Arg Ile Asp Ser Ser Leu Val Asp
                85                  90                  95

Ser Ala Gln Val Glu Lys Lys Gly Asn Gly Lys Arg Arg Asn Lys Lys
            100                 105                 110

Glu Glu Glu Glu Leu Lys Lys Gln Leu Asp Asp Ala Glu Asn Ala Lys
        115                 120                 125

Lys Glu Ala Asp Lys Ala Lys Glu Glu Ala Glu Lys Ala Lys Glu Ala
    130                 135                 140

Ala Glu Lys Ala Leu Asn Glu Ala Phe Glu Val Gln Asn Ser Ser Lys
145                 150                 155                 160

Gln Ile Glu Glu Met Leu Gln Asn Phe Leu Ala Asp Asn Val Ala Lys
                165                 170                 175

Asp Asn Leu Ala Gln Gln Ser Asp Ala Ser Gln Gln Asn Thr Gln Ala
            180                 185                 190

Lys Ala Thr Gln Ala Ser Lys Gln Asn Asp Ala Glu Lys Val Leu Pro
        195                 200                 205

Gln Pro Ile Asn Lys Asn Thr Ser Thr Gly Lys Ser Asn Ser Ser Lys
    210                 215                 220

Asn Glu Glu Asn Lys Leu Asp Ala Glu Ser Val Lys Glu Pro Leu Lys
225                 230                 235                 240

Val Thr Leu Ala Leu Ala Ala Glu Ser Asn Ser Gly Ser Lys Asp Asp
                245                 250                 255

Ser Ile Thr Asn Phe Thr Lys Pro Gln Phe Val Gly Ser Thr Ala Pro
            260                 265                 270

Asn Ala Thr Val Ile Ile Lys Ile Asn Gly Ile Ala Val Gly Gln Ala
        275                 280                 285

Val Ala Asp Ser Leu Gly Asn Phe Thr Phe Thr Ala Pro Glu Thr Leu
    290                 295                 300

Thr Asp Gly Thr Tyr Asn Leu Glu Ala Glu Ala Lys Thr Ala Asp Gly
305                 310                 315                 320

Ser Gly Ser Ala Lys Leu Val Ile Thr Ile Asp Ser Val Thr Asp Lys
                325                 330                 335

Pro Thr Phe Glu Leu Ser Pro Glu Ser Ser Val Ser Gly His Lys Gly
            340                 345                 350
```

```
Leu Thr Pro Thr Leu Thr Pro Ser Ile Val Gly Thr Ala Glu Glu Asn
            355                 360                 365

Ala Lys Val Asp Ile Tyr Val Asp Asn Lys Leu Val Ala Ser Val Asp
        370                 375                 380

Val Asp Lys Asp Gly Asn Trp Ser Tyr Glu Phe Lys Asp Asn Glu Leu
385                 390                 395                 400

Ser Glu Gly Glu Asn Ser Ile Lys Val Ala Val Asp Lys Ala Gly
                405                 410                 415

Asn Lys Asn Glu Thr Thr Asp Ser Ile Ile Thr Asp Thr Ile Ala Pro
                420                 425                 430

Glu Lys Pro Thr Ile Glu Leu Asp Asp Ser Ser Asp Ser Gly Ile Lys
            435                 440                 445

Asn Asp Asn Ile Thr Asn Ser Thr Leu Pro Thr Phe Ile Gly Val Ala
            450                 455                 460

Glu Pro Gly Ser Thr Val Ser Ile Tyr Leu Gly Leu Lys His Leu Gly
465                 470                 475                 480

Glu Val Ile Val Ala Lys Asp Gly Thr Trp Ser Tyr Thr Leu Thr Thr
                485                 490                 495

Pro Leu Lys Asp Gly Glu Tyr Asn Ile Thr Ala Thr Ala Thr Asp Ile
            500                 505                 510

Ala Gly His Thr Ser Ala Thr Ala Asn Leu Pro Phe Thr Ile Asp Thr
            515                 520                 525

Arg Ile Ser Tyr Phe Ser Ala Glu Ile Glu Thr Thr Asn Asp Ser Gly
            530                 535                 540

Ile Val Gly Asp Asn Val Thr Asn Asn Thr Arg Pro Thr Phe Thr Gly
545                 550                 555                 560

Lys Thr Glu Pro Asn Ala Ile Ile Ser Val Ile Asn Ser Glu Thr Gly
                565                 570                 575

Glu Glu Val Ile Phe Lys Ala Asn Asp Lys Gly Glu Trp Thr Phe Asn
                580                 585                 590

Phe Thr Ser Asp Ser Val Glu Gly Ile Asn Asn Leu Thr Phe Thr Val
            595                 600                 605

Glu Asp Val Ala Gly Asn Lys Lys Asp Phe Ser Phe Ser Tyr Val Ile
            610                 615                 620

Asp Thr Ile Ala Pro Val Pro Pro Thr Val Ser Leu Glu Asp Tyr Val
625                 630                 635                 640

Val Leu Pro Asn Gly Ile Ile Leu Ser Gly Asn Asp Leu Pro Ala Leu
                645                 650                 655

Val Gly Thr Ala Glu Pro Lys Ser Thr Ile Leu Leu Met Arg Asp Gly
                660                 665                 670

Lys Leu Tyr Asp Ser Ile Glu Val Asp Ser Asn Gly Thr Trp Asn Tyr
            675                 680                 685

Gln Phe Ser Asn Lys Phe Leu Gln Gly Ala Tyr Asp Ile Glu Ile
            690                 695                 700

Ser Gln Asp Ala Ala Gly Asn Lys Ser Ser Thr Val Lys Tyr Ser Phe
705                 710                 715                 720

Thr Ile Gln Thr Glu Val Val Pro Pro Lys Ala Glu Leu Asp Ala Ser
                725                 730                 735

Asp Asp Ser Gly Ala Lys Gly Asp Trp Ile Thr Asn Lys His Asn Ala
                740                 745                 750

Leu Thr Leu Leu Gly Thr Ala Asp Arg Phe Ala Thr Val Asn Ile Leu
            755                 760                 765
```

```
Ile Asp Gly Lys Thr Ile Gly Val Thr Thr Ala Asp Ala Asp Gly Asn
770                 775                 780

Trp Asn Phe Asp Ile Ser Arg Asn Leu Ser Asp Asn Val Tyr Lys Ile
785                 790                 795                 800

Thr Val Glu Ser Ile Asp Pro Leu Gly Arg Thr Ser Ser Val Asp Tyr
            805                 810                 815

Gln Leu Thr Ile Asp Ser Phe Thr Pro Ile Pro Thr Val Met Leu His
                820                 825                 830

Asp Ser Ala Asp Ser Gly Val Lys Gly Asp Met Ile Thr Lys Ile Asn
            835                 840                 845

Thr Pro Leu Phe Thr Gly Met Ala Glu Ala Asn Ala Lys Val Ser Ile
850                 855                 860

Tyr Val Asp Gly Val Leu Ser Gly Glu Ala Ile Ala Gly Asp Asp Gly
865                 870                 875                 880

Val Trp Asn Phe Gln Phe Thr Thr Ala Leu Ser Asp Gly Ser His Asp
                885                 890                 895

Val Thr Val Lys Val Glu Asp Ile Ala Gly Asn Thr Ala Ser Ser Ser
            900                 905                 910

Ala Tyr Asn Phe Gln Ile Val Thr Gln Thr Gln Lys Pro Thr Ile Glu
            915                 920                 925

Leu Val Asn Asp Thr Gly Val Asp Asn Thr Asp His Ile Ile Asn Glu
930                 935                 940

Lys Asn Pro Ala Leu Thr Gly Thr Ala Ala Pro Tyr Ser Thr Val Lys
945                 950                 955                 960

Leu Tyr Ile Asp Gly Ala Leu Ile Ala Glu Val Arg Thr Asn Lys Asp
                965                 970                 975

Gly Arg Trp Glu Tyr Thr Leu Lys Ala Asp Gln Gly Leu Val Asp Gly
            980                 985                 990

Asp His Arg Ile Thr Ala Ser Val Glu Asp Ile Ala Gly Asn Ile Ala
            995                 1000                1005

His Ser Asp Pro Phe Leu Ile Ser Val Asp Thr Ala Ile Ser Ile Pro
    1010                1015                1020

Ile Val Ser Leu Ser Pro Asp Ser Asp Ser Gly Ile Ser Asp Asp Asn
1025                1030                1035                1040

Leu Thr Asn Ile Val Lys Pro Thr Leu His Leu Lys Asp Ile Asp Pro
                1045                1050                1055

Asp Ile Ile Ser Val Gln Val Trp Asp Ala Met Ser Asp Thr Gln Ile
            1060                1065                1070

Gly Val Ala Thr Gln Gln Pro Asp Gly Ser Trp Ala Tyr Thr Phe Thr
            1075                1080                1085

Ser Asp Leu Thr Glu Gly Leu His Gln Val Tyr Val Lys Val Glu Asp
    1090                1095                1100

Ile Ala Gly Asn Lys Ala Asn Ser Ala Ile Phe Asp Phe Thr Ile Asp
1105                1110                1115                1120

Thr Thr Val Ser Thr Pro Val Ile Ser Leu Leu Ser Lys Asp Asp Thr
                1125                1130                1135

Gly Val Thr Gly Asp Asn Leu Thr Asn Ile Asn Lys Pro Gly Phe Ala
            1140                1145                1150

Ile Ser Gly Val Asp Ala Asp Ala His Arg Val Val Gln Val Met
            1155                1160                1165

His Asn Gly Val Ser Glu Glu Ile Glu Leu Ser His Leu Asn Gly Ser
1170                1175                1180

Trp Leu Phe Ile Pro Gly Asn Thr Trp Ala Asp Gly Ser Tyr Thr Leu
```

-continued

```
             1185                1190                1195                1200
         Thr Val Lys Val Glu Asp Lys Ala Gly Asn Thr Asn Tyr Ser Ala Pro
                     1205                1210                1215
         Leu Thr Val Val Ile Asp Thr Gln Ile Ala Ile Asp Gly Val Glu Leu
                     1220                1225                1230
         Val Asn Asp Ser Gly Val Lys Gly Asp Asn Met Thr Asn Asp Asp Arg
                     1235                1240                1245
         Pro His Phe Arg Val Thr Val Pro Thr Asp Val Asn Glu Val Arg Leu
                     1250                1255                1260
         Ser Ile Asp Gly Gly Asn Ser Trp Val Gln Ala Thr Pro Gly Val Ala
         1265                1270                1275                1280
         Gly Ser Trp Glu Tyr Ile Trp Pro Thr Asp Leu Ala Asp Gly Gln Tyr
                     1285                1290                1295
         Thr Leu Thr Val Glu Ala Thr Asp Lys Ala Gly Asn Thr Val Thr Lys
                     1300                1305                1310
         Thr Ile Asp Phe Ala Val Asp Thr Thr Leu Ser Val Pro Val Ile Val
                     1315                1320                1325
         Leu Asp Ser Ala Asp Asp Thr Gly Ile Gln Gly Asp Asn Met Thr Asn
                     1330                1335                1340
         Ser Thr Gln Pro Thr Phe Ala Leu Gln His Ile Asp Asp Ala Val
         1345                1350                1355                1360
         Arg Val Thr Val Ser Val Glu His Gly Gly Val Thr Thr Thr Phe Asp
                     1365                1370                1375
         Ala Thr Lys Gly Thr Gly Gly Trp Thr Phe Thr Pro Pro Thr Ser Trp
                     1380                1385                1390
         Ala Asp Gly Asp Tyr Thr Leu Ser Val Ser Val Glu Asp Lys Ala Gly
                     1395                1400                1405
         Asn Thr Ser His Ser Ala Ser Leu Thr Val Thr Val Thr Gln Ile
                     1410                1415                1420
         Ala Ile Asn Asn Ile Glu Leu Val Asn Asp Ser Gly Ile Pro Asp Asp
         1425                1430                1435                1440
         Asn Leu Thr Asn Asn Val Arg Pro His Phe Gln Val Thr Val Pro Thr
                     1445                1450                1455
         Asp Val Asn Val Val Arg Leu Ser Ile Asp Gly Gly Lys Thr Trp Phe
                     1460                1465                1470
         Asn Ala Thr Gln Ser Ala Thr Pro Gly Val Trp Asp Tyr Ile Trp Pro
                     1475                1480                1485
         Asp Asp Val Ala Asp Gly Gly Tyr Thr Leu Thr Val Glu Ala Thr Asp
                     1490                1495                1500
         Glu Ala Gly Asn Lys Ala Thr Gln Thr Leu Asp Phe Thr Ile Asp Thr
         1505                1510                1515                1520
         Thr Leu Ser Val Pro Thr Leu Ser Leu Asp Ser Ala Asp Asp Ser Gly
                     1525                1530                1535
         Ile Ala Gly Asp Asn Ile Thr Asn Val Lys Thr Pro Gly Phe Thr Leu
                     1540                1545                1550
         Asn Asn Ile Asp Thr Asp Val Ser Arg Val Ile Val Glu Val Met His
                     1555                1560                1565
         Asn Gly Ile Lys Gln Glu Val Pro Leu Val Gln Thr Gly Gly Gln Trp
                     1570                1575                1580
         Arg Phe Ala Pro Thr Ser Asp Trp Ala Asp Gly Asp Tyr Ile Leu Thr
         1585                1590                1595                1600
         Val Lys Val Glu Asp Arg Ala Gly Asn Val Lys Gln Ser Ala Pro Leu
                     1605                1610                1615
```

```
Thr Val Thr Val Asp Thr His Ile Ala Ile Asp Arg Ile Glu Leu Val
        1620                1625                1630

Asn Asp Ser Gly Ile Pro Gly Asp Asn Leu Thr Asn Glu Ala Arg Pro
        1635                1640                1645

His Phe Gln Val Thr Val Pro Ala Asp Val Asn Gly Val Arg Leu Ser
        1650                1655                1660

Ile Asp Gly Gly Lys Thr Trp Phe Asp Ala Thr Gln Ser Ala Thr Ser
1665                1670                1675                1680

Gly Val Trp Asp Tyr Thr Trp Leu Thr Asn Val Ala Asn Gly Pro His
            1685                1690                1695

Thr Leu Met Val Glu Ala Ser Asp Lys Ala Gly Asn Lys Thr Thr Gln
        1700                1705                1710

Lys Leu Asp Phe Thr Ile Asp Thr Ile Leu Ser Glu Pro Thr Ile Thr
        1715                1720                1725

Leu Asp Ser Ala Asp Asp Ser Ala Ala Gly Asp Asn Ile Thr Asn Val
        1730                1735                1740

Lys Met Pro Gly Phe Thr Leu Gly Asn Ile Asp Ala Asp Val Thr Lys
1745                1750                1755                1760

Val Val Val Thr Val Ala His Asp Gly Lys Asn Gln Gln Ile Glu Leu
            1765                1770                1775

Ile Lys Asn Gly Gly Val Trp Arg Phe Thr Pro Gly Ala Ala Trp Thr
        1780                1785                1790

Asp Gly Asp Tyr Thr Leu Thr Val Lys Val Glu Asp Lys Ala Gly Asn
        1795                1800                1805

Thr Asn Tyr Ser Ala Pro Leu Thr Val Thr Ile Asp Thr Gln Thr Ser
        1810                1815                1820

Ile Asp Arg Ile Glu Leu Leu Asn Asp Thr Gly Ile Val Gly Asp Asn
1825                1830                1835                1840

Leu Thr Asn Glu Ala Arg Pro Gln Phe His Ile Thr Val Pro Thr Asp
        1845                1850                1855

Val Asn Ser Val Gln Leu Ser Leu Asp Gly Gly Ile Asn Trp Val Asn
        1860                1865                1870

Ala Thr Leu Thr Ser Asp Gly Val Trp Glu Tyr Ile Trp Pro Thr Asp
        1875                1880                1885

Leu Val Glu Asn Thr Tyr Thr Leu Thr Val Lys Ala Thr Asp Val Ala
        1890                1895                1900

Gly Asn Thr Ala Thr Glu Thr Leu Asn Phe Ile Ile Asp Thr Thr Leu
1905                1910                1915                1920

Ser Thr Pro Thr Ile Thr Leu Asp Ser Ala Asp Asp Ser Gly Thr Ala
            1925                1930                1935

Asn Asp Asn Lys Thr Asn Val Lys Thr Pro Gly Phe Ile Ile Gly Gly
        1940                1945                1950

Ile Asp Ser Asp Val Thr Gln Val Val Val Gln Val Met Arg Asp Gly
        1955                1960                1965

His Ser Glu Glu Val Glu Leu Thr Gln Thr Asn Gly Gln Trp Arg Phe
        1970                1975                1980

Val Pro Gly Ser Ala Trp Thr Asp Gly Asp Tyr Thr Leu Thr Val Thr
1985                1990                1995                2000

Val Lys Asp Glu Ala Gly Asn Ile Arg His Ser Ala Pro Leu Thr Val
            2005                2010                2015

Thr Ile Asp Thr Gln Ile Thr Ile Asp His Ile Glu Leu Val Asn Asp
        2020                2025                2030
```

-continued

Ser Gly Ile Pro Asp Asp Asn Leu Thr Asn Asn Val Arg Pro His Phe
            2035                2040                2045

Gln Val Thr Val Pro Thr Asp Val Asn Val Val Arg Leu Ser Ile Asp
        2050                2055                2060

Gly Gly Lys Thr Trp Phe Asn Ala Thr Gln Ser Ala Thr Pro Gly Val
2065                2070                2075                2080

Trp Asp Tyr Thr Trp Leu Ala Asp Val Gly Glu Gly Lys His Thr Leu
            2085                2090                2095

Thr Val Glu Ala Thr Asp Lys Ala Gly Asn Lys Thr Thr Gln Gln Leu
        2100                2105                2110

Asp Phe Ile Ile Asp Thr Leu Leu Ser Glu Pro Thr Ile Val Leu Asp
            2115                2120                2125

Ser Thr Asp Asp Ser Gly Thr Lys Gly Asp His Leu Thr Asn Val Asn
        2130                2135                2140

Lys Pro Thr Phe Leu Leu Gly Asn Ile Asp Ala Asp Ala Arg Tyr Val
2145                2150                2155                2160

Thr Val Glu Val Gln His Gly Gly Thr Lys Glu Val Leu Thr Ala Thr
            2165                2170                2175

Lys Asp Ala Thr Gly Asn Trp Ser Val Thr Pro Thr Gly Thr Trp Ala
        2180                2185                2190

Asp Gly Asp Tyr Thr Leu Thr Val Arg Val Glu Asp Glu Ala Gly Asn
            2195                2200                2205

Glu Lys His Ser Ala Ser Leu Thr Val Thr Val Asp Thr Gln Ile Thr
        2210                2215                2220

Ile Asp Val Ile Glu Leu Val Asn Asp Asn Gly Ile Pro Gly Asp Asn
2225                2230                2235                2240

Met Thr Asn Asp Ala His Pro Gln Phe Arg Val Thr Val Pro Gly Asp
            2245                2250                2255

Val Asn Glu Val Ser Leu Ser Ile Asp Gly Gly Val Thr Trp Val Lys
        2260                2265                2270

Ala Thr Gln Ser Ala Thr Pro Gly Val Trp Asn Tyr Thr Trp Pro Gly
            2275                2280                2285

Thr Val Pro Asp Gly Asp Tyr Thr Leu Asn Val Lys Ala Thr Asp Asn
        2290                2295                2300

Ala Gly Asn Thr Val Thr Glu Thr Leu His Phe Thr Ile Asp Thr Thr
2305                2310                2315                2320

Leu Ser Thr Pro Val Ile Val Leu Asp Ser Ala Asp Asp Ser Gly Val
            2325                2330                2335

His Gly Asp Asn Met Thr Asn His Thr Gln Pro Thr Phe Ala Leu Gln
        2340                2345                2350

His Ile Asp Asp Asp Ala Val Arg Val Thr Val Ser Val Glu His Gly
            2355                2360                2365

Gly Val Thr Thr Thr Phe Asp Ala Thr Lys Asp Ala Gly Gly Trp Thr
        2370                2375                2380

Phe Thr Pro Thr Gly Ala Trp Ala Asp Gly Asp Tyr Thr Leu Ser Val
2385                2390                2395                2400

Ser Val Glu Asp Lys Ala Gly Asn Thr Ser His Ser Ala Ser Leu Thr
            2405                2410                2415

Val Thr Val Asp Thr Gln Ile Ala Ile Asn Asn Ile Glu Leu Val Asn
        2420                2425                2430

Asp Ser Gly Ile Pro Asp Asp Asn Leu Thr Asn Asn Val Arg Pro His
            2435                2440                2445

Phe Gln Val Thr Val Pro Thr Asp Val Asn Val Val Arg Leu Ser Ile

```
                2450                2455                2460
Asp Gly Gly Lys Thr Trp Phe Asn Ala Thr Gln Ser Ala Thr Pro Gly
2465                2470                2475                2480

Val Trp Asp Tyr Thr Trp Leu Ala Asp Val Gly Glu Gly Lys His Thr
                2485                2490                2495

Leu Thr Val Glu Ala Thr Asp Lys Ala Gly Asn Lys Thr Thr Gln Gln
                2500                2505                2510

Leu Asp Phe Ile Ile Asp Thr Leu Leu Ser Glu Pro Thr Ile Val Leu
                2515                2520                2525

Asp Asn Thr Asp Asp Ser Gly Thr Lys Gly Asp Asn Leu Thr Asn Val
                2530                2535                2540

Asn Lys Pro Thr Phe Leu Leu Gly Asn Ile Asp Ala Asp Ala Arg Tyr
2545                2550                2555                2560

Val Thr Val Glu Val Gln His Gly Gly Thr Lys Glu Val Leu Thr Ala
                2565                2570                2575

Thr Lys Gly Ala Thr Gly Ile Trp Ser Val Thr Pro Thr Gly Thr Trp
                2580                2585                2590

Ala Asp Gly Asp Tyr Thr Leu Thr Val Arg Val Glu Asp Asp Ala Gly
                2595                2600                2605

Asn Val Lys Tyr Ser Ala Pro Leu Thr Val Thr Val Asp Thr Gln Ile
                2610                2615                2620

Thr Ile Asp Val Ile Glu Leu Val Asn Asp Asn Gly Ile Pro Gly Asp
2625                2630                2635                2640

Asn Leu Thr Asn Asp Val Arg Pro His Phe Arg Val Thr Val Pro Gly
                2645                2650                2655

Asp Val Asn Glu Val Arg Leu Ser Ile Asp Gly Gly Asn Thr Trp Val
                2660                2665                2670

Arg Ala Thr Gln Gly Thr Ala Gly Ile Trp Asp Tyr Thr Trp Pro Lys
                2675                2680                2685

Asp Val Thr Asp Gly Leu His Thr Leu Thr Val Glu Ala Thr Asp Lys
                2690                2695                2700

Ala Gly Asn Lys Thr Thr Gln Thr Leu Asp Phe Thr Ile Asp Thr Arg
2705                2710                2715                2720

Leu Ser Thr Pro Thr Ile Ala Met Asp Ser Arg Asp Asp Thr Gly Ala
                2725                2730                2735

Ile Gly Asp His Ile Thr Ser Val Lys Arg Pro Gly Phe Thr Ile Gly
                2740                2745                2750

Asn Ile Asp Ala Asp Ala His Ser Val Ile Leu Arg Ile Thr Gln Gly
                2755                2760                2765

Gly Asn Ser Gln Glu Val Thr Leu Thr Gln Val Gly Gly Gln Trp Arg
                2770                2775                2780

Phe Thr Pro Asp Ala Asp Trp Ala Asp Gly Ser Tyr Thr Leu Thr Val
2785                2790                2795                2800

Glu Val Thr Asp Asn Ala Gly Asn Val Arg Gln Ser Thr Pro Leu Val
                2805                2810                2815

Val Thr Val Asp Thr Gln Thr Ser Ile Thr Asp Ile Thr Leu Val Asn
                2820                2825                2830

Asp His Gly Val Pro Asp Asp Asn Leu Thr Asn Ser Thr Arg Pro Gln
                2835                2840                2845

Phe Glu Ile Thr Val Pro Ala Asp Val Asn Ser Val Gln Leu Ser Ile
                2850                2855                2860

Asp Gly Gly Ala Asn Trp Val Ser Ala Thr Gln Gly Ile Glu Gly Val
2865                2870                2875                2880
```

-continued

Trp Gly Tyr Thr Trp Pro Thr Asp Met Gly Asp Gly Lys His Thr Leu
                2885            2890            2895

Thr Val Met Val Thr Asp Arg Ala Gly Asn Thr Ala Thr Gln Thr Leu
            2900            2905            2910

Glu Phe Phe Ile Asp Thr Arg Leu Ser Thr Pro Thr Ile Ala Leu Asp
        2915            2920            2925

Ser Thr Asp Asp Thr Gly Thr Pro Gly Asp Asp Met Thr Asn Arg Thr
    2930            2935            2940

Arg Pro Thr Phe Ile Leu Gln Asn Ile Asp Ser Asp Val Ile Asn Val
2945            2950            2955            2960

Thr Val Ser Val Thr His Asn Gly Thr Thr Thr Ser Phe Thr Ala Thr
            2965            2970            2975

Gln Gly Ala Gly Gly Trp Ser Phe Thr Pro Pro Ala Pro Trp Gly Asp
        2980            2985            2990

Gly Asp Tyr Thr Leu Thr Val Thr Val Glu Asp Arg Ala Gly Asn Thr
    2995            3000            3005

Arg Pro Ser Thr Pro Leu Thr Val Thr Val Asp Thr Gln Ile Ala Ile
3010            3015            3020

Asp Arg Ile Glu Leu Val Asn Asp Ser Gly Val Pro Gly Asp Asn Val
            3025            3030            3035            3040

Thr Lys His Val Arg Pro Gln Phe Gln Ile Ser Val Pro Asp Asp Val
        3045            3050            3055

Glu Lys Val Leu Leu Ser Ile Asp Gly Gly Thr Thr Trp Val Thr Ala
    3060            3065            3070

Ile Lys Ser Ser Thr Ala Gly Ile Trp Asp Tyr Thr Trp Pro Thr Asp
    3075            3080            3085

Met Pro Glu Gly Gln His Thr Leu Thr Val Val Thr Val Asp Gly Ala
    3090            3095            3100

Gly Asn Lys Met Thr Glu Thr Leu Asn Phe Thr Ile Asp Ile Thr Leu
3105            3110            3115            3120

Leu Thr Pro Thr Ile Glu Leu Ala Pro Asp Gln Asp Thr Gly Gln Asn
            3125            3130            3135

Lys Asn Asp Asn Leu Thr Ser Val Thr Gln Pro Val Phe Val Leu Gly
        3140            3145            3150

Ser Ile Asp Lys Asp Val Arg His Val Glu Leu Ser Ile Glu His Asn
    3155            3160            3165

Gly Thr Phe Lys Thr Val Val Leu Thr Glu Ser Ala Asp Gly Trp Arg
    3170            3175            3180

Tyr Arg Pro Asp Ser Ala Leu Ala Asp Gly Ser Tyr Thr Phe Thr Val
3185            3190            3195            3200

Thr Val Thr Asp Val Ala Gly Asn Gln Gln Thr Ser Ala Pro Leu Lys
            3205            3210            3215

Val Thr Ile Asp Gly Thr Leu Thr Thr Pro Val Ile Glu Leu Ala Ala
        3220            3225            3230

Gly Glu Asp Ser Gly Thr Val Gly Asp Arg Leu Thr Asn His Asp Arg
    3235            3240            3245

Pro Val Phe Asp Ile His Gln Val Asp Ser Asp Val Thr Arg Val Met
    3250            3255            3260

Val Lys Val Thr Tyr Asn Gly Lys Thr His Glu Glu Ala Ala Val Phe
3265            3270            3275            3280

Thr Asn Gly Gln Trp Arg Phe Thr Pro Ser Ala Ser Trp Ala Asp Gly
            3285            3290            3295

```
Ser Tyr Gln Leu Ala Val Val Glu Asp Leu Ala Gly Asn Val Lys
            3300                3305                3310

Glu Ser Ala Pro Phe Glu Val Arg Ile Asp Thr Thr Thr Ile Asn
        3315                3320                3325

Asn Ile Val Leu Leu Asn Asp Thr Gly Val Gln Asn Asp Gln Leu Thr
    3330                3335                3340

Asn Val Ala Lys Pro Ser Phe Arg Ile Asp Val Pro Gly Asp Val Val
3345                3350                3355                3360

Gln Val Arg Val Thr Leu Asp Gly Gly Ala Asn Trp Asn Val Ile Arg
            3365                3370                3375

Lys Asn Ala Asp Gly Gln Trp Ile Phe Asp Ser Pro Asn Thr Leu Val
        3380                3385                3390

Asp Gly Thr Tyr Thr Leu Arg Val Glu Ala Thr Asp Glu Ala Gly Asn
            3395                3400                3405

Ile Ala Asn Lys Asp Leu Val Phe Asn Ile Asp Thr Asn Ile Gln Val
        3410                3415                3420

Pro Thr Ile Ala Leu Asp Ala Gly Gln Asp Thr Gly Ala Asn Thr Ala
3425                3430                3435                3440

Asp Asn Ile Thr Asn Ile Ser Arg Pro Thr Phe Thr Ile Gly Asn Val
            3445                3450                3455

Asp Pro Asp Val Ile Lys Val Val Thr Ile Asp Gly His Asp Tyr
        3460                3465                3470

Asn Ala Thr Lys Val Gly Ala Gly Trp Gln Phe Thr Pro Gly Asn Ala
    3475                3480                3485

Ile Pro Asp Gly Ser Tyr Asn Ile Thr Val Thr Val Glu Asp Lys Ala
            3490                3495                3500

Gly Asn Thr Ala Thr Ser Lys Pro Leu Pro Val Val Ile Asp Thr Thr
3505                3510                3515                3520

Ala Glu Ile Glu Ser Val Thr Leu Val Thr Asp Ser Gly Asp Ser Asp
            3525                3530                3535

Val Asp Asn Ile Thr Lys Val Asp Lys Pro Gln Phe Ser Ile Val Thr
        3540                3545                3550

Ala Asp Asp Ile Thr His Val Arg Val Lys Ile Asp Asn Ala Ala Asn
            3555                3560                3565

Trp Ile Glu Leu Thr Lys Gly Gly Asp Gly Arg Trp Ile Phe Asn Val
    3570                3575                3580

Gly Ser Ala Leu Pro Asp Gly Gln His Thr Leu Leu Val Asp Val Thr
3585                3590                3595                3600

Asp Ile Ala Gly Asn Val Ala Gln Glu Thr Leu Gln Phe Thr Ile Asp
            3605                3610                3615

Thr Thr Leu Arg Glu Pro Thr Ile Val Leu Asp Pro Thr His Asp Thr
        3620                3625                3630

Gly Asp Thr Asn Asp Asn Leu Thr Arg Ile Asn Lys Pro Val Phe
            3635                3640                3645

Ile Ile Gly Asn Val Asp Asn Asp Val Ser His Ile Val His Ile
        3650                3655                3660

Asp Gly Arg Asp Tyr Thr Ile Glu Asn Thr Gly Gly Asn Leu Thr Phe
3665                3670                3675                3680

Thr Pro Asp Gln Pro Leu Ser Asp Gly Gln His Thr Ile Ser Val Thr
            3685                3690                3695

Val Thr Asp Ile Ala Gly Asn Thr Lys Thr Ser Ala Glu Leu Arg Ile
        3700                3705                3710

Glu Ile Asp Thr Gln Val Gln Ile Asp Ser Val Thr Leu Thr Thr Asp
```

```
            3715                3720                3725
Ser Gly Val Asn Asp His Asp Asn Val Thr Asn Ala Thr Arg Pro Ser
            3730                3735            3740
Phe Glu Ile Ala Thr Pro Asp Val Thr Ser Val Leu Val Ser Phe
3745                3750                3755                3760
Asp Gly Val Asn Trp Thr Pro Ile Ser Lys Asn Ala Ala Gly Gln Trp
                3765                3770                3775
Glu Phe Thr Ala Gly Ser Ala Leu Pro Asp Gly His Tyr Thr Leu His
            3780                3785            3790
Val Gln Ala Thr Asp Arg Ala Gly Asn Thr Ala Asn Ser Thr Leu Gly
            3795                3800                3805
Phe Thr Val Asp Thr Gln Ile Asp Gly Leu Ser Val Val Met Leu Asp
            3810                3815            3820
Asp Ala Gly Lys Asp Ser Thr Asp Gly Ile Thr Asn Ile Thr Ser Pro
3825                3830                3835                3840
Arg Phe Glu Ile Ser Ala Arg Glu Pro Leu Gln Ser Val Thr Val Ile
                3845                3850                3855
Leu Asn Gly Lys Ser Ser Thr Leu Thr Gln Gly Ala Gly Asn Lys Trp
            3860                3865            3870
Leu Phe Thr Pro Asp Thr Pro Leu Val Asp Gly Thr Tyr Lys Ile Glu
            3875                3880            3885
Ile Val Ala Glu Asp Ile Ala Gly Asn Lys Ile Ser Lys Glu Val Ser
            3890                3895            3900
Phe Thr Ile Asp Thr Ile Val Ser Asp Pro Ser Ile Asp Leu Leu Asp
3905                3910                3915                3920
Ala Asp Asp Thr Gly Glu Ser Ala Val Asp Asn Ile Thr Ser Val Thr
                3925                3930                3935
Thr Pro Arg Phe Val Ile Gly Asn Val Pro Ala Asp Ile Asp Thr Val
            3940                3945            3950
Val Ile Arg Ile Asn Gly Val Ser Tyr Pro Val Thr Ala Asn Gly Asn
            3955                3960            3965
Asn Leu Trp Glu Phe Gln Val Pro Val Ala Leu Asn Asp Gly Val Tyr
            3970                3975            3980
Glu Ala Val Val Val Phe Arg Asp Ile Ala Gly Asn Thr Ser Glu Thr
3985                3990                3995                4000
Lys Leu Pro Phe Thr Ile Asp Thr Thr Thr Ser Val Ser Val Arg Met
                4005                4010                4015
Glu Pro Ala Ser Asp Thr Gly Asn Ser Asn Ser Asp Asn Leu Thr Asn
            4020                4025            4030
Lys Gln Asn Pro Lys Phe Glu Gly Thr Ala Glu Pro Asn Ala Lys Leu
            4035                4040            4045
Val Ile Thr Ile Val Asp Asp Lys Ser Gly Arg Glu Val Leu Lys Gln
            4050                4055            4060
Thr Ile Thr Val Gly Ala Asp Gly Asn Trp Ser Val Thr Pro Asn Ile
4065                4070                4075                4080
Leu Pro Asp Gly Met Tyr Thr Ile Asn Val Val Ala Thr Asp Val Ala
                4085                4090                4095
Gly Asn Thr Ala Gln Thr Gln Glu Arg Phe Thr Ile Asp Thr Val Thr
            4100                4105            4110
Ile Asp Pro Thr Ile Arg Leu Ser Asp Pro Ser Ile Asp Asp Gln His
            4115                4120            4125
Glu Ala Thr Ser Leu Arg Pro Glu Phe Lys Gly Phe Ala Glu Ala Phe
            4130                4135            4140
```

```
Ser Thr Ile Met Ile Gln Trp Asp Gly Lys Val Val Gly Ser Ala Asn
4145                4150                4155                4160

Ala Asn Ala Asn Gly Glu Trp Ser Trp Thr Pro Pro Ser Val Leu Ala
                4165                4170                4175

Pro Gly Ser Tyr Val Val Ser Ile Val Ala Lys Asp Lys Ala Gly Asn
            4180                4185                4190

Glu Ser Ser Gln Val Asp Phe Pro Val Val Ile Pro Val Ile Asp Val
        4195                4200                4205

Thr Pro Pro Thr Ile Lys Leu Ser Glu Glu Ser Asp Ser Gly Ala Leu
    4210                4215                4220

Gly Asp Phe Thr Thr Asn Asn Lys Thr Pro Thr Leu Ile Gly Ser Thr
4225                4230                4235                4240

Leu Pro Asn Thr Ile Val Ser Ile Tyr Val Asp Gly Val Lys Val Gly
                4245                4250                4255

Glu Ala Thr Ala Asp Thr Ala Gly Arg Tyr Thr Phe Gln Leu Ser Glu
            4260                4265                4270

Met Lys Asp Gly His Tyr Val Val Gln Val Gly Ile Val Asn Pro Arg
        4275                4280                4285

Asp Asn Ser Glu Leu Arg Ser Thr Ala Val Asp Val Thr Ile Asp Thr
    4290                4295                4300

Glu Val Ala Glu Leu Val Trp Asn Ile Ser Gly Met His Glu Gly Gly
4305                4310                4315                4320

Tyr Ile Asn Thr Val Thr Pro Glu Ile Gly Gly Thr Ser Glu Pro Asn
                4325                4330                4335

Ser Lys Ile Thr Ile Phe Val Asn Gly Val Glu Lys Ala Ile Ala Tyr
            4340                4345                4350

Thr Thr Gly Ala Gly His Trp Gly Val Val Leu Pro Ala Leu Gly Asn
        4355                4360                4365

Asp Gly Asn Tyr Glu Leu Thr Phe Lys Val Glu Asp Val Ala Gly Asn
    4370                4375                4380

Ile Arg Glu Phe Gly Pro Gln Asn Val Ile Leu Asp Thr Val Ile Ser
4385                4390                4395                4400

Pro Leu Thr Val Val Leu Arg Glu Ala Asp Asp Ser Gly Lys Val Gly
                4405                4410                4415

Asp Trp Ile Thr Asn Lys Ser His Val Thr Ile Asp Gly Thr Ala Glu
            4420                4425                4430

Ala Gly Ser Thr Leu Thr Ile Arg Asn Pro Gln Gly Val Val Ile Ala
        4435                4440                4445

Thr Leu Val Val Gly Asn Asp Gly Arg Trp Ser Ala Glu Leu Asp Leu
    4450                4455                4460

Arg Glu Gly Ser Asn Ala Phe Val Val Val Ser Glu Asp Lys Ala Gly
4465                4470                4475                4480

Asn Ser Gln Gln Lys Glu Ile Leu Ile Glu His Asp Thr Gln Ile Glu
                4485                4490                4495

Ile Ser Asp Ile Ser Leu Ser Arg Asp Thr Asn Ser Gly Asp Lys Tyr
            4500                4505                4510

Asp Leu Ile Thr Asn Asn Lys Ser Pro Val Leu Val Ala Met Thr Asp
        4515                4520                4525

Pro Gly Ala Thr Val Gln Val Tyr Ile Asn Gly Val Leu Gln Gly Thr
    4530                4535                4540

Val Glu Ala Ser Ser Ser Gly Asn Ile Ser Tyr Thr Met Pro Ala Asn
4545                4550                4555                4560
```

-continued

Ser Ala Asp Gly Glu Tyr Gln Val Gln Phe Val Ala Thr Asp Thr Ala
            4565                4570                4575

Gly Asn Arg Val Glu Ser Ala Ile Thr Thr Val Thr Ile Asp Ser Gln
            4580                4585                4590

Ile Ala Val Phe Asp Ile Asp Glu Asp Ser Leu Pro Ala Leu Ser Asn
            4595                4600                4605

Asn Arg Ala Leu Ser Val Ser Gly Val Gly Glu Ala Gly Ser Gln Val
            4610                4615                4620

Ser Ile Phe Val Asp Gly Lys Leu Val Asn Val Val Met Val Glu Ala
4625                4630                4635                4640

Asp Gly Thr Trp Arg Ala Pro Ile Leu Leu Gln Asp Asp Gly Thr Phe
            4645                4650                4655

Asn Ile His Phe Ser Ile Thr Asp Val Ala Gly Asn Thr Glu Val Ser
            4660                4665                4670

Lys Asp Tyr Ser Val Asp Val Asp Ser Ser Thr Asp Phe Pro Thr Leu
            4675                4680                4685

Asn Leu Glu Asp Ala Ser Asn Ser Gly Ser Leu Asp Asp Leu Ile Thr
            4690                4695                4700

Asn His Asn Lys Pro Val Leu Val Gly Thr Ala Glu Ala Gly Ala Thr
4705                4710                4715                4720

Ile His Ile Tyr Val Asp Glu Lys Ile Val Ala Asn Val Leu Val Leu
            4725                4730                4735

Glu Asp Gly Thr Trp Ser Tyr Gln Phe Asp Asn Ala Leu Lys Asp Gly
            4740                4745                4750

Glu Tyr Ser Ile Arg Val Val Ala Glu Asp Pro Ala Gly Asn Thr Ala
            4755                4760                4765

Glu Ser Pro Arg Leu Leu Val Thr Ile Asp Thr Ser Thr Phe Ile Asp
            4770                4775                4780

Asn Pro Ala Met Val Ala Gly Ser Asp Asn Gly Ile Phe Ser Asn Asp
4785                4790                4795                4800

Ser Ile Thr Ser Gln Thr Arg Pro Thr Phe Ser Ile Phe Gly Glu Met
            4805                4810                4815

Asn Gln Ser Val Gln Ile Phe Ile Asp Gly Val Leu Val Asp Thr Ile
            4820                4825                4830

Thr Val Thr Asp Arg Asn Gln Val Tyr Arg Pro Glu Ser Pro Leu Gly
            4835                4840                4845

Asp Gly Ser His Ser Ile Tyr Tyr Val Ile Thr Asp Lys Ala Gly Asn
            4850                4855                4860

Thr Ala Thr Ser Lys Thr Leu Asn Phe Thr Ile Asp Thr Phe Asn Thr
4865                4870                4875                4880

Thr Pro Val Ala Ile Asp Ser Ile Gly Gly Gln Thr Leu Ala Glu Met
            4885                4890                4895

Thr Gly Ser Asp Gly Lys Ile Tyr Ile Thr Asp Thr Thr Arg Asn Leu
            4900                4905                4910

Leu Phe Ser Gly Ser Ala Glu Pro Asn Ser Lys Ile Glu Ile Ile Ile
            4915                4920                4925

Asn Gly Leu Asn Val Gly Glu Val Trp Val Asn Glu Lys Gly His Trp
            4930                4935                4940

Gln Met Pro Val Asn Pro Leu Tyr Phe Thr Glu Gly Gln Leu Asp Ile
4945                4950                4955                4960

Thr Val Lys Ser Thr Asp Arg Ala Gly Asn Val Asn Gln Glu Lys Tyr
            4965                4970                4975

Ser Ile Trp Val Asp Thr His Ile Lys Val Phe Thr Ser Glu Leu Asp

-continued

```
                4980                4985                4990
Asp Asn Lys Ser Ser Lys Thr Glu Trp Trp Ser Asn Ser Asp Leu
        4995                5000                5005
Ile Thr Met Arg Gly Thr Gly Glu Ile Gly Ala Thr Val Ser Leu Ile
    5010                5015                5020
Val Ala Gly Val Thr Leu Ala Thr Ala Val Ala Ala Thr Gly Arg
5025                5030                5035                5040
Trp Glu Leu Ser Thr Asp Lys Leu Pro Glu Gly Thr Tyr Asp Ile Ser
            5045                5050                5055
Leu Val Ile Glu Asp Ser Ala Gly Asn Arg Trp Glu Asp Val Arg Glu
        5060                5065                5070
Ile Phe Ile Asp Arg Thr Pro Pro Asn Ala Pro Val Val Thr Tyr Ser
        5075                5080                5085
Asp Ile Val Asn Asp Leu Ile Ile Met Gln Gly Thr Ala Glu Ala Lys
        5090                5095                5100
Ser Gln Leu Ile Ile Thr Asp Ser Glu Gly Asn Thr Tyr Thr Leu Thr
5105                5110                5115                5120
Val Pro Asp Asn Gly Lys Trp Ser Met Ala Ile Pro Tyr Pro Ser Glu
            5125                5130                5135
Gly Lys Phe Thr Ile Thr Ser Val Asp Ala Ile Gly Asn Arg Ser Asp
        5140                5145                5150
Asp Val Pro Leu Asp Ile Met Lys Glu Val Pro Val Ile Ser Leu Ser
        5155                5160                5165
Pro Asp Ser Asp Ser Gly Thr Val Gly Asp Asn Ile Thr Arg Asp Lys
        5170                5175                5180
Gln Pro Thr Phe Ile Ile Gly Asn Leu Glu Ser Asp Val Val Val
5185                5190                5195                5200
Gln Val Asp Ile Asn Gly Thr Val Tyr Asn Ala Glu Lys Asn Ala Asp
            5205                5210                5215
Gly Val Trp Phe Phe Thr Pro Gly Thr Pro Leu Ala Asp Gly Ser Tyr
            5220                5225                5230
Thr Ile Ser Val Ile Ala Ser Asp Ala Ala Gly Asn Gln Lys Asn Ser
        5235                5240                5245
Leu Pro Ile Thr Val Thr Ile Asp Ser Thr Leu Thr Val Pro Glu Ile
        5250                5255                5260
Ala Leu Ala Ala Gly Glu Asp Asn Gly Ala Ser Asp Ser Asp Asn Val
5265                5270                5275                5280
Thr Asn His Thr Gln Pro Lys Phe Thr Leu Gln His Ile Asp Ala Asp
            5285                5290                5295
Val Thr Gly Val Thr Val Asn Val Thr His Asn Gly Val Thr Asp Ile
            5300                5305                5310
Tyr Gln Ala Thr Gln Gly Ala Asp Gly Trp Thr Phe Thr Pro Pro Ala
        5315                5320                5325
Ala Trp Asn Asp Gly Asn Tyr Thr Leu Ser Val Thr Val Asp Arg
        5330                5335                5340
Ala Gly Asn Ser Gln Gln Ser Ala Ser Leu Ala Val Thr Val Asp Ser
5345                5350                5355                5360
Thr Val Thr Val Thr Ala Asp Ser Gln His Asp Asp Ala Ser Asp Asp
            5365                5370                5375
Ala Thr Ala Thr Ala Val Thr Pro Pro Glu Ser Glu Thr Val Asn Ala
        5380                5385                5390
Glu Ser Ala Thr His Leu Arg Thr Glu Pro Ser Ala Ala Glu Glu Ser
        5395                5400                5405
```

```
Val Val Lys Val Thr Ala Tyr Ser Ile Thr Leu Leu Asn Ala Asp Ser
        5410                5415                5420

Gly Asp Glu Ile Asp Arg Ser Ile Ser Gln Thr Pro Ser Phe Glu Ile
5425                5430                5435                5440

Ser Val Pro Glu Asn Ile Val Asn Val Ser Ile Met Phe Glu Gly Glu
            5445                5450                5455

Glu Phe Thr Leu Pro Ile Thr Asn Gln Lys Ala Ile Phe Glu Val Pro
            5460                5465                5470

Leu Ser Leu Glu Asp Gly Glu Tyr Thr Met Asp Val Lys Phe Ile Asp
        5475                5480                5485

Lys Asp Asn Asp Phe Leu Ile Lys Glu Lys Thr Phe Ser Val Asp His
        5490                5495                5500

Ser Ser Ala Asp Ile Val Asn Ala Met Asn Val Arg Gly Lys Thr Glu
5505                5510                5515                5520

Asp Asp Ile Asn Asp Ser Pro Ser Thr Ser Val Gly His Asn Asn
            5525                5530                5535

Asn Gly Ala Ile Asp Val Phe Ala Val Asn Glu Val Thr Leu Pro Val
            5540                5545                5550

Asp Asn Gln Glu Glu His Ala
        5555

<210> SEQ ID NO 6
<211> LENGTH: 44
<212> TYPE: PRT
<213> ORGANISM: Mus musculus

<400> SEQUENCE: 6

Val Thr Ala Asp Met Val Lys Glu Ala Leu Glu Glu Ala Glu Lys Ala
1               5                   10                  15

Gln Val Ala Ala Glu Lys Ala Ile Lys Gln Ala Asp Glu Asp Ile Gln
            20                  25                  30

Gly Thr Gln Asn Leu Leu Thr Ser Ile Glu Ser Glu
        35                  40

<210> SEQ ID NO 7
<211> LENGTH: 44
<212> TYPE: PRT
<213> ORGANISM: Homo sapiens

<400> SEQUENCE: 7

Val Thr Ala Asp Met Val Lys Glu Ala Leu Glu Glu Ala Glu Lys Ala
1               5                   10                  15

Gln Val Ala Ala Glu Lys Ala Ile Lys Gln Ala Asp Glu Asp Ile Gln
            20                  25                  30

Gly Thr Gln Asn Leu Leu Thr Ser Ile Glu Ser Glu
        35                  40

<210> SEQ ID NO 8
<211> LENGTH: 404
<212> TYPE: PRT
<213> ORGANISM: Salmonella enterica

<400> SEQUENCE: 8

Met Gly Asn Lys Ser Ile Gln Lys Phe Phe Ala Asp Gln Asn Ser Val
1               5                   10                  15

Ile Asp Leu Ser Ser Leu Gly Asn Ala Lys Gly Ala Lys Val Ser Leu
            20                  25                  30
```

```
Ser Gly Pro Asp Met Asn Ile Thr Thr Pro Arg Gly Ser Val Ile Ile
         35                  40                  45

Val Asn Gly Ala Leu Tyr Ser Ile Lys Gly Asn Asn Leu Ala Val
 50                  55                  60

Lys Phe Lys Asp Lys Thr Ile Thr Gly Ala Lys Ile Leu Gly Ser Val
 65                  70                  75                  80

Asp Leu Lys Asp Ile Gln Leu Glu Arg Ile Asp Ser Ser Leu Val Asp
                 85                  90                  95

Ser Ala Gln Val Glu Lys Lys Gly Asn Gly Lys Arg Arg Asn Lys Lys
                100                 105                 110

Glu Glu Glu Glu Leu Lys Lys Gln Leu Asp Asp Ala Glu Asn Ala Lys
                115                 120                 125

Lys Glu Ala Asp Lys Ala Lys Glu Glu Ala Glu Lys Ala Lys Glu Ala
130                 135                 140

Ala Glu Lys Ala Leu Asn Glu Ala Phe Glu Val Gln Asn Ser Ser Lys
145                 150                 155                 160

Gln Ile Glu Glu Met Leu Gln Asn Phe Leu Ala Asp Asn Val Ala Lys
                165                 170                 175

Asp Asn Leu Ala Gln Gln Ser Asp Ala Ser Gln Gln Asn Thr Gln Ala
                180                 185                 190

Lys Ala Thr Gln Ala Ser Lys Gln Asn Asp Ala Glu Lys Val Leu Pro
                195                 200                 205

Gln Pro Ile Asn Lys Asn Thr Ser Thr Gly Lys Ser Asn Ser Ser Lys
                210                 215                 220

Asn Glu Glu Asn Lys Leu Asp Ala Glu Ser Val Lys Glu Pro Leu Lys
225                 230                 235                 240

Val Thr Leu Ala Leu Ala Ala Glu Ser Asn Ser Gly Ser Lys Asp Asp
                245                 250                 255

Ser Ile Thr Asn Phe Thr Lys Pro Gln Phe Val Gly Ser Thr Ala Pro
                260                 265                 270

Asn Ala Thr Val Ile Ile Lys Ile Asn Gly Ile Ala Val Gly Gln Ala
                275                 280                 285

Val Ala Asp Ser Leu Gly Asn Phe Thr Phe Thr Ala Pro Glu Thr Leu
290                 295                 300

Thr Asp Gly Thr Tyr Asn Leu Glu Ala Glu Ala Lys Thr Ala Asp Gly
305                 310                 315                 320

Ser Gly Ser Ala Lys Leu Val Ile Thr Ile Asp Ser Val Thr Asp Lys
                325                 330                 335

Pro Thr Phe Glu Leu Ser Pro Glu Ser Ser Val Ser Gly His Lys Gly
                340                 345                 350

Leu Thr Pro Thr Leu Thr Pro Ser Ile Val Gly Thr Ala Glu Glu Asn
                355                 360                 365

Ala Lys Val Asp Ile Tyr Val Asp Asn Lys Leu Val Ala Ser Val Asp
370                 375                 380

Val Asp Lys Asp Gly Asn Trp Ser Tyr Glu Phe Lys Asp Asn Glu Leu
385                 390                 395                 400

Ser Glu Gly Glu

<210> SEQ ID NO 9
<211> LENGTH: 44
<212> TYPE: PRT
<213> ORGANISM: Sus scrofa

<400> SEQUENCE: 9
```

```
Val Thr Ala Asp Met Val Lys Glu Ala Leu Glu Glu Ala Glu Lys Ala
1               5                   10                  15

Gln Ile Ala Ala Glu Lys Ala Ile Lys Gln Ala Asp Glu Asp Ile Gln
            20                  25                  30

Gly Thr Gln Asn Leu Leu Thr Ser Ile Glu Ser Glu
        35                  40
```

<210> SEQ ID NO 10
<211> LENGTH: 44
<212> TYPE: PRT
<213> ORGANISM: Orcinus orca

<400> SEQUENCE: 10

```
Val Thr Ala Asp Met Val Lys Glu Ala Leu Glu Glu Ala Glu Lys Ala
1               5                   10                  15

Gln Ile Ala Ala Glu Lys Ala Ile Lys Gln Ala Asp Glu Asp Ile Gln
            20                  25                  30

Gly Thr Gln Asn Leu Leu Thr Ser Ile Glu Ser Glu
        35                  40
```

<210> SEQ ID NO 11
<211> LENGTH: 44
<212> TYPE: PRT
<213> ORGANISM: Bos taurus

<400> SEQUENCE: 11

```
Val Thr Ala Asp Met Val Arg Glu Ala Leu Glu Glu Ala Glu Lys Ala
1               5                   10                  15

Gln Ile Ala Ala Glu Lys Ala Ile Lys Gln Ala Asp Glu Asp Ile Gln
            20                  25                  30

Gly Thr Gln Asn Leu Leu Thr Ser Ile Glu Ser Glu
        35                  40
```

<210> SEQ ID NO 12
<211> LENGTH: 44
<212> TYPE: PRT
<213> ORGANISM: Alligator mississippiensis

<400> SEQUENCE: 12

```
Val Thr Ala Asp Met Val Lys Glu Ala Leu Glu Glu Ala Glu Lys Ala
1               5                   10                  15

Gln Asn Ala Ala Glu Lys Ala Ile Lys Gln Ala Asp Glu Asp Ile Lys
            20                  25                  30

Gly Thr Gln Asp Leu Leu Thr Ser Ile Glu Ser Glu
        35                  40
```

<210> SEQ ID NO 13
<211> LENGTH: 44
<212> TYPE: PRT
<213> ORGANISM: Gallus gallus

<400> SEQUENCE: 13

```
Val Thr Ala Asp Met Val Lys Ala Ala Leu Glu Glu Ala Glu Lys Ala
1               5                   10                  15

Gln Asp Ala Ala Glu Lys Ala Ile Lys Gln Ala Asp Glu Asp Ile Lys
            20                  25                  30

Gly Thr Gln Asp Leu Leu Thr Ser Ile Gln Ser Glu
        35                  40
```

<210> SEQ ID NO 14

```
<211> LENGTH: 22
<212> TYPE: DNA
<213> ORGANISM: Artificial Sequence
<220> FEATURE:
<223> OTHER INFORMATION: PCR primer

<400> SEQUENCE: 14
aaaccagtca gcctgagcta cc                                              22

<210> SEQ ID NO 15
<211> LENGTH: 17
<212> TYPE: DNA
<213> ORGANISM: Artificial Sequence
<220> FEATURE:
<223> OTHER INFORMATION: PCR primer

<400> SEQUENCE: 15
ggctctggcg atgtggc                                                    17

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16
ctggaggccc agggagacat                                                 20

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17
gcacggtcag gatcagaagg                                                 20

<210> SEQ ID NO 18
<211> LENGTH: 22
<212> TYPE: DNA
<213> ORGANISM: Artificial Sequence
<220> FEATURE:
<223> OTHER INFORMATION: PCR primer

<400> SEQUENCE: 18
atcctcgctt caatgcccat gg                                              22

<210> SEQ ID NO 19
<211> LENGTH: 22
<212> TYPE: DNA
<213> ORGANISM: Artificial Sequence
<220> FEATURE:
<223> OTHER INFORMATION: PCR primer

<400> SEQUENCE: 19
ggtgatgcac acctctgtga tg                                              22

<210> SEQ ID NO 20
<211> LENGTH: 19
<212> TYPE: DNA
<213> ORGANISM: Artificial Sequence
<220> FEATURE:
<223> OTHER INFORMATION: PCR primer

<400> SEQUENCE: 20
```
tcctcctcag accgctttt                                                     19

<210> SEQ ID NO 21
<211> LENGTH: 21
<212> TYPE: DNA
<213> ORGANISM: Artificial Sequence
<220> FEATURE:
<223> OTHER INFORMATION: PCR primer

<400> SEQUENCE: 21
cataacctgg ttcatcatcg c                                                  21

<210> SEQ ID NO 22
<211> LENGTH: 62
<212> TYPE: DNA
<213> ORGANISM: Artificial Sequence
<220> FEATURE:
<223> OTHER INFORMATION: primer for cloning

<400> SEQUENCE: 22
ttaccacgcc gcgtggttca gtgatcattg tcaatggcgc tcgtgtaggc tggagctgct        60
tc                                                                       62

<210> SEQ ID NO 23
<211> LENGTH: 62
<212> TYPE: DNA
<213> ORGANISM: Artificial Sequence
<220> FEATURE:
<223> OTHER INFORMATION: primer for cloning

<400> SEQUENCE: 23
gtgctgtcca gcacgatagt cggttctgac agtagggtat cgcatatgaa tatcctcctt       60
ag                                                                       62

<210> SEQ ID NO 24
<211> LENGTH: 20
<212> TYPE: DNA
<213> ORGANISM: Artificial Sequence
<220> FEATURE:
<223> OTHER INFORMATION: primer for cloning verification

<400> SEQUENCE: 24
taatgccaaa ggcgcaaaag                                                    20

<210> SEQ ID NO 25
<211> LENGTH: 20
<212> TYPE: DNA
<213> ORGANISM: Artificial Sequence
<220> FEATURE:
<223> OTHER INFORMATION: primer for cloning verification

<400> SEQUENCE: 25
tacgttggtc aggtgatcgc                                                    20

<210> SEQ ID NO 26
<211> LENGTH: 32
<212> TYPE: DNA
<213> ORGANISM: Artificial Sequence
<220> FEATURE:
<223> OTHER INFORMATION: PCR primer for amplification of plasmid
      sequence

<400> SEQUENCE: 26
ctgggatcct ctgctcaggt agaaaagaaa gg                                      32

```
<210> SEQ ID NO 27
<211> LENGTH: 35
<212> TYPE: DNA
<213> ORGANISM: Artificial Sequence
<220> FEATURE:
<223> OTHER INFORMATION: PCR primer for amplification of plasmid
      sequence

<400> SEQUENCE: 27
ctcgagtcga cttacaaaaa gttctgcagc atttc                              35
```

SALMONELLA SIIE-DERIVED PEPTIDES FOR MANIPULATION OF LONG-LIVED PLASMA CELLS

FIELD

The invention relates to an isolated polypeptide comprising or consisting of an amino acid sequence according to SEQ ID NO 1 (EEAEKAKEAAEKALNEAFE) or an amino acid sequence with a sequence identity of least 70%, preferably of at least 80%, more preferably of at least 90% to SEQ ID NO 1, wherein the polypeptide is no longer than 200, preferably no longer than 170 amino acids. The invention relates to a nucleic acid encoding for said polypeptide, a gene therapy vector comprising said nucleic acid and genetically modified cells expressing said polypeptide.

Furthermore, the invention relates to the medical use of said polypeptide, said nucleic acid, said gene therapy vector and/or said cell for the treatment of a disease associated with pathogenic long-lived plasma cells.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 32352524_1.TXT, the date of creation of the ASCII text file is Mar. 5, 2020, and the size of the ASCII text file is 56.9 KB.

BACKGROUND

BM is the central tissue for hematopoesis as well as for immunological memory. Hematopoietic stem cells, B-cell precursors, plasma cells and memory T cells reside in distinct specialized stromal niches in the BM (Nagasawa et al., 2006; Wilson and Trumpp, 2006; Tokoyoda et al., 2010). These stromal niches provide cell adhesion molecules like VCAM-1, laminin, fibronectin and collagens, as well as cytokines and chemokines such as CXCL12, IL-7, IL-15, Kit ligand, SCF, Flt3 ligand to support survival, expansion and differentiation of hematopoietic cells (Clark and Keating, 1995; Anthony and Link, 2014). In the late phase of immune responses, some antigen-experienced plasma blasts migrate into the BM in a CXCR4/CXCL12-dependent manner (Hargreaves et al., 2001; Tokoyoda et al., 2004) and reside there as long-lived 'memory' plasma cells (Radbruch et al., 2006). Eosinophils and megakaryocytes play an important role as components of survival niches for plasma cells, secreting APRIL and IL-6 to promote plasma cell survival (O'Connor et al., 2004; Winter et al., 2010; Chu et al., 2011). Reynolds et al. showed that IgM-secreting plasma cells do not co-localize with eosinophils like IgG-secreting plasma cells, suggesting that IgM- and IgG-secreting plasma cells localize in distinct survival niches in the BM (Reynolds et al., 2015). However, it still remains unclear whether class-switched and un-switched plasma cells share the same survival niches.

Long-lived plasma cells are refractory to immunosuppressants and B-cell depletion therapies contribute to the maintenance of humoral memory and, in autoimmunity, to autoreactive memory. Consequently, long-lived plasma cells can support chronic inflammatory processes in autoimmune diseases by continuously secreting pathogenic antibodies. As long-lived plasma cells are not sufficiently eliminated by current therapies, there remains a significant need in the art to develop new therapeutic concepts for the treatment of diseases associated with pathogenic long-lived plasma cells such as multiple myeloma or autoimmune diseases.

The gram-negative bacterium *Salmonella* enterica is responsible for high mortality and morbidity in human worldwide (Andrews-Polymenis et al., 2010). *Salmonella* enterica serovar Typhi causes enteric fever and kills around 200,000 persons every year. *Salmonella* enterica serovar Typhimurium has been widely used as an experimental model for typhoid fever (Santos et al., 2001). Following infection via intestinal epithelia, *Salmonella* invades myeloid cells, which migrate into the spleen and liver (Bueno et al., 2008; Dougan and Baker, 2014; Tam et al., 2014). *Salmonella* can stay in myeloid cells for long periods of time. However, it is still unknown how *Salmonella* can survive long-term in short-lived and mobile myeloid cells to escape from humoral immunity.

It has been described previously that *Salmonella* enterica serovar Typhimurium encodes for a type I secretion system, which secretes an □600-kDa protein called SiiE (encoded by siiE). SiiE is surface expressed and it influences colonization in cattle and the invasion of bovine enterocytes (E. Morgan et al. Infection and Immunity, vol. 75, no. 3, 1 March 2007, pages 1524-1533). The sequence of SiiE has been described in WO 02/077183 A2, which relates to the use of nucleic acid antisense sequences for inhibiting proliferation of prokaryotes and identifying proteins required for proliferation, with the goal of developing antibiotics.

Infection with *Salmonella* enterica serovar Typhi can be prevented by vaccination with attenuated strains, e.g. Ty21a (Anwar et al., 2014). In contrast, vaccination against *Salmonella* enterica serovar Typhimurium, which causes severe food poisoning in humans, cattle, swine, sheep, horses, rodents and galliformes is not yet available. The use of attenuated genetically engineered bacteria for immunization has been described in the prior art (U.S. Pat. No. 8,771,669 B1). However, diseases caused by these invasive nontyphoidal *Salmonella* (NTS), including *Salmonella* enterica serovar Typhimurium, have been neglected, although the fatality rate at 20-25% is higher than that by infection with *Salmonella* enterica serovar Typhi (MacLennan et al., 2014). Accordingly, there remains a significant need in the art to develop vaccines or vaccination strategies that prevent infections with NTS bacteria.

In light of the prior art, there remains a significant need to provide means for improved treatment of diseases associated with pathogenic long-lived plasma cells as well as efficient vaccination strategies against nontyphoidal *Salmonella* (NTS).

SUMMARY

In light of the prior art, the technical problem underlying the present invention is to provide alternative and/or improved means for the treatment of diseases associated with pathogenic long-lived plasma cell. Furthermore, an efficient vaccine against nontyphoidal *Salmonella* (NTS) bacteria is highly desirable.

The technical problem underlying the present invention is solved by the features of the independent claims. Preferred embodiments of the present invention are provided by the dependent claims.

The invention therefore relates to an isolated polypeptide comprising or consisting of an amino acid sequence according to SEQ ID NO 1 (EEAEKAKEAAEKALNEAFE) or an amino acid sequence with a sequence identity of at least 70%, preferably of at least 80%, more preferably of at least 90% to SEQ ID NO 1, wherein the polypeptide is no longer than 200, preferably no longer than 170 amino acids.

The present invention is based on the surprising finding that the isolated polypeptide of the present invention can reduce the number of plasma cells in the bone marrow. The peptides of the present invention share a high sequence similarity with a conserved sequence comprised in laminin β1 in many species including humans, mice, pigs, whale, bovine, chicken and even alligator. Laminin β1 is a component of the extracellular matrix and is a member of the laminin family of extracellular matrix glycoproteins, which are a major non-collagenous constituent of basement membranes. Laminins have been implicated in a wide variety of biological processes including cell adhesion, differentiation, migration, signalling, neurite outgrowth and metastasis.

It was surprising that plasma cells, and especially long-lived IgG producing plasma cells in the bone marrow, interact with laminin β1, which is present in the bone marrow stroma and co-localizes with the bone marrow niche of long-lived plasma cells (LLPC). Upon administration of the peptides of the present invention, the number of plasma cells and especially IgG-producing LLPC in the bone marrow is reduced. Without being bound by theory, this is thought to be due to disruption of the interaction between laminin β1 and LLPC in the bone marrow niches through competition between laminin β1 and the peptides of the present invention for interaction with the plasma cells. Plasma cells can preferentially bind to the peptides of the present invention instead of binding to laminin β1, leading to the release of plasma cells from their niche and strong reduction of plasma cell numbers in the bone marrow. This reduction may be due to apoptosis and/or emigration of the plasma cells from the bone marrow.

It is a particular advantage of the peptides of the present invention that they can be used to reduce the numbers of plasma cells in the bone marrow, because bone marrow resident plasma cells and specifically LLPC are involved in many pathological processes, such as autoimmunity, allergy and development of plasma cell derived cancers. Due to their localization in protected survival niches in the bone marrow, pathogenic LLPC are refractory to immunosuppressive therapies. Similarly, plasma cell derived cancer cells can occupy these protected niches, where they are not accessible for anti-cancer therapies, such as B cell depletion and chemotherapy.

The fact that the peptides of the present invention share high sequence homology with a sequence of laminin β1, which is conserved in many species including human and many productive livestock and farm animals, such as rodents, cattle, horses, sheep, swine and galliformes, is a great advantage of the present invention, because LLPC depletion from the bone marrow can be achieved in multiple species.

Furthermore, it is advantageous that upon administration of the peptides of the present invention not only the number of LLPC in the bone marrow is reduced, but also the amount of circulating antibodies. Antibodies that are secreted by LLPC residing in the protected bone marrow niches are a major cause of autoimmune and allergic symptoms that are associated with pathogenic LLPC. Accordingly, a reduction of circulating antibodies upon administration of polypeptides of the invention leads to clinical improvements of patients suffering from such pathologies.

It was surprising that the peptides of the present invention bind specifically to plasma cells in the bone marrow and in particular to LLPC, whereas binding to plasma cells in other organs such as the spleen is less efficient. Accordingly, the peptides of the present invention do not deplete plasma cells of the spleen or other organs to the same extent as the bone marrow resident plasma cells. This is particularly advantageous, because bone marrow plasma cells and in particular LLPC are associated with autoimmune diseases, allergies, cancer and other pathologies, while plasma cells of other organs are less implicated in such conditions.

It is a further advantage of the present invention that in some embodiments the polypeptides of the invention do not have to be administered locally to the site of LLPC in the bone marrow, but can be administered systemically. Therefore, various routes of administration can be employed. Furthermore, the peptides have an unexpectedly high stability at different temperatures, which enables prolonged storage of the peptides under different storage conditions. Also, it is advantageous that the peptide is stable upon administration to a subject, so that an effect can be observed even one day or more after a single administration of a polypeptide of the present invention.

The peptides of the present invention were identified as being comprised by the *Salmonella* enterica serovar Typhimurium protein SiiE. Infection with *Salmonella* expressing SiiE can lead to a reduction of LLPC in the bone marrow and a reduction of circulating IgG antibodies. This effect can be attributed to the SiiE protein, which is expressed by *Salmonella*, since infection with SiiE deficient bacteria, which are otherwise identical, do not have this effect. It is known that SiiE is secreted by *Salmonella* and is subsequently processed. SiiE is a large protein of 5559 amino acids, with 2 distinct regions in the N- and C-terminus and 53 repeated bacterial Ig domains in between. SiiE has a high homology to a conserved region of laminin β1, which is localized in the N-terminal region of the protein (AA 1-404 of SiiE of *Salmonella* enterica serovar Typhimurium).

The most similar amino acid sequence with resepct to sequence identity between SiiE and laminin β1 is located between amino acids (AA) 136-154 of SiiE of *Salmonella* enterica serovar Typhimurium, which corresponds to SEQ ID NO:1 of the present invention. It is particularly advantageous that a polypeptide comprising or consisting of an amino acid sequence according to SEQ ID NO 1 (EEAEKAKEAAEKALNEAFE) or an amino acid sequence with a sequence identity of least 70%, preferably of at least 80%, more preferably of at least 90% to SEQ ID NO 1, wherein the polypeptide is no longer than 200, preferably no longer than 170 amino acids, can be used to reduce the number of plasma cells in the bone marrow and reduce the number of circulating IgG antibodies, because such short peptides can be easily produced through chemical or biochemical methods known to the person skilled in the art. In some cases, peptides with a length of more than 200 amino acids, comprising SEQ ID NO 1 or an amino acid sequence with a sequence identity of least 70%, preferably of at least 80%, more preferably of at least 90% to SEQ ID NO 1, did not lead to the same effect.

In a preferred embodiment, the polypeptide of the present invention comprises or consists of an amino acid sequence according to SEQ ID NO 2 (KEADKAKEEAEKAKEAAEKALNEAFEVQNSSKQIEEMLQN) or an amino acid sequence with a sequence identity of at least 70%, preferably of at least 80%, more preferably of at least 90% to SEQ ID NO 2.

The amino acid sequence corresponding to SEQ ID NO: 2, which is comprised by SiiE protein of comprised by *Salmonella* enterica serovar Typhimurium (AA 129-168) and has a high sequence homology to laminin β1, specifically reduces the number of IgG secreting plasma cells in the bone marrow and reduces the number of circulating IgG antibodies. This effect is highly specific since IgM antibodies are preferably not affected by the peptides of the present invention. Also, plasma cells of other tissues and organs than the bone marrow are preferably not affected.

According to a further preferred embodiment of the present invention, the polypeptide comprises or consists of an amino acid sequence according to SEQ ID NO 3 (SAQVEKKGNGKRRNKKEEEELKKQLDDAENAKKEAD-KAKEEAEKAKEAAEKALNEAFE-VQNSSKQIEEML-QNFL) or an amino acid sequence with a sequence identity of at least 70%, preferably of at least 80%, more preferably of at least 90% to SEQ ID NO 3.

The amino acid sequence corresponding to SEQ ID NO: 3, which is comprised by SiiE protein of comprised by *Salmonella* enterica serovar Typhimurium (AA 97-170) and has a high sequence homology to laminin β1, specifically interacts with IgG secreting plasma cells from the bone marrow, but to a much lesser extent with plasma cells from other tissues such as the spleen.

A further preferred embodiment of the present invention relates to a polypeptide comprising or consisting of an amino acid sequence according to SEQ ID NO 4 (MGNK-SIQKFFADQNSVIDLSSLGNAKGAKVSLSGPDMNITT-PRGSVIIVNGALYS-SIKGNNLAVKFKDKTITGAKIL-GSVDLKDIQLERIDSSLVDSAQVEKKGNGKRRNKK-EEEELKKQLDDAENAKKEADKAKEEAEKAKE-AAEKALNEAFEVQNSSKQIEEMLQNFL) or an amino acid sequence with a sequence identity of at least 70%, preferably of at least 80%, more preferably of at least 90% to SEQ ID NO 4.

Preferably, the polypeptide of the present invention comprises at least an amino acid sequence according to SEQ ID NO 1 (EEAEKAKEAAEKALNEAFE).

According to further preferred embodiment, the polypeptide comprises at least an amino acid sequence according to SEQ ID NO 1 (EEAEKAKEAAEKALNEAFE) or SEQ ID NO 2 (KEADKAKEEAEKAKEAAEKALNEAFE-VQNSSKQIEEMLQN).

Furthermore, the polypeptide described herein may comprise at least an amino acid sequence according to SEQ ID NO 1 (EEAEKAKEAAEKALNEAFE), SEQ ID NO 2 (KEADKAKEEAEKAKEAAEKALNEAFEVQNSSKQ-IEEMLQN), or SEQ ID NO 3 (SAQVEKKGNGKRRNK-KEEEELKKQLDDAENAKKEADKA-KEEAEKAKE A-AEKALNEAFEVQNSSKQIEEMLQNFL).

The present invention further relates to a polypeptide comprising or consisting of a polypeptide described herein for use as a medicament in the treatment of a disease associated with pathogenic long-lived plasma cells.

LLPC secrete high levels of antibodies, wherein LLPC comprise, without limitation, IgM-secreting LLPC, IgG-secreting LLPC, IgA-secreting LLPC and IgE-secreting LLPC. Furthermore, LLPC cannot switch antibody classes and cannot act as antigen-presenting cells. LLPC constitute an independent component of immunological memory. They are generated in the context of memory immune reactions and migrate to the bone marrow, where they persist for years and potentially decades. Their survival is dependent on receiving distinct signals provided by cells forming a plasma cell survival niche. Without being bound by theory, displacement of a plasma cell or long-lived plasma cell from the survival niche may result in apoptosis of the cell.

Pathogenic long-lived plasma cells are long-lived plasma cells that are involved in pathological processes such as autoimmune disease, allergies or cancerous malignancies. As a consequence of their longevity and persistence, pathogenic long-lived plasma cells can support chronic inflammatory processes in autoimmune diseases by continuously secreting pathogenic antibodies, and they can contribute to flares of symptoms. Pathogenic long-lived plasma cell as non-pathogenic plasma cells are protected in their survival niche in the bone marrow and may be refractory to immunosuppression, B cell depletion, chemotherapy and irradiation. Their elimination remains an essential therapeutic challenge.

In some embodiments it is a particular advantage of the peptides of the present invention that they can specifically reduce the number of bone marrow resident plasma cells and in particular bone marrow resident LLPC, which comprise pathogenic LLPC. Depletion of these cells might directly lead to a clinical improvement of subjects suffering from pathogenic LLPC associated diseases. Additionally, as the peptides of the present invention can lead to a displacement of pathogenic LLPC from their protected niches, the cells will become accessible to other treatment strategies, such as B cell depletion, chemotherapy, irradiation.

According to a preferred embodiment of the present invention, the disease associated with pathogenic long-lived plasma cells is multiple myeloma.

Multiple myeloma can be caused by redundant titers of antibodies generated from plasma cell myeloma in the BM. Multiple myeloma is a B cell malignancy of mature plasma cell morphology characterized by the neoplastic transformation of a single clone of plasma cells. These plasma cells proliferate in BM and may invade adjacent bone and sometimes the blood. It has already been reported that myeloma cells that reside in the bone marrow, similar to LLPC, can bind to laminin.

Accordingly, the disruption of the interaction between myeloma cells and laminin by the peptides of the present invention preferably leads to emigration of myeloma cells from their niches, which will make myeloma cells more vulnerable to be eliminated or killed, for example by apoptosis, the body's immune system and/or by further therapies that are applied to the body such as chemotherapy, B cell depletion, irradiation or other therapeutic strategies for cancer or multiple myeloma that are known to the person skilled din the art.

It is a particular advantage of the peptides of the present invention that they are specific to bone marrow resident plasma cells, so that not all plasma cells in the body of a subject that is treated by the polypeptides of the invention are depleted and no severe immuno-suppression is induced.

In a further preferred embodiment of the invention, the disease associated with pathogenic long-lived plasma cells is an auto-antibody-associated autoimmune disease.

In auto-antibody-associated autoimmune disease autoreactive LLPC continuously secrete Abs, resulting in chronicity or relapse of autoimmunity. Current therapeutic strategies primarily target the inflammatory processes and activated immune cells. Nonsteroidal anti-inflammatory drugs, antimalarials, glucocorticoids, conventional immunosuppressive or cytotoxic drugs, as well as cell depletion antibodies such as anti-CD20 (rituximab) targeting B lymphocytes can efficiently reduce the acute or chronic inflammation. They can also abrogate temporary PC survival niches in inflamed tissues and thus eliminate LLPCs in these organs. However, LLPCs in the bone marrow are typically not effectively targeted by such B cell depletion antibodies. With the peptides of the present invention it is now possible to deplete pathogenic LLPC from their remote survival niches in the bone marrow, which may lead to apoptosis or emigration of the cells from the niches, which makes them accessible to further therapeutic measures that are ineffective when the LLPC remain in their niches. Accordingly, the peptides of the present invention potentially enable a more efficient treatment of auto-antibody associated autoimmune disease in comparison to known therapeutic strategies.

Preferably, the disease associated with pathogenic long-lived plasma cells is rheumatoid arthritis (RA) and systemic lupus erythematosus (SLE).

RA and SLE are very relevant and common auto-antibody-associated autoimmune diseases and patients suffering from these diseases might in particular benefit from treatment with peptides of the present invention. In particular, the peptides of the present invention lead to a reduction of the number of autoreactive plasma cells in the bone marrow of subjects suffering from SLE.

In the context of the present invention, it is preferred that the pathogenic long-lived plasma cells are IgG-secreting plasma cells.

Most LLPC associated pathologies are mediated specifically by IgG-producing LLPC and not by LLPC that secrete other antibody classes. It is a particular advantage of the peptides of the present invention that they can specifically target IgG-secreting LLPC and not LLPC in general so that in case of an IgG-mediated LLPC associated pathology it is possible to specifically target the pathogenic cells, while LLPC that secrete for example IgM or other antibody classes are not affected.

According to a further preferred embodiment of the invention the pathogenic long-lived plasma cells preferably reside in the bone marrow. The localization of the pathogenic LLPC in the bone marrow is particularly advantageous because the peptides of the present invention specifically binding to bone marrow resident LLPC and not to LLPC in other tissues. Accordingly, the peptides only affect and/or deplete bone marrow LLPC, but not non-pathogenic LLPC or plasma cells of other tissues.

In another preferred embodiment of the invention, the pathogenic long-lived plasma cells interact with laminin β1-positive stroma cells.

It is advantageous in some embodiments to treat diseases that are associated with pathogenic LLPC that interact with laminin β1 or laminin β1-positive stroma cells, because the interaction of the LLPC with laminin β1 can be disrupted through administration of peptides of the present invention. Function and/or survival of the pathogenic LLPC may depend on the interaction with laminin β1 and therefore administration of peptides of the present invention can be detrimental for the pathogenic LLPC. The cells may be depleted, either through immigration or cell death. Also, the cells may be accessible to further treatments, such as administered drugs that directly or indirectly target pathogenic LLPC that have left their protected niches in the bone marrow upon administration of peptides of the present invention.

According to a preferred embodiment of the present invention, the treatment comprises the combined administration of said polypeptide with an anti-B cell therapy, an immunosuppressive drug or an anti-tumor chemotherapy.

According to a preferred embodiment of the present invention, the treatment comprises the combined administration of said polypeptide with an anti-B cell therapy, an immunosuppressive drug and/or an anti-tumor chemotherapy.

It is advantageous in some embodiments to combine administration of peptides of the present invention with the administration of further therapeutic measures. Such measures may comprise anti-B cell therapies, B cell depletion, anti-tumor or anti-cancer chemotherapy, immunosuppressive drugs, immunomodulatory drugs, irradiation and any further treatment options that are known to the person skilled in the art. It is known that pathogenic LLPC are protected by their specific niche in the bone marrow and are not readily accessible to the above-mentioned therapies. Administration of peptides of the present invention displaces pathogenic LLPC from their bone marrow niche and makes them accessible to the drugs and measures that can be administered in combination with polypeptides of the invention. The increased effect of these therapeutic measures on displaced pathogenic LLPC together with the lack of survival signals provided by the bone marrow niche leads to cell death and reduction or depletion of LLPC ultimately leads to an improvement of the clinical symptoms of the patient.

Furthermore, the present invention relates to a nucleic acid molecule, preferably for use as a medicament in the treatment of a disease associated with pathogenic long-lived plasma cells as described herein, wherein the nucleic acid molecule encodes a polypeptide of the present invention.

Additionally, the invention encompasses a gene therapy vector, preferably for use as a medicament in the treatment of a disease associated with pathogenic long-lived plasma cells as described herein, comprising a nucleic acid molecule of the present invention.

It can be advantageous in some embodiments to provide peptides of the present invention through administration of a nucleic acid molecule encoding a polypeptide of the present invention or through a gene therapy vector comprising a nucleic acid molecule encoding a polypeptide of the present invention. In these embodiments sustained expression of polypeptides or the present invention is possible with only a single administration. Furthermore, nucleic acids molecules and in particular DNA is very stable and can be stored for prolonged periods at room temperature without the risk of significant degradation, which is a great advantage with respect to availability.

The present invention further relates to a cell, preferably for use as a medicament in the treatment of a disease associated with pathogenic long-lived plasma cells as described herein, wherein the cell is a *Salmonella* bacterium comprising a nucleic acid region encoding a poly-peptide of the present invention, or the cell is genetically modified and comprises an exogenous nucleic acid region encoding a polypeptide of the present invention, or an exogenous nucleic acid region of the present invention, and wherein the exogenous nucleic acid region is operably linked to a promoter.

In some embodiments it is particularly advantageous to use cells or even bacteria, such as *Salmonella*, as a vehicle to deliver a nucleic acid and ultimately peptides of the present invention to a subject suffering from a disease associated with pathogenic LLPC. Administration of *Salmonella* bacteria encoding SiiE protein leads to depletion of LLPC in the bone marrow and a reduction of IgG. This shows that instead of administering a polypeptide of the present invention such peptides can be also provided through administration of cells or bacteria that provide expression of such peptides.

The present invention also relates to a pharmaceutical composition for use as a medicament in the treatment of a disease associated with pathogenic long-lived plasma cells as described herein, comprising a polypeptide of the present invention, a nucleic acid molecule a of the present invention, a gene therapy vector of the present invention and/or a cell of the present invention, and a pharmaceutically accepted carrier.

Moreover, the present invention relates to a mutant nontyphoidal *Salmonella* (NTS) bacterium for use as a vaccine in the prevention of a NTS infection in a subject, wherein the mutant NTS bacterium does not express a polypeptide comprising or consisting of a SiiE polypeptide as described herein.

This embodiment of the invention is based on the surprising finding that infection with a *Salmonella* that does not express SiiE or any other polypeptide comprising a polypeptide of the present invention, leads to a strong humoral/antibody-based immune response against *Salmonella*. This does not occur upon infection with wild-type *Salmonella* expressing SiiE. On the contrary, SiiE expressing *Salmonella* bacteria typically lead to a reduction of plasma cells in the bone marrow and a reduced IgG antibody titer. Accordingly, *Salmonella* induces an immune reaction and impairs immune memory in an SiiE-dependent manner.

SiiE deficient NTS can be used as a vaccine generating typically higher IgG antibody titers against NTS in a host, which is subsequently protected against infection with wild-type NTS expressing SiiE.

To date, vaccination against NTS, and in particular against *Salmonella* enterica serovar Typhimurium, which causes severe food poisoning in humans, cattle, swine, sheep, horses, rodents and galliformes, is not available. Furthermore, invasive strains of nontyphoidal *Salmonellae* (iNTS) have emerged as a prominent cause of bloodstream infection in African adults and children. Diseases caused by invasive nontyphoidal *Salmonella* (iNTS), including *Salmonella* enterica serovar Typhimurium, have been neglected, although the fatality rate at 20-25% is higher than that by infection with *Salmonella* enterica serovar Typhi.

In contrast, infection with *Salmonella* enterica serovar Typhi, which is restricted to humans and causes severe and often fatal typhoid fever, can be prevented by vaccination with attenuated strains, e.g. Ty21a. In the context of the present invention, it was found that *Salmonella* enterica serovar Typhi most likely does not express a functional SiiE protein comprising a polypeptide of the present invention, which, without being bound by theory, is alikely explanation of why a vaccination against *Salmonella* Typhi is available.

Preferably, the mutant NTS bacterium for use as a vaccine described herein exhibits a deletion of the SiiE encoding gene.

In a preferred embodiment of NTS bacterium for use as a vaccine, the subject is a human, galliformes, cattle, sheep, swine, horse or rodent.

Wild-type *Salmonella* mediates the inhibition of an humoral immune response through SiiE, which comprises a polypeptide of the present invention inhibiting the interaction of bone marrow plasma cells with laminin β1. This leads to a depletion of bone marrow plasma cells and a reduction of antibodies. Since laminin β1 is conserved among many species, including the species comprised by human, galliformes, cattle, sheep, swine, horse and rodent, it is in some embodiments possible to use NTS that do not express polypeptides that comprise polypeptides of the present invention as a vaccine in these species.

Preferably, the mutant NTS bacterium for use as a vaccine is a *Salmonella* enterica serovar Typhimurium.

The polypeptides of the present invention, the polypeptides for use as a medicament in the treatment of a disease associated with pathogenic long-lived plasma cells, and the mutant nontyphoidal *Salmonella* (NTS) bacterium for use as a vaccine in the prevention of a NTS infection in a subject claimed herein, are based on the same inventive concept that polypeptides of the present invention induce a reduction or depletion of plasma cells and in particular LLPC in the bone marrow, which is accompanied by a reduction of the antibody titer.

This concept can be employed in situations where a reduction of LLPC in the bone marrow and a reduction of the antibodies produced by these cells is desirable, such as in subjects suffering from diseases that are mediated by pathogenic LLPC. On the other hand, the same concept has been applied for the development of the presently claimed mutant NTS for use as a vaccine against NTS infection. In this case, a strong LLPC mediated humoral immune response is desirable to establish immune memory for NTS to prevent future infections. However, upon infection with wild-type NTS the humoral immune response and immune memory can be suppressed due to polypeptides of the present invention, such as fragments of SiiE. By using mutant NTS that do not express SiiE or a polypeptide that comprises a polypeptide of the present invention as a vaccine, for example by infecting a subject with such a mutant NTS, the immune system of said subject can generate a robust humoral immune response that results in the generation of NTS-specific LLPC that can reside for prolonged periods in the bone marrow niches.

Therefore, it can be concluded that the (1) SiiE polypeptides of the present invention and their relevance in treating diseases associated with pathogenic long-lived plasma cells, and the (2) mutant nontyphoidal *Salmonella* (NTS) bacterium that does not express a SiiE polypeptide as described herein and their relevance as a vaccine in the prevention of a NTS infection in a subject, as claimed herein, are based on a single technical concept, which enables solutions for providing alternative and/or improved means for the treatment of diseases associated with pathogenic long-lived plasma cell as well as the provision of an efficient vaccine against nontyphoidal *Salmonella* (NTS) bacteria. A special technical feature linking these aspects of the invention can be phrased as the function of SiiE protein as described herein on long-lived plasma cells, namely that polypeptides of the present invention induce a reduction or depletion of plasma cells and in particular LLPC in the bone marrow, which is accompanied by a reduction of the antibody titer. The functional connection between SiiE protein and long-lived plasma cells is directly relevant for both the therapeutic use of the SiiE protein and the absence of the SiiE protein in mutant nontyphoidal *Salmonella* (NTS) bacterium for use as a vaccine in the prevention of a NTS infection in a subject, as both embodiments are based on the effect of SiiE on plasma cells. No suggestion is evident in the prior art of the relationship between SiiE and plasma cells, and therefore the two aspects of the invention described above are linked by a unique and unitary functional feature.

Accordingly, the claimed polypeptide of the present invention, the claimed use of the polypeptide of the present invention as well as the claimed use of the mutant NTS that do not express a polypeptide that comprises a polypeptide of the present invention are all based on the common concept that polypeptides of the present invention induce a depletion of LLPC from the bone marrow.

BRIEF DESCRIPTION OF THE DRAWINGS

The invention is further described by the following figures. These are not intended to limit the scope of the invention, but represent preferred embodiments of aspects of the invention provided for greater illustration of the invention described herein.

DETAILED DESCRIPTION

Figure 1:
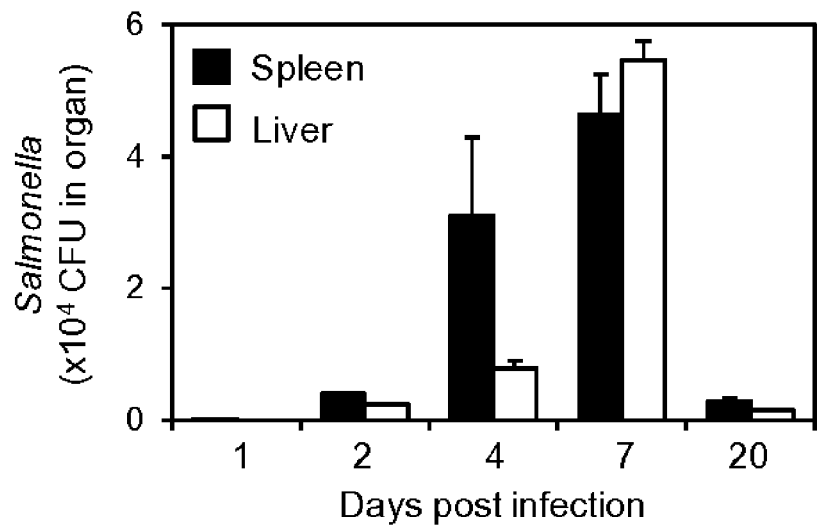
FIG. 1. *Salmonella* expands in the spleen and liver. C57BL/6 mice were infected i.p. with $10^4$ CFU of attenuated *Salmonella* and were sacrificed on the days indicated. *Salmonella* in the spleen and liver was counted. The data are representative of two independent experiments. n=3-6.

All cited documents of the patent and non-patent literature are hereby incorporated by reference in their entirety.

Amino acid sequences of preferred polypeptides of the present invention are listed under Table 1.

TABLE 1

| Amino acid sequences of preferred neuregulin proteins | |
|---|---|
| SEQ ID NO 1:<br>Amino acid (AA) sequence of AA 136-154 of SiiE (large repetitive protein SiiE [*Salmonella enterica* subsp. *enterica* serovar *Typhimurium*]; GenBank: ASF67203.1 | EEAEKAKEAAEKALNEAFE |
| SEQ ID NO 2:<br>Amino acid (AA) sequence of AA 129-168 of SiiE (large repetitive protein SiiE [*Salmonella enterica* subsp. *enterica* serovar *Typhimurium*]; GenBank: ASF67203.1 | KEADKAKEEAEKAKEAAEKALNEAFEVQNSSKQIEEMLQN |
| SEQ ID NO 3:<br>Amino acid (AA) sequence of AA 97-170 of SiiE (large repetitive protein SiiE [*Salmonella enterica* subsp. *enterica* serovar *Typhimurium*]; GenBank: ASF67203.1 | SAQVEKKGNGKRRNKKEEEELKKQLDDAENAKKEADKAKEEAE<br>KAKEAAEKALNEAFEVQNSSKQIEEMLQNFL |
| SEQ ID NO 4:<br>Amino acid (AA) sequence of AA 1-170 of SiiE (large repetitive protein SiiE [*Salmonella enterica* subsp. *enterica* serovar *Typhimurium*]; GenBank: ASF67203.1 | MGNKSIQKFFADQNSVIDLSSLGNAKGAKVSLSGPDMNITTPRGS<br>VIIVNGALYSSIKGNNLAVKFKDKTITGAKILGSVDLKDIQLERIDSS<br>LVDSAQVEKKGNGKRRNKKEEEELKKQLDDAENAKKEADKAKE<br>EAEKAKEAAEKALNEAFEVQNSSKQIEEMLQNFL |

TABLE 1-continued

Amino acid sequences of preferred neuregulin proteins

| | |
|---|---|
| SEQ ID NO 5: Full length SiiE (AA 1-5559) (large repetitive protein SiiE [*Salmonella enterica* subsp. *enterica serovar Typhimurium*]; GenBank: ASF67203.1 | MGNKSIQKFFADQNSVIDLSSLGNAKGAKVSLSGPDMNITTPRGS<br>VIIVNGALYSSIKGNNLAVKFKDKTITGAKILGSVDLKDIQLERIDSS<br>LVDSAQVEKKGNGKRRNKKEEEELKKQLDDAENAKKEADKAKE<br>EAEKAKEAAEKALNEAFEVQNSSKQIEEMLQNFLADNVAKDNLA<br>QQSDASQQNTQAKATQASKQNDAEKVLPQPINKNTSTGKSNSS<br>KNEENKLDAESVKEPLKVTLALAAESNSGSKDDSITNFTKPQFVG<br>STAPNATVIIKINGIAVGQAVADSLGNFTFTAPETLTDGTYNLEAEA<br>KTADGSGSAKLVITIDSVTDKPTFELSPESSVSGHKGLTPTLTPSI<br>VGTAEENAKVDIYVDNKLVASVDVDKDGNWSYEFKDNELSEGEN<br>SIKVVAVDKAGNKNETTDSIITDTIAPEKPTIELDDSSDSGIKNDNIT<br>NSTLPTFIGVAEPGSTVSIYLGLKHLGEVIVAKDGTWSYTLTTPLK<br>DGEYNITATATDIAGHTSATANLPFTIDTRISYFSAEIETTNDSGIV<br>GDNVTNNTRPTFTGKTEPNAIISVINSETGEEVIFKANDKGEWTFN<br>FTSDSVEGINNLTFTVEDVAGNKKDFSFSYVIDTIAPVPPTVSLED<br>YVVLPNGIILSGNDLPALVGTAEPKSTILLMRDGKLYDSIEVDSNG<br>TWNYQFSNKFLQGAYDIEIISQDAAGNKSSTVKYSFTIQTEVVPPK<br>AELDASDDSGAKGDWITNKHNALTLLGTADRFATVNILIDGKTIGV<br>TTADADGNWNFDISRNLSDNVYKITVESIDPLGRTSSVDYQLTIDS<br>FTPIPTVMLHDSADSGVKGDMITKINTPLFTGMAEANAKVSIYVDG<br>VLSGEAIAGDDGVWNFQFTTALSDGSHDVTVKVEDIAGNTASSS<br>AYNFQIVTQTQKPTIELVNDTGVDNTDHIINEKNPALTGTAAPYST<br>VKLYIDGALIAEVRTNKDGRWEYTLKADQGLVDGDHRITASVEDI<br>AGNIAHSDPFLISVDTAISIPIVSLSPDSDSGISDDNLTNIVKPTLHL<br>KDIDPDIISVQVWDAMSDTQIGVATQQPDGSWAYTFTSDLTEGLH<br>QVYVKVEDIAGNKANSAIFDFTIDTTVSTPVISLLSKDDTGVTGDN<br>LTNINKPGFAISGVDADAHRVVVQVMHNGVSEEIELSHLNGSWLF<br>IPGNTWADGSYTLTVKVEDKAGNTNYSAPLTVVIDTQIAIDGVELV<br>NDSGVKGDNMTNDDRPHFRVTVPTDVNEVRLSIDGGNSWVQAT<br>PGVAGSWEYIWPTDLADGQYTLTVEATDKAGNTVTKTIDFAVDT<br>TLSVPVIVLDSADDTGIQGDNMTNSTQPTFALQHIDDDAVRVTVS<br>VEHGGVTTTFDATKGTGGWTFTPPTSWADGDYTLSVSVEDKAG<br>NTSHSASLTVTVDTQIAINNIELVNDSGIPDDNLTNNVRPHFQVTV<br>PTDVNVVRLSIDGGKTWFNATQSATPGVWDYIWPDDVADGGYT<br>LTVEATDEAGNKATQTLDFTIDTTLSVPTLSLDSADDSGIAGDNIT<br>NVKTPGFTLNNIDTDVSRVIVEVMHNGIKQEVPLVQTGGQWRFA<br>PTSDWADGDYILTVKVEDRAGNVKQSAPLTVTVDTHIAIDRIELVN<br>DSGIPGDNLTNEARPHFQVTVPADVNGVRLSIDGGKTWFDATQS<br>ATSGVWDYTWLTNVANGPHTLMVEASDKAGNKTTQKLDFTIDTI<br>LSEPTITLDSADDSAAGDNITNVKMPGFTLGNIDADVTKVVVTVAH<br>DGKNQQIELIKNGGVWRFTPGAAWTDGDYTLTVKVEDKAGNTN<br>YSAPLTVTIDTQTSIDRIELLNDTGIVGDNLTNEARPQFHITVPTDV<br>NSVQLSLDGGINWVNATLTSDGVWEYIWPTDLVENTYTLTVKAT<br>DVAGNTATETLNFIIDTTLSTPTITLDSADDSGTANDNKTNVKTPG<br>FIIGGIDSDVTQVVVQVMRDGHSEEVELTQTNGQWRFVPGSAWT<br>DGDYTLTVTVKDEAGNIRHSAPLTVTIDTQITIDHIELVNDSGIPDD<br>NLTNNVRPHFQVTVPTDVNVVRLSIDGGKTWFNATQSATPGVW<br>DYTWLADVGEGKHTLTVEATDKAGNKTTQQLDFIIDTLLSEPTIVL<br>DSTDDSGTKGDHLTNVNKPTFLLGNIDADARYVTVEVQHGGTKE<br>VLTATKDATGNWSVTPTGTWADGDYTLTVRVEDEAGNEKHSAS<br>LTVTVDTQITIDVIELVNDNGIPGDNMTNDAHPQFRVTVPGDVNE<br>VSLSIDGGVTWVKATQSATPGVWNYTWPGTVPDGDYTLNVKAT<br>DNAGNTVTETLHFTIDTTLSTPVIVLDSADDSGVHGDNMTNHTQP<br>TFALQHIDDDAVRVTVSVEHGGVTTTFDATKDAGGWTFTPTGAW<br>ADGDYTLSVSVEDKAGNTSHSASLTVTVDTQIAINNIELVNDSGIP<br>DDNLTNNVRPHFQVTVPTDVNVVRLSIDGGKTWFNATQSATPGV<br>WDYTWLADVGEGKHTLTVEATDKAGNKTTQQLDFIIDTLLSEPTI<br>VLDNTDDSGTKGDNLTNVNKPTFLLGNIDADARYVTVEVQHGGT<br>KEVLTATKGATGIWSVTPTGTWADGDYTLTVRVEDDAGNVKYSA<br>PLTVTVDTQITIDVIELVNDNGIPGDNLTNDVRPHFRVTVPGDVNE<br>VRLSIDGGNTWVRATQGTAGIWDYTWPKDVTDGLHTLTVEATDK<br>AGNKTTQTLDFTIDTRLSTPTIAMDSRDDTGAIGDHITSVKRPGFTI<br>GNIDADAHSVILRITQGGNSQEVTLTQVGGQWRFTPDADWADG<br>SYTLTVEVTDNAGNVRQSTPLVVTVDTQTSITDITLVNDHGVPDD<br>NLTNSTRPQFEITVPADVNSVQLSIDGGANWVSATQGIEGVWGY<br>TWPTDMGDGKHTLTVMVTDRAGNTATQTLEFFIDTRLSTPTIALD<br>STDDTGTPGDDMTNRTRPTFILQNIDSDVINVTVSVTHNGTTTSF<br>TATQGAGGWSFTPPAPWGDGDYTLTVTVEDRAGNTRPSTPLTV<br>TVDTQIAIDRIELVNDSGVPGDNVTKHVRPQFQISVPDDVEKVLLS<br>IDGGTTWVTAIKSSTAGIWDYTWPTDMPEGQHTLTVEVTDGAGN<br>KMTETLNFTIDITLLTPTIELAPDQDTGQNKNDNLTSVTQPVFVLG<br>SIDKDVRHVELSIEHNGTFKTVVLTESADGWRYRPDSALADGSYT<br>FTVTVTDVAGNQQTSAPLKVTIDGTLTTPVIELAAGEDSGTVGDR<br>LTNHDRPVFDIHQVDSDVTRVMVKVTYNGKTHEEEAAVFTNGQW<br>RFTPSASWADGSYQLAVVVEDLAGNVKESAPFEVRIDTTTTINNI<br>VLLNDTGVQNDQLTNVAKPSFRIDVPGDVVQVRVTLDGGANWN<br>VIRKNADGQWIFDSPNTLVDGTYTLRVEATDEAGNIANKDLVFNI<br>DTNIQVPTIALDAGQDTGANTADNITNISRPTFTIGNVDPDVIKVVV |

TABLE 1-continued

Amino acid sequences of preferred neuregulin proteins

| | |
|---|---|
| | TIDGHDYNATKVGAGWQFTPGNAIPDGSYNITVTVEDKAGNTAT<br>SKPLPVVIDTTAEIESVTLVTDSGDSDVDNITKVDKPQFSIVTADDI<br>THVRVKIDNAANWIELTKGGDGRWIFNVGSALPDGQHTLLVDVT<br>DIAGNVAQETLQFTIDTTLREPTIVLDPTHDTGDDTNDNLTRINKP<br>VFIIGNVDNDVSHIVVHIDGRDYTIENTGGNLTFTPDQPLSDGQHT<br>ISVTVTDIAGNTKTSAELRIEIDTQVQIDSVTLTTDSGVNDHDNVTN<br>ATRPSFEIATPDDVTSVLVSFDGVNWTPISKNAAGQWEFTAGSA<br>LPDGHYTLHVQATDRAGNTANSTLGFTVDTQIDGLSVVMLDDAG<br>KDSTDGITNITSPRFEISAREPLQSVTVILNGKSSTLTQGAGNKWL<br>FTPDTPLVDGTYKIEIVAEDIAGNKISKEVSFTIDTIVSDPSIDLLDA<br>DDTGESAVDNITSVTTPRFVIGNVPADIDTVVIRINGVSYPVTANG<br>NNLWEFQVPVALNDGVYEAVVVFRDIAGNTSETKLPFTIDTTTSV<br>SVRMEPASDTGNSNSDNLTNKQNPKFEGTAEPNAKLVITIVDDKS<br>GREVLKQTITVGADGNWSVTPNILPDGMYTINVVATDVAGNTAQ<br>TQERFTIDTVTIDPTIRLSDPSIDDQHEATSLRPEFKGFAEAFSTIMI<br>QWDGKVVGSANANANGEWSWTPPSVLAPGSYVVSIVAKDKAG<br>NESSQVDFPVVIPVIDVTPPTIKLSEESDSGALGDFTTNNKTPTLIG<br>STLPNTIVSIYVDGVKVGEATADTAGRYTFQLSEMKDGHYVVQV<br>GIVNPRDNSELRSTAVDVTIDTEVAELVWNISGMHEGGYINTVTP<br>EIGGTSEPNSKITIFVNGVEKAIAYTTGAGHWGVVLPALGNDGNY<br>ELTFKVEDVAGNIREFGPQNVILDTVISPLTVVLREADDSGKVGD<br>WITNKSHVTIDGTAEAGSTLTIRNPQGVVIATLVVGNDGRWSAEL<br>DLREGSNAFVVVSEDKAGNSQQKEILIEHDTQIEISDISLSRDTNS<br>GDKYDLITNNKSPVLVAMTDPGATVQVYINGVLQGTVEASSSGNI<br>SYTMPANSADGEYQVQFVATDTAGNRVESAITTVTIDSQIAVFDID<br>EDSLPALSNNRALSVSGVGEAGSQVSIFVDGKLVNVVMVEADGT<br>WRAPILLQDDGTFNIHFSITDVAGNTEVSKDYSVDVDSSTDFPTL<br>NLEDASNSGSLDDLITNHNKPVLVGTAEAGATIHIYVDEKIVANVL<br>VLEDGTWSYQFDNALKDGEYSIRVVAEDPAGNTAESPRLLVTIDT<br>STFIDNPAMVAGSDNGIFSNDSITSQTRPTFSIFGEMNQSVQIFID<br>GVLVDTITVTDRNQVYRPESPLGDGSHSIYYVITDKAGNTATSKTL<br>NFTIDTFNTTPVAIDSIGGQTLAEMTGSDGKIYITDTTRNLLFSGSA<br>EPNSKIEIIINGLNVGEVWVNEKGHWQMPVNPLYFTEGQLDITVK<br>STDRAGNVNQEKYSIWVDTHIKVFTSELDDNKSSSKTEWWSNSD<br>LITMRGTGEIGATVSLIVAGVTLATAVVAATGRWELSTDKLPEGTY<br>DISLVIEDSAGNRWEDVREIFIDRTPPNAPVVTYSDIVNDLIIMQGT<br>AEAKSQLIITDSEGNTYTLTVPDNGKWSMAIPYPSEGKFTITSVDA<br>IGNRSDDVPLDIMKEVPVISLSPDSDSGTVGDNITRDKQPTFIIGNL<br>ESDVVVVQVDINGTVYNAEKNADGVWFFTPGTPLADGSYTISVIA<br>SDAAGNQKNSLPITVTIDSTLTVPEIALAAGEDNGASDSDNVTNH<br>TQPKFTLQHIDADVTGVTVNVTHNGVTDIYQATQGADGWTFTPP<br>AAWNDGNYTLSVTVVDRAGNSQQSASLAVTVDSTVTVTADSQH<br>DDASDDATATAVTPPESETVNAESATHLRTEPSAAEESVVKVTA<br>YSITLLNADSGDEIDRSISQTPSFEISVPENIVNVSIMFEGEEFTLPI<br>TNQKAIFEVPLSLEDGEYTMDVKFIDKDNDFLIKEKTFSVDHSSAD<br>IVNAMNVRGKTEDDINDSPSTSSVGHNNNGAIDVFAVNEVTLPVD<br>NQEEHA |
| SEQ ID NO 6: mouse<br>Laminin β1; AA 1638-1681;<br>NCBI Reference Sequence:<br>NP_032508.2 | VTADMVKEALEEAEKAQVAAEKAIKQADEDIQGTQNLLTSIESE |
| SEQ ID NO 7: human<br>Laminin β1; AA 1590-1633;<br>GenBank: EAL24388.1 | VTADMVKEALEEAEKAQVAAEKAIKQADEDIQGTQNLLTSIESE |
| SEQ ID NO 8: N-terminal<br>domain of SiiE (AA 1-404)<br>(large repetitive protein SiiE<br>[Salmonella enterica subsp.<br>enterica serovar<br>Typhimurium]; GenBank:<br>ASF67203.1 | MGNKSIQKFFADQNSVIDLSSLGNAKGAKVSLSGPDMNITTPRGS<br>VIIVNGALYSSIKGNNLAVKFKDKTITGAKILGSVDLKDIQLERIDSS<br>LVDSAQVEKKGNGKRRNKKEEEELKKQLDDAENAKKEADKAKE<br>EAEKAKEAAEKALNEAFEVQNSSKQIEEMLQNFLADNVAKDNLA<br>QQSDASQQNTQAKATQASKQNDAEKVLPQPINKNTSTGKSNSS<br>KNEENKLDAESVKEPLKVTLALAAESNSGSKDDSITNFTKPQFVG<br>STAPNATVIIKINGIAVGQAVADSLGNFTFTAPETLTDGTYNLEAEA<br>KTADGSGSAKLVITIDSVTDKPTFELSPESSVSGHKGLTPTLTPSI<br>VGTAEENAKVDIYVDNKLVASVDVDKDGNWSYEFKDNELSEGE |

In one embodiment the invention therefore encompasses a polypeptide as described herein comprising or consisting of an amino acid sequence selected from the group consisting of:

a) an amino acid sequence comprising or consisting of an amino acid sequence according to SEQ ID NO 1-4; wherein the polypeptide is preferably no longer than 200, preferably no longer than 170 amino acids;

b) an amino acid sequence comprising or consisting of an amino acid sequence according to SEQ ID NO 1-4, wherein the length of the amino acid molecule is between 10 and 300 amino acids, preferably between 15 and 200 amino acids, most preferably between 19 and 170 amino acids, wherein the surrounding sequences are preferably provided as SiiE sequences flanking the amino acid sequences according to SEQ ID NO 1-4.

c) an amino acid sequence having sufficient sequence identity to be functionally analogous/equivalent to an amino acid sequence according to a), comprising preferably a sequence identity to an amino acid sequence according to a) of at least 70%, 80%, preferably 90%, more preferably 95%; and d) an amino acid sequence of a), b) or c) which is modified by deletions, additions, substitutions, translocations, inversions and/or insertions and functionally analogous/equivalent to an amino acid sequence according to a), b) or c).

Functionally analogous sequences refer preferably to the ability to encode a functional peptide comprising a homology to a conserved sequence of laminin β1. Preferably, the conserved sequence of laminin β1 corresponds to an amino acid sequence according to SEQ ID NO 6 or 7.

In this context, functionality may refer to the ability of a peptide to interfere with or inhibit the interaction between long-live plasma cells and laminin β1 in the bone marrow.

Embodiments of the invention may comprise a polypeptide as described herein comprising or consisting of an amino acid sequence SEQ ID NO 1-4, or variants of these sequences, wherein the sequence variant may comprise a sequence identity to SEQ ID NO 1-4 of 50, 55, 60, 65, 70, 75, 80, 81, 82, 83, 84, 85, 86, 87, 88, 89, 90, 91, 92, 93, 94, 95, 96, 97, 98 or 99%. Sequence identity may be determined using methods known to one skilled in the art, such as BLAST or other sequence alignment tools.

In further preferred embodiments, the invention relates to a polypeptide comprising or consisting of an amino acid sequence derived from the N-terminal domain of *Salmonella* enterica serovar Typhimurium SiiE protein. Preferably, the amino acid sequence derived from the N-terminal domain of *Salmonella* enterica serovar Typhimurium SiiE protein comprises or consists of an amino acid sequence homologous to a conserved amino acid sequence of laminin β1. Preferably, the conserved amino acid sequence of laminin β1 has a length of at least 19 amino acids, more preferably 25 amino acids, most preferably 40 amino acids. Sequence homology refers to a sequence identity of more than 65%, preferably more than 70%. The N-terminal domain of of *Salmonella* enterica serovar Typhimurium SiiE protein comprises the amino acids 1-404 of SiiE protein.

SiiE is a large protein of 5,559 amino acids or *Salmonella* enterica serovar Typhimurium, with 2 distinct regions in the N- and C-terminus and 53 repeated bacterial Ig domains in between (FIG. 6). SiiE is secreted and is involved in the adhesion to gut intestinal epithelial cells (Gerlach et al., 2007).

Protein modifications to the polypeptides of the present invention, which may occur through substitutions in amino acid sequence, and nucleic acid sequences encoding such molecules, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein. In some embodiments this amendment will not significantly alter the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, lie and Leu; the non-polar aromatic amino acids Phe, Trp and Tyr; the neutral polar amino acids Ser, Thr, Cys, Gin, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups.

The present invention encompasses gene therapy comprising the administration of a therapeutic gene encoding the polypeptide described herein.

The term gene therapy preferably refers to the transfer of DNA into a subject in order to treat a disease. The person skilled in the art knows strategies to perform gene therapy using gene therapy vectors. Such gene therapy vectors are optimized to deliver foreign DNA into the host cells of the subject. In a preferred embodiment the gene therapy vectors may be a viral vector. Viruses have naturally developed strategies to incorporate DNA in to the genome of host cells and may therefore be advantageously used. Preferred viral gene therapy vectors may include but are not limited to retroviral vectors such as moloney murine leukemia virus (MMLV), adenoviral vectors, lentiviral, adenovirus-associated viral (AAV) vectors, pox virus vectors, herpes simplex virus vectors or human immunodeficiency virus vectors (HIV-1). However also non-viral vectors may be preferably used for the gene therapy such as plasmid DNA expression vectors driven by eukaryotic promoters or liposomes encapsulating the transfer DNA. Furthermore preferred gene therapy vectors may also refer to methods to transfer of the DNA such as electroporation or direct injection of nucleic acids into the subject. Moreover it may be preferred that the gene therapy vectors for example a viral gene therapy vector is adapted to target bone marrow cells and in particular stroma cells, hematopoietic cells or immune cells of the bone marrow or long-lived plasma cells. To this end the viral capsid may be conjugated with ligands binding to bone marrow cells and in particular stroma cells, hematopoietic cells or immune cells of the bone marrow or long-lived plasma cells such as monoclonal antibodies. It may also be preferred that the viral gene therapy vectors are genetically modified using inducible promoters or promoters that are specific for bone marrow cells and in particular stroma cells, hematopoietic cells or immune cells of the bone marrow or long-lived plasma cells to enhance the expression of the nucleic acid specifically within the bone marrow in the surrounding of pathogenic long-lived plasma cells. Preferred gene therapy vectors may therefore comprise vectors for an inducible or conditional expression of the polypeptides. The person skilled in the art knows how to choose preferred gene therapy vectors according the need of application as well as the methods on how to implement the nucleic acid into the gene therapy vector. (P. Seth et al., 2005, N. Koostra et, al. 2009., W. Walther et al. 2000, Waehler et al. 2007).

The nucleic acid according to the invention and preferred embodiments thereof, in particular a nucleic acid encoding a polypeptide of the present invention, is particularly efficient for gene therapy due to a high therapeutic potential at a small size. This ensures a stable integration at high expression levels over extended periods of times.

In a further preferred embodiment the invention relates to a cell for use as a medicament in the treatment of a disease associated with pathogenic long-lived plasma cells as described herein, wherein the cell is genetically modified and comprises an exogenous nucleic acid region encoding for a polypeptide according to the invention or preferred embodiments thereof and wherein the exogenous nucleic acid region is operably linked to a promoter.

The person skilled in the art knows how to genetically modify cells in order to express the polypeptides according to the inventions. Advantageously by expressing the therapeutically effective polypeptides the cells may act as bio pump or drug factory that continuously expresses and provides the polypeptides to the subject. Thereby the amount of the polypeptides can be held at a therapeutic level over long periods. The person skilled in the art knows which cells may be preferably used to this end. In a preferred embodiment the cells are stem cells, characterized by a stable expression of the polypeptides. Stem cells may include but are not limited to, embryonic stem cells such as early embryonic stem cells and blastocyst embryonic stem cells; fetal stem cells; umbilical cord stem cells; and adult stem cells such as mesenchymal stem cells, hematopoietic stem cells, endothelial stem cells, peripheral blood stem cells, and multipotent somatic stem cells.

In another preferred embodiment the cell may be a bacterial cell or a bacterium. Bacteria constitute a large domain of prokaryotic single cell microorganisms, which can be genetically modified by standard microbiology and molecular biology techniques. Besides naturally occurring bacteria, there a genetically modified bacteria and synthetic bacteria. A person skilled in the art is able to select preferably bacterial cells that may be used in the context of the present invention.

Preferably, the bacterial cell is a *Salmonella* bacterium. *Salmonella* bacteria are gram-negative bacteria of the Enterobacteriaceae family. The genus of *Salmonella* bacteria comprises two species, *Salmonella* bongori and *Salmonella* enterica, the latter of which is divided into six subspecies (S. e. enterica, S. e. salamae, S. e. arizonae, S. e. diarizonae, S. e. houtenae, and S. e. indica), which contain more than 2500 serotypes (also serovars) defined on the basis of the somatic O (lipopolysaccharide) and flagellar H antigens. The full name of a serotype is given as, for example, *Salmonella* enterica subsp. enterica serotype Typhimurium, but can be abbreviated to *Salmonella* Typhimurium. Further differentiation of strains to assist clinical and epidemiological investigation may be achieved by antibiotic sensitivity testing and by other molecular biology techniques such as pulsed-field gel electrophoresis, multilocus sequence typing, and, increasingly, whole genome sequencing. Historically, Salmonellae have been clinically categorized as invasive (typhoidal) or noninvasive (nontyphoidal Salmonellae) based on host preference and disease manifestations in humans. A person skilled in the art can select suitable *Salmonella* bacterium that may be genetically modified or not that comprises a nucleic acid region encoding a polypeptide of the present invention.

The cells may migrate to the site of the pathogenic long-lived plasma cells in order to locally express the polypeptides in vicinity of the pathogenic cells. Advantageously the cells may however also be transplanted at a different location as the polypeptides can also be transported by the vascular system throughout the body of the subject. Local administration of the cells e.g. by a subcutaneous injection may therefore contribute in a systemic manner largely irrespective of the location of the cells within the body of the subject.

In a further preferred embodiment the cells for use as a medicament as described herein is characterized by introducing a therapeutically effective number of said cells to a subject within a biocompatible matrix. Preferred materials for the biocompatible matrix are agarose, carrageenan, alginate, chitosan, gellan gum, hyaluronic acid, collagen, cellulose and its derivatives, gelatin, elastin, epoxy resin, photo cross-linkable resins, polyacrylamide, polyester, polystyrene and polyurethane or polyethylene glycol (PEG). It is further preferred that the biocompatible matrix is a semi-permeable hydrogel matrix and the cells are entrapped by said matrix. Advantageously the biocompatible matrix allows for an efficient diffusion of nutrients, oxygens and other biomolecules to ensure a long lasting viability of the cells expressing the polypeptide, while immobilizing the cells. Thereby the cells can be concentrated at preferred locations within the subject. For instance the cells can be transplanted subcutaneously and/or in proximity of diseased regions of the subject i.e. close to a vestibular schwannoma. It is surprising that by introducing encapsulated cells, the cells function particularly efficiently as bio pumps and provide a high level of therapeutic polypeptides to the subject.

In a preferred embodiment the invention further relate to pharmaceutical composition for use as a medicament in the treatment of a disease associated with pathogenic long-lived plasma cells as described herein, wherein the pharmaceutical composition comprises the polypeptide, the nucleic acid, the gene therapy vector and/or the cell, and optionally a pharmaceutically accepted carrier. Preferably the pharmaceutical composition is administered to the subject at a therapeutically effective amount at any administration route as described herein.

In a preferred embodiment the pharmaceutical composition for use as a medicament as described herein is administered by introducing a therapeutically effective amount of the composition into the blood stream of a subject. This route of administration is particularly advantageous for an administration of the polypeptides.

In a further preferred embodiment the pharmaceutical composition for use as a medicament as described herein is administered locally. It is particularly preferred that the pharmaceutical composition is administered locally to the site of the pathogenic long-lived plasma cells, such as the bone marrow. It may also be preferred that the local administration of the pharmaceutical composition to the bone marrow is achieved by injecting the polypeptide or the pharmaceutical composition of the present invention.

Moreover in a preferred embodiment the local administration of the polypeptides may be preferably mediated by an implant such as a collagen sponge. To this end it may be preferred to soak the sponge in a pharmaceutical composition comprising the polypeptides and implant the sponge close to the site of the pathogenic long-lived plasma cells. By doing so the polypeptides advantageously diffuse locally and can therefore act site specifically.

In further preferred embodiment the polypeptides may be locally administered by means of a hydrogel. Hydrogels are three-dimensional, cross-linked networks of water-soluble polymers. The person skilled in the art knows how to produce suitable hydrogels for the delivery of proteins or polypeptides (Hoare et al. 2008, Peppas et al. 2000, Hoffmann A. et al. 2012). In particular the density of the cross-linked network of the hydrogel may be advantageously optimized to achieve a porosity suited to load the polypeptides into the hydrogel. Subsequently the release of the polypeptides is governed by the diffusion of the peptides throughout the gel network. Therefore the release rate and thus the therapeutically effective amount of the polypeptides can be precisely tuned by optimizing the cross-linking density of the hydrogel. Moreover preferred hydrogels may also encompass an outer membrane optimized for the release of the polypeptides. The preferred hydrogels are biocompatible and are preferably implanted for a long term local supply of the polypeptides. In preferred embodiments the hydrogels may be implanted subcutaneously at or close to the site of the pathogenic long-lived plasma cells. Transdermal administration of the polypeptides by use of hydrogels may also be envisioned. By means hydrogels a therapeutically effective dose of polypeptides can be advantageously localized to the site of the pathogenic long-lived plasma cells, while minimizing the systemic dosage. Thereby a long term administration can be achieved with a sustained and site specific release and minimized side effects.

As used herein, "nucleic acid" shall mean any nucleic acid molecule, including, without limitation, DNA, RNA and hybrids or modified variants thereof. An "exogenous nucleic acid" or "exogenous genetic element" relates to any nucleic acid introduced into the cell, which is not a component of the cells "original" or "natural" genome. Exogenous nucleic acids may be integrated or non-integrated, or relate to stably transfected nucleic acids.

As used herein, "polypeptide" shall mean both peptides and proteins. In this invention, the polypeptides may be naturally occurring or recombinant (i.e., produced via recombinant DNA technology), and may contain mutations (e.g., point, insertion and deletion mutations) as well as other covalent modifications (e.g., glycosylation and labelling (via biotin, streptavidin, fluorescein, and radioisotopes)) or other molecular bonds to additional components. For example, PEGylate proteins are encompassed by the scope of the present invention. PEGylation has been widely used as a post-production modification methodology for improving biomedical efficacy and physicochemical properties of therapeutic proteins. Applicability and safety of this technology have been proven by use of various PEGylated pharmaceuticals for many years (refer Jevsevar et al, Biotechnol J. 2010 Jan;5(1):113-28). In some embodiments the polypeptides described herein are modified to exhibit longer in vivo half-lives and resist degradation when compared to unmodified polypeptides. Such modifications are known to a skilled person, such as cyclized polypeptides, polypeptides fused to Vitamin B12, stapled peptides, protein lipidization and the substitution of natural L-amino acids with D-amino acids (refer Bruno et al, Ther Deliv. 2013 Nov; 4(11): 1443-1467).

In some embodiments of the invention the peptide, preferably according to sequences disclosed herein, may comprise a 0 to 10 amino acid addition or deletion at the N and/or C terminus of a sequence.

As used herein the term "a 0 to 10 amino acid addition or deletion at the N and/or C terminus of a sequence" means that the polypeptide may have a) 0, 1, 2, 3, 4, 5, 6, 7, 8, 9 or 10 additional amino acids at its N terminus and 0, 1, 2, 3, 4, 5, 6, 7, 8, 9 or 10 amino acids deleted at its C terminus or b) 0, 1, 2, 3, 4, 5, 6, 7, 8, 9 or 10 additional amino acids at its C terminus and 0, 1, 2, 3, 4, 5, 6, 7, 8, 9 or 10 nucleotides deleted at its N terminus, c) 0, 1, 2, 3, 4, 5, 6, 7, 8, 9 or 10 additional amino acids at its N terminus and 0, 1, 2, 3, 4, 5, 6, 7, 8, 9 or 10 additional amino acids at its N terminus or d) 0, 1, 2, 3, 4, 5, 6, 7, 8, 9 or 10 amino acids deleted at its N terminus and 0, 1, 2, 3, 4, 5, 6, 7, 8, 9 or 10 amino acids deleted at its C terminus.

Furthermore, in addition to the polypeptides described herein, peptidomimetics are also contemplated. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) Adv. Drug Res. 15: 29; Veber and Freidinger (1985) TINS p. 392; and Evans et al. (1987) J. Med. Chem. 30: 1229) and are usually developed with the aid of computerized molecular modelling.

Peptide mimetics that are structurally similar to therapeutically useful peptides may be used to produce an equivalent therapeutic or prophylactic effect. It may be preferred in some embodiments to use peptide mimetics in order to prolong the stability of the polypeptides, when administered to a subject. To this end peptide mimetics for the polypeptides may be preferred that are not cleaved by human proteasomes.

The polypeptides, nucleic acid molecules, gene therapy vectors or cells described herein may comprise different types of carriers depending on whether they are to be administered in solid, liquid or aerosol form, and whether they need to be sterile for such routes of administration as injection.

The active agent of present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, directly, via a catheter, via a lavage, in cremes, in lipid compositions (e.g., liposomes), locally applied by sponges or by other method or any combination of the forgoing as would be known to one of ordinary skill in the art (see, for example, Remington's Pharmaceutical Sciences, 18th Ed. Mack Printing Company, 1990, incorporated herein by reference).

The present invention encompasses treatment of a patient by introducing a therapeutically effective number polypeptides, nucleic acids, gene therapy vectors or cells of the present invention into a subject's bloodstream. As used herein, "introducing" polypeptides, nucleic acids, gene therapy vectors or cells into the subject's bloodstream shall include, without limitation, introducing such polypeptides, nucleic acids, gene therapy vectors or cells into one of the subject's veins or arteries via injection. Such administering can also be performed, for example, once, a plurality of times, and/or over one or more extended periods. A single injection is preferred, but repeated injections over time (e.g., quarterly, half-yearly or yearly) may be necessary in some instances. Such administering is also preferably performed using an admixture of polypeptides, nucleic acids, gene therapy vectors or cells and a pharmaceutically acceptable carrier. Pharmaceutically acceptable carriers are well known to those skilled in the art and include, but are not limited to, 0.01-0.1 M and preferably 0.05 M phosphate buffer or 0.8% saline.

Administration may also occur locally, for example by injection into an area of the subject's body in proximity to a site where pathogenic long-lived plasma cells are localized. As used herein, in "proximity with" a tissue/site includes, for example, within 50 mm, 20 mm, 10 mm, 5 mm, within 1 mm of the tissue, within 0.5 mm of the tissue and within 0.25 mm of the tissue/site.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Additionally, such pharmaceutically acceptable carriers can be aqueous or non-aqueous solutions, suspensions, and emulsions, most preferably aqueous solutions. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringers and fixed oils. Intravenous vehicles include fluid and nutrient replenishers, electrolyte replenishers such as Ringer's dextrose, those based on Ringer's dextrose, and the like. Fluids used commonly for i.v. administration are found, for example, in Remington: The Science and Practice of Pharmacy, 20th Ed., p. 808, Lippincott Williams S-Wilkins (2000). Preservatives and other additives may also be present, such as, for example, antimicrobials, antioxidants, chelating agents, inert gases, and the like.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

As used herein, a "therapeutically effective amount" for the pharmaceutical composition includes, without limitation, the following amounts and ranges of amounts:

For a composition comprising a polypeptide according to the invention or preferred embodiment thereof: (i) from about $1\times10^{-3}$ to about $1\times10^{6}$ μg/kg body weight; (ii) from about $1\times10^{-2}$ to about $1\times10^{5}$ μg/kg body weight; (iii) from about $1\times10^{-1}$ to about $1\times10^{4}$ μg/kg body weight; (iv) from about $1\times10^{-1}$ to about $1\times10^{3}$ μg/kg body weight; (v) from about $1\times10^{-1}$ to about $1\times10^{2}$ μg/kg body weight; (vi) from about $1\times10^{-1}$ to about $0.5\times10^{2}$ μg/kg body weight; (vii) about $1\times10^{-2}$ μg/kg body weight; (viii) about $1\times10^{1}$ μg/kg body weight; (ix) about 10 μg/kg body weight (x) about $1\times10^{2}$ μg/kg body weight; (xi) about $5\times10^{3}$ μg/kg body weight.

For a composition comprising cells according to the invention or preferred embodiment thereof: (i) from about $1\times10^{2}$ to about $1\times10^{8}$ cells/kg body weight; (ii) from about $1\times10^{3}$ to about $1\times10^{7}$ cells/kg body weight; (iii) from about $1\times10^{4}$ to about $1\times10^{6}$ cells/kg body weight; (iv) from about $1\times10^{4}$ to about $1\times10^{5}$ cells/kg body weight; (v) from about $1\times10^{5}$ to about $1\times10^{6}$ cells/kg body weight; (vi) from about $5\times10^{4}$ to about $0.5\times10^{5}$ cells/kg body weight; (vii) about $1\times10^{3}$ cells/kg body weight; (viii) about $1\times10^{4}$ cells/kg body weight; (ix) about $5\times10^{4}$ cells/kg body weight; (x) about $1\times10^{5}$ cells/kg body weight; (xi) about $5\times10^{5}$ cells/kg body weight; (xii) about $1\times10^{6}$ cells/kg body weight; and (xiii) about $1\times10^{7}$ cells/kg body weight.

Human body weights envisioned include, without limitation, about 5 kg, 10 kg, 15 kg, 30 kg, 50 kg, about 60 kg; about 70 kg; about 80 kg, about 90 kg; about 100 kg, about 120 kg and about 150 kg.

Dosages of the viral gene therapy vector will depend primarily on factors such as the condition being treated, the selected gene, the age, weight and health of the patient, and may thus vary among patients. For example, a therapeutically effective human dosage of the viral vectors may be preferably in the range of from about 1 to about 1000 ml, preferably 10 to 100 ml, preferably 20 to 50 ml of saline solution containing concentrations of from about $1\times10^{5}$ to $1\times10^{12}$ preferably $1\times10^{6}$ to $1\times10^{11}$ more preferably $1\times10^{7}$ to $1\times10^{10}$ plaque forming units (pfu)/ml viruses. The dosage will be adjusted to balance the therapeutic benefit against any side effects. The levels of expression of the selected gene can be monitored to determine the selection, adjustment or frequency of dosage administration.

As used herein "inducible expression" or "conditional expression" relates to a state, multiple states or system of an expression of the polypeptide, wherein the polypeptide is preferably not expressed, or in some embodiments expressed at negligible or relatively low levels, unless there is the presence of one or more molecules (an inducer) or other set of conditions in the cell that allows for polypeptide expression. Inducible promoters may relate to either naturally occurring promoters that are expressed at a relatively higher level under particular biological conditions, or to other synthetic promoters comprising any given inducible element. Inducible promoters may refer to those induced by particular tissue- or micro-environments or combinations of biological signals present in particular tissue- or micro-environments, or to promoters induced by external factors, for example by administration of a small drug molecule or other externally applied signal.

As used herein the term "bio pump" or "drug factory" preferably describe the function of cells as a continuously producing source of the polypeptide, preferably at a therapeutically effective dosage. By administering cells to a subject particularly stable levels of the polypeptides according to the invention or preferred embodiments thereof can be provided. In the sense the bio pump, that is the cells, allow for a continuous supply that maintain levels of the polypeptides at a particular high and stable state, for example it may compensate for losses of the polypeptides for instance due to a degeneration of the polypeptides through proteasomes.

The terms "hydrogel", "gel" and the like, are preferably used interchangeably herein to refer to a material which is not a readily flowable liquid and not a solid. The term hydrogel is preferably meant to be a water insoluble, water-containing material. Examples of hydrogels include synthetic polymers such as polyhydroxyethyl methacrylate, poly(ethylene glycol) and chemically or physically crosslinked polyvinyl alcohol, polyacrylamide, poly(N-vinyl pyrolidone), polyethylene oxide, and hydrolysed polyacrylonitrile. Examples of hydrogels which are organic polymers include DNA hydrogels or covalent or ionically crosslinked polysaccharide-based hydrogels such as the polyvalent metal salts of alginate, pectin, carboxymethyl cellulose, heparin, hyaluronate and hydrogels from chitin, chitosan, pullulan, gellan and xanthan.

Plasma cells, are also called plasma B cells, plasmocytes, plasmacytes, or effector B cells. Plasma cells are white blood cells/immune cells that secrete large volumes of antibodies. Plasma cells are transported by the blood plasma and the lymphatic system and originate in the bone marrow; B cells differentiate into plasma cells that produce antibody molecules. Once released into the blood and lymph, these antibody molecules bind to the target antigen (foreign substance) and initiate its neutralization or destruction by means of the immune system. B cells can differentiate into memory B cells or plasma cells upon stimulation, mostly by T cells, which usually occurs in germinal centers of secondary lymphoid organs like the spleen and lymph nodes. Most of these B cells will become plasmablasts (or "immature plasma cells"), and eventually plasma cells, and begin producing large volumes of antibodies, while some B cells will undergo affinity maturation, which refers to the selection of antibodies with higher affinity for the antigen and the activation and growth of B cell clones able to secrete antibodies of higher affinity.

After the process of affinity maturation in germinal centers, plasma cells have an indeterminate lifespan, ranging from days to months. A specific subclass of plasma cells has been shown to reside for much longer periods in the bone marrow. This class of plasma cells is referred to as "long-lived plasma cells" (LLPC). LLPC secrete high levels of antibodies, wherein LLPC comprise, without limitation, IgM-secreting LLPC, IgG-secreting LLPC, IgA-secreting LLPC and IgE-secreting LLPC. Furthermore, LLPC cannot switch antibody classes and cannot act as antigen-presenting cells. LLPC constitute an independent component of immunological memory. They are generated in the context of memory immune reactions and migrate to the bone marrow, where they persist for years and decades. Their survival is dependent on receiving distinct signals provided by cells forming a plasma cell survival niche. Displacement of a plasma cell or long-lived plasma cell from the survival niche might result in apoptosis of the cell.

Long-lived plasma cells survive in a protected microenvironment for years or even a lifetime and provide humoral memory by establishing persistent Ab titers. The term "pathogenic long-lived plasma cell" refers to long-lived plasma cells, which may be for example autoreactive, malignant, and allergen-specific long-lived plasma cells. These pathogenic long-lived plasma cell are likewise protected in their survival niche and are refractory to immunosuppression, B cell depletion, and irradiation. Their elimination remains an essential therapeutic challenge. As a consequence of their longevity and persistence, long-lived plasma cells can support chronic inflammatory processes in autoimmune diseases by continuously secreting pathogenic antibodies, and they can contribute to flares of symptoms.

Accordingly, the term "disease associated with pathogenic long-lived plasma cells" refers to, without limitation, plasma cell associated cancerous malignancies, such as plasmacytoma, multiple myeloma, Waldenström macroglobulinemia, Lymphoplasmacytic lymphoma (LPL), POEMS syndrome/osteosclerotic myeloma, Type I and II cryoglobulinemia, Primary Amyloidosis (AL), Heavy chain disease, Monoclonal gammopathy of undetermined significance (MGUS) and plasma cell leukemia; auto-antibody associated autoimmune diseases, such as rheumatoid arthritis, systemic lupus erythematosus (SLE), chronic immune thrombocytopenia, Sjögren's syndrome, or multiple sclerosis; and allergies through, for example, LLPCs that produce allergen-specific IgE antibodies. A skilled person is aware of diseases falling under this category and furthermore can determine these disease by employing established immunologic methods to interrogate long-lived plasma cells and their pathogenicity.

According to a preferred embodiment of the invention, the pathogenic long-lived plasma cells interact with laminin β1-positive stroma cells. Laminin β1-positive stroma cells are stroma cells that can be identified as stroma cells that co-localize with laminin β1, for example in an microscopic analysis by immunofluorescence.

Laminin β1 is a member of the family of laminin proteins, which are extracellular matrix glycoproteins, which are a major noncollagenous constituent of basement membranes. They have been implicated in a variety of processes including cell adhesion, differentiation, migration, signalling and metastasis. Laminins are composed of 3 non-identical chains: laminin alpha, beta and gamma (formerly A, B1, and B2, respectively). Each laminin chain is a multidomain protein encoded by a distinct gene. Several isoforms of each chain have been described. Different alpha, beta and gamma chain isomers combine to give rise to different heterotrimeric laminin isoforms, for example the alpha1-beta1-gamma1 heterotrimer is laminin 1. The beta chain isoform laminin β1 has 7 structurally distinct domains, which it shares with other beta chain isomers. Laminin, beta 1 is expressed in most tissues that produce basement membranes, and is one of the 3 chains constituting laminin 1. A sequence in the beta 1 chain that is involved in cell attachment, chemotaxis, and binding to the laminin receptor was identified and shown to have the capacity to inhibit metastasis.

The term "stroma cells" refers to various cells types that constitute the stroma of a tissue. The stroma is the part of a tissue or organ that has a connective and structural role. It consists of all the parts, which do not carry out the specific functions of the organ, for example, connective tissue, blood vessels, nerves, ducts, etc. The other part, the parenchyma, consists of the cells that perform the function of the tissue or organ. The stroma of the bone marrow is all tissue not directly involved in the bone marrow's primary function of hematopoiesis. The stroma of the bone marrow is indirectly involved in hematopoiesis, since it provides the hematopoietic microenvironment that facilitates hematopoiesis, for example by generating factors such as colony stimulating factors, which have a significant effect on hematopoiesis. Cell types that are comprised by the bone marrow stroma include, without limitation, fibroblasts (reticular connective tissue), macrophages, adipocytes, osteoblasts, osteoclasts and endothelial cells, which form the sinusoids, and endothelial stem cells.

Multiple myeloma is a B cell malignancy of mature plasma cell morphology characterized by the neoplastic transformation of a single clone of these types of cells. These plasma cells proliferate in BM and may invade adjacent bone and sometimes the blood. Variant forms of multiple myeloma include overt multiple myeloma, smoldering multiple myeloma, plasma cell leukemia, non-secretory myeloma, IgD myeloma, osteosclerotic myeloma, solitary plasmacytoma of bone, and extramedullary Plasmacytoma.

Auto-antibody associated autoimmune diseases that can be associated with pathogenic long-lived plasma cells and are comprised the diseases associated with long-lived plasma cells is preferably selected from Takayasu Arteritis, Giant-cell arteritis, familial Mediterranean fever, Kawasaki disease, Polyarteritis nodosa, cutanous Polyarteritis nodosa, Hepatitis-associated arteritis, Behcet's syndrome, Wegener's granulomatosis, ANCA-vasculitidies, Churg-Strauss syndrome, microscopic polyangiitis, Vasculitis of connective tissue diseases, Hennoch-Schönlein purpura, Cryoglobulinemic vasculitis, Cutaneous leukocytoclastic angiitis, Tropical aortitis, Sarcoidosis, Cogan's syndrome, Wiskott-Aldrich Syndrome, Lepromatous arteritis, Primary angiitis of the CNS, Thromboangiitis obliterans, Paraneoplastic ateritis, Urticaria, Dego's disease, Myelodysplastic syndrome, Eythema elevatum diutinum, Hyperimmunoglobulin D, Allergic Rhinitis, Asthma bronchiale, chronic obstructive pulmonary disease, periodontitis, Rheumatoid Arthritis, atherosclerosis, Amyloidosis, Morbus Chron, Colitis ulcerosa, Autoimmune Myositis, Diabetes mellitus, Guillain-Barre Syndrome, histiocytosis, Osteoarthritis, atopic dermatitis, periodontitis, chronic rhinosinusitis, Psoriasis, psoriatic arthritis, Microscopic colitis, Pulmonary fibrosis, glomerulonephritis, Whipple's disease, Still's disease, erythema nodosum, otitis, cryoglobulinemia, Sjogren's syndrome, Lupus erythematosus, preferably systemic lupus erythematosus (SLE), aplastic anemia, Osteomyelofibrosis, chronic inflammatory demyelinating polyneuropathy, Kimura's disease, systemic sclerosis, chronic periaortitis, chronic prostatitis, idiopathic pulmonary fibrosis, chronic granulomatous disease, Idiopathic achalasia, bleomycin-induced lung inflammation, cytarabine-induced lung inflammation, Autoimmunthrombocytopenia, Autoimmunneutropenia, Autoimmunhemolytic anemia, Autoimmunlymphocytopenia, Chagas' disease, chronic autoimmune thyroiditis, autoimmune hepatitis, Hashimoto's Thyroiditis, atropic thyroiditis, Graves disease, Autoimmune polyglandular syndrome, Autoimmune Addison Syndrome, Pemphigus vulgaris, Idiopathic thrombocytopenic purpura (ITP), Light chain deposition disease, Acute glomerulonephritis, Pemphigus and Pemphigoid disorders, and Epidermolysis bullosa acquisita, Pemphigus foliaceus, Dermatitis herpetiformis, Autoimmune alopecia, Vitiligo, Antiphospholipid syndrome, Myasthenia gravis, Stiff-man syndrome, Goodpasture's syndrome, Sympathetic ophthalmia, Folliculitis, Sharp syndrome and/or Evans syndrome, in particular hay fever, periodontitis, atherosclerosis, rheumatoid arthritis.

Systemic lupus erythematosus (SLE), also known as lupus, is an autoimmune disease in which the body's immune system attacks healthy tissue in various parts of the body. Symptoms vary between people and may be mild to severe. Common symptoms include painful and swollen joints, fever, chest pain, hair loss, mouth ulcers, swollen lymph nodes, feeling tired, and a red rash which is most commonly on the face.

Diseases associated with pathogenic long-lived plasma cells may also comprise B cell non-Hodgkin lymphoma, such as Burkitt lymphoma, chronic lymphocytic leukemia/small lymphocytic lymphoma (CLL/SLL), diffuse large B cell lymphoma, follicular lymphoma, immunoblastic large cell lymphoma, precursor B-lymphoblastic lymphoma, and mantle cell lymphoma.

As used herein, "treatment" of a disease or "treating" a subject afflicted with a disorder shall mean slowing, stopping or reversing the disorder's progression. In the preferred embodiment, treating a subject afflicted with a disorder means reversing the disorder's progression, ideally to the point of eliminating the disorder itself. As used herein, ameliorating a disorder and treating a disorder are equivalent. The treatment of the present invention may also, or alternatively, relate to a prophylactic administration of the active agents described herein. Such a prophylactic administration may relate to the prevention of any given medical disorder, or the prevention of development of said disorder, whereby prevention or prophylaxis is not to be construed narrowly under all conditions as absolute prevention. Prevention or prophylaxis may also relate to a reduction of the risk of a subject developing any given medical condition, preferably in a subject at risk of said condition.

According to a preferred embodiment of the present invention, the treatment comprises the combined administration of said polypeptide with an anti-B cell therapy, an immunosuppressive drug, an anti-tumor therapy or an anti-tumor chemotherapy.

"Combined administration" may relate to concurrent and/or sequential administration of said polypeptide prior to, during and/or subsequent to said anti-B cell therapy, immunosuppressive drug and/or anti-tumor chemotherapy. Combined treatment shall also include a combination treatment regime comprising multiple administrations of either therapeutic component of the treatment. Further embodiments of combined administration are provided herein.

Combined administration encompasses simultaneous treatment, co-treatment or joint treatment, and includes the administration of separate formulations of the polypepdide of the present invention with an anti-B cell therapy, an immunosuppressive drug or an anti-tumor chemotherapy, whereby treatment may occur within minutes of each other, in the same hour, on the same day, in the same week or in the same month or within 3 months as one another. Sequential administration of any given combination of combined agents is also encompassed by the term "combined administration". A combination medicament, comprising one or more of said polypeptide with an anti-B cell therapy, an immunosuppressive drug and/or an anti-tumor chemotherapy, may also be used in order to co-administer the various components in a single administration or dosage.

Anti-tumor therapies (or anti-cancer therapies) of the present invention comprise, without limitation, surgery, chemotherapy, radiotherapy, irradiation therapy, hormonal therapy, targeted therapy, immunotherapy, cell therapy and immune cell therapy.

The term "anti-B cell therapy" refers to therapeutic approaches or compounds that are directed against B cells or pathogenic B cells, for example in the context of B cell mediated disease. B cell specific therapies known to a person skilled in the art and also the novel developments in the field with respect to recent advances are being monitored by the skilled person, so that suitable anti-B cell therapies can be identified. Anti-B cell therapies comprise, without limitation, antibodies and monoclonal antibodies and cell therapeutic agents that are directed against B cell antigens, such as the anti-CD20 monoclonal antibody Rituximab and anti-CD19 CAR T cells or B cell depletion.

In the context of the present invention, chemotherapy refers to a category of cancer treatment that uses one or more anti-cancer drugs (chemotherapeutic agents) as part of a chemotherapy regimen. Chemotherapy may be given with a curative intent (which almost always involves combinations of drugs), or it may aim to prolong life or to reduce symptoms (palliative chemotherapy). Chemotherapy is one of the major categories of medical oncology (the medical discipline specifically devoted to pharmacotherapy for cancer). Chemotherapeutic agents are used to treat cancer and are administered in regimens of one or more cycles, combining two or more agents over a period of days to weeks. Such agents are toxic to cells with high proliferative rates such as cancer or tumor cells.

Chemotherapeutic agents comprise, without limitation, Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine.

Irradiation or radiation therapy or radiotherapy in the context of the present invention relates to a therapeutic approach using ionizing or ultraviolet-visible (UVNis) radiation, generally as part of cancer treatment to control or kill malignant cells such as cancer cells or tumor cells. Radiation therapy may be curative in a number of types of cancer, if they are localized to one area of the body. It may also be used as part of adjuvant therapy, to prevent tumor recurrence after surgery to remove a primary malignant tumor (for example, early stages of breast cancer). Radiation therapy is synergistic with chemotherapy, and can been used before, during, and after chemotherapy in susceptible cancers. Radiation therapy is commonly applied to the cancerous tumor because of its ability to control cell growth. Ionizing radiation works by damaging the DNA of cancerous tissue leading to cellular death. Radiation therapy can be used systemically or locally.

In the context of the present invention, immunosuppressive drugs refer to a class of drugs that suppress, or reduce, the strength of the body's immune system. Some of these drugs are used to make the body less likely to reject a transplanted organ, other immunosuppressant drugs are often used to treat autoimmune disorders. The person skilled in the art is able to identify suitable immunosuppressive drugs. Immunosuppressive drugs comprise, without limitation, corticosteroids, such as prednisone (Deltasone, Orasone), budesonide (Entocort EC), prednisolone (Millipred); Calcineurin inhibitors, such as cyclosporine (Neoral, Sandimmune, SangCya), tacrolimus (Astagraf XL, Envarsus XR, Prograf); mTOR inhibitors such as sirolimus (Rapamune), everolimus (Afinitor, Zortress); IMDH inhibitors, such as azathioprine (Azasan, Imuran), leflunomide (Arava), mycophenolate (CellCept, Myfortic); Biologics such as abatacept (Orencia), adalimumab (Humira), anakinra (Kineret), certolizumab (Cimzia), etanercept (Enbrel), golimumab (Simponi), infliximab (Remicade), ixekizumab (Taltz), natalizumab (Tysabri), rituximab (Rituxan), secukinumab (Cosentyx), tocilizumab (Actemra), ustekinumab (Stelara), vedolizumab (Entyvio); Monoclonal antibodies such as basiliximab (Simulect), daclizumab (Zinbryta), muromonab (Orthoclone OKT3).

The present invention also relates to a mutant nontyphoidal Salmonella (NTS) bacterium for use as a vaccine in the prevention of a NTS infection in a subject, wherein the mutant NTS bacterium does not express a polypeptide comprising or consisting of a polypeptide of the present invention.

In the context of the present invention, a "mutant" bacterium is a bacterium that carries genetic alteration in comparison to the "wild-type", unmodified reference bacterium. Genetic alteration or mutations comprise insertions and deletions genetic material. Mutations may be spontaneous, due to error-prone replication bypass of naturally occurring DNA damage (also called error-prone translesion synthesis), due to errors introduced during DNA repair, or due to induction by mutagens. Also, mutations may be deliberately introduced through genetic manipulation.

A deletion of genetic material is a mutation (a genetic aberration or alteration) in which a part of a chromosome or a sequence of DNA is lost, for example during DNA replication or through genetic engineering. Any number of nucleotides can be deleted, from a single base to several megabases or an entire piece of chromosome. Deletions that do not occur in multiples of three bases can cause a frameshift by changing the 3-nucleotide protein reading frame of the genetic sequence.

In the context of the present invention, a "deletion of the SiiE encoding gene" can refers deletions of the entire genetic material or parts of the genetic material of a NTS bacterium encoding SiiE, wherein the expression of the protein by the NTS bacterium is prevented. Such deletions can also occur as mutations that prevent expression of SiiE, such as small deletions or even insertions of bases that lead to frame shift mutations leading to deletion of SiiE expression.

Salmonella serotypes can be divided into two main groups-typhoidal and nontyphoidal Salmonella.

Nontyphoidal serotypes comprise invasive and non-invasive nontyphoidal Salmonella. Nontyphoidal serotypes are more common, and usually cause self-limiting gastrointestinal disease. They can infect a range of animals, and are zoonotic, meaning they can be transferred between humans and other animals.

Infection with nontyphoidal serotypes (NTS) of Salmonella generally causes food poisoning, wherein infants and young children are much more susceptible to infection. The organisms usually enter through the digestive tract, while inhalation might also lead to infection. Upon entry into the small intestine, the bacteria multiply in tissues and mostly cause gastrointestinal diseases such as enteritis. About 2,000 serotypes of nontyphoidal Salmonella are known to a person skilled in the art.

Invasive strains of nontyphoidal Salmonellae have emerged as a prominent cause of bloodstream infection in African adults and children, with an associated case fatality of 20-25%, and include Salmonella enterica serovar Typhimurium. The clinical presentation of invasive non-typhoidal Salmonella disease in Africa is diverse: fever, hepatosplenomegaly, and respiratory symptoms are common, and features of enterocolitis are often absent. Most cases of invasive nontyphoidal Salmonella infection (iNTS) are caused by S. typhimurium or S. enteritidis. A new form of Salmonella typhimurium (ST313) emerged in the southeast of the African continent 75 years ago. The most important risk factors are HIV infection in adults, and malaria, HIV, and malnutrition in children.

Typhoidal serotypes of Salmonella cause Typhoid fever, are strictly adapted to humans or higher primates and include Salmonella Typhi, Paratyphi A, Paratyphi B and Paratyphi C. In the systemic form of the disease, Salmonellae pass through the lymphatic system of the intestine into the blood of the patients (typhoid form) and are carried to various organs (liver, spleen, kidneys) to form secondary foci (septic form). Endotoxins first act on the vascular and nervous apparatus, resulting in increased permeability and decreased tone of the vessels, upset of thermal regulation, and vomiting and diarrhoea. In severe forms of the disease, enough liquid and electrolytes are lost to upset the water-salt metabolism, decrease the circulating blood volume and arterial pressure, and cause hypovolemic shock. Septic shock may also develop. Shock of mixed character (with signs of both hypovolemic and septic shock) is more common in severe salmonellosis. Oliguria and azotemia may develop in severe cases as a result of renal involvement due to hypoxia and toxemia.

The term "vaccine" in the context of the present invention relates to a biological preparation that provides active acquired immunity to a particular disease, such as cancer, a pathogen or an infectious agent, such as bacteria or viruses. A vaccine can contain an agent or antigen that resembles or is derived from a disease-causing microorganism. Vaccines can be made from weakened, attenuated, mutated or killed forms of the pathogen, its toxins or one of its surface proteins. The agent stimulates the body's immune system to recognize the agent as a threat, destroy it, and recognize and destroy any pathogens or structures comprising the agent or antigen of the vaccine that it later encounters. Vaccines can be prophylactic (example: to prevent or ameliorate the effects of a future infection by a natural or "wild" pathogen), or therapeutic, such as specific cancer vaccines.

In a preferred embodiment of NTS bacterium for use as a vaccine in the present invention, the subject is a human, galliformes, cattle, sheep, swine, horse or rodent. Galliformes is an order of heavy-bodied ground-feeding birds that includes turkey, grouse, chicken, New World quail and Old World quail, ptarmigan, partridge, pheasant, junglefowl and the Cracidae. Cattle, or cows, are raised livestock for meat (beef and veal), as dairy animals for milk and other dairy products. The term "swine" refers to domestic pigs. Rodents are mammals, which are characterized by a single pair of continuously growing incisors in each of the upper and lower jaws. Well-known rodents include mice, rats, squirrels, prairie dogs, porcupines, beavers, guinea pigs, hamsters, gerbils and capybaras.

EXAMPLES

The invention is further described by the following examples. These are not intended to limit the scope of the invention, but represent preferred embodiments of aspects of the invention provided for greater illustration of the invention described herein.

Methods Employed in the Examples

Mice

C57BL/6 mice were purchased from Charles River. CXCL12/GFP knock-in mice (Ara et al., 2003) were kindly provided by Dr. Takashi Nagasawa. Blimpgfp mice (Kallies et al., 2004) were generously supplied by Dr. Stephen L. Nutt. All mice were housed under specific pathogen-free conditions and were used at 6-16 weeks of age. All mouse experiments were performed in accordance with the German law for animal protection and with permission from the local veterinary offices, and in compliance with the guidelines of the Institutional Animal Care and Use Committee.

Bacterial Strains and Growth Condition

All Salmonella strains used in this study were derivatives of Salmonella enterica serovar Typhimurium X3306. Bacteria were grown in LB broth (1% Bacto tryptone (Difco), 0.5% Bacto yeast extract (Difco), 1% sodium chloride, pH7.4) and LB agar. When necessary, the medium was supplemented with chloramphenicol (20 μg/ml), kanamycin (25 μg/ml) and/or nalidixic acid (25 μg/ml). The bacterial strains used in this study are detailed in Table A. The number of viable bacteria in the organs of infected mice was determined by plating serial 10-fold dilutions of the homogenates on LB agar plates. Colonies were routinely counted 18 to 24 h later.

TABLE A

Bacterial strains used in this study

| Strains | Relevant properties[a] | References |
|---|---|---|
| *E. coli* | | |
| BB2395 | Ion146::miniTn10 in MC4100 | Tomoyasu et al., 2001 |
| MC4100 | F⁻ araD139 Δ(argF-lac)U169 rpsL150 relA1 flbB5301 deoC1 ptsF25 rbsR | Our collection |
| *Salmonella enterica* serovar *Typhimurium* | | |
| χ3306 | Virulent strain, gyrA, WT | Gulig and Curtiss III, 1987 |
| CS2022 | ΔIon::Cm in χ3306, ΔLon | Takaya et al., 2002 |
| CS2609 | flhD::Tn10 in χ3306 | Tomoyasu et al., 2003 |
| CS3186 | ΔIon::Cm in CS2609, ΔLonΔFlhD | This study |
| CS10044 | ΔsiiE::Km in χ3306 | This study |
| CS10049 | ΔsiiE::FRT in χ3306, ΔSiiE | This study |
| CS10063 | ΔIon::Cm in CS10049, ΔLonΔSiiE | This study |

[a]Cm, chloramphenicol resistance; Km, kanamycin resistance.

ELISpot Assay and ELISA

To count Ig-secreting cells, MultiScreen filter plates with PVDF membrane (Merck) were activated for 1 min with 35% ethanol followed by washing and were coated with 7.2 μg/ml of goat anti-mouse Ig, F(ab')2 fragment (Jackson ImmunoResearch) overnight at 4° C. After washing and blocking with RPMI1640/10% FCS, diluted fresh cells were added and incubated for 5 h at 37° C. Following incubation, alkaline phosphatase-conjugated anti-IgG, IgG1, IgM or IgA (Southern Biotech) was added for 1 h at 37° C. and spots were visualized with BCIP/NBT Plus substrate (Mabtech) and were counted by ELISpot reader (AID). To measure total and anti-*Salmonella* antibodies, serum samples were incubated in plates coated with sonicated and filtrated *Salmonella* (10 μg/ml) or goat anti-mouse Ig, F(ab')2 fragment. Isotype of antibodies was determined with alkaline phosphatase-conjugated antibodies to mouse IgG and IgM and pNPP substrate (Sigma) and was measured by SpectraMax i3x (Molecular Devices).

Flow Cytometry

Single-cell suspensions were prepared from the spleen, femur, small intestine and blood of individual mice. The viability of cells was assessed by Trypan blue exclusion. Blood cells were counted by Türk's solution (Merck). The absolute number of leukocytes in blood was enumerated based on the assumption that the total blood volume is 7.5% of the body weight. The total number of BM cells was calculated assuming that the cell number yielded from one femur corresponds to 6.3% of the entire BM population. For cell staining, cells were stained for 20 min at 4° C. with antibodies against B220 (RA3-6B2), IgD (11.26c), CD138 (REA104), CD44 (IM7), integrin α1 (REA493), α6 (GoH3), α7 (3C12), (Miltenyi Biotec), IgM (AF6-78), integrin α2 (HMa2), αV (RMV-7) (BioLegend), a3 (goat polyclonal), BCMA (161616) (R&D systems), integrin α4 (PS2, Abcam), CXCR4 (2B11, eBioscience), IgA (goat polyclonal anti-IgA; IgM- and IgG-absorbed, Southern Biotech) and 67-LR/RPSA (MLuC5, Santa Cruz Biotechnology). To exclude dead cells, we stained cells with 1 μg/ml propidium iodide (Sigma). For intracellular staining, cells were fixed with 2% formaldehyde (Sigma) for 15 min after cell surface staining and were stained with goat polyclonal anti-IgG Fc fragment (F(ab')2 fragment, Jackson ImmunoResearch) in the presence of 0.5% saponin (Sigma). To test the binding of SiiE fragment to IgG-secreting plasma cells, BM or splenic cells were incubated with GST-SiiE 97-170 or GST protein in Iscove's Modified Dulbecco's Medium (IMDM) with 10% FCS and 1 mM MnCl2 on ice for 30 min, stained with antibodies against GST (B-14, Santa Cruz Biotechnology), CD138, IgM, IgA and B220 on ice for 20 min and analyzed by flow cytometry. IgM- and IgA-secreting plasma cells express surface Ig (Kamata et al., 2000; Reynolds et al., 2015). More than 95% of sorted IgM-IgA-CD138+B220- plasma cells were IgG-secreting cells when measured by ELISpot assay (data not shown). Stained samples were measured by BD FACS Cantoll or LSRII flow cytometer (BD Biosciences) and were analyzed by FlowJo software (Flowjo, LLC).

Immunofluorescent Staining and Confocal Microscopy

For immunofluorescence staining, as described previously (Tokoyoda et al., 2009), samples were fixed in 4% paraformaldehyde and equilibrated in 30% sucrose (Sigma). Cryosections of adult femurs were produced by Kawamoto's film method (Kawamoto and Kawamoto, 2014), blocked with 5% FCS in PBS for 30 min, stained with antibodies against laminin β1 (LT3, 1:100, Dianova), VCAM-1 (429, 1:10, Miltenyi Biotec), fibronectin (rabbit polyclonal, 1:700, Sigma), IgG Fc fragment (F(ab')2 fragment, 1:400, Jackson ImmunoResearch) and IgM (11/41, 1:100, eBioscience) for over 2 h and mounted with fluorescent mounting medium (DakoCytomation). Affinity-purified rabbit polyclonal anti-SiiE antibodies were generated by GenScript. As secondary antibodies, Cy3-labelled anti-rat IgG (1:600, Jackson ImmunoResearch), AlexaFluor 546-labeled streptavidin or anti-rabbit IgG (1:2000 or 1:600, Life Technologies) were used. All histological analyses were carried out with a confocal laser microscope (LSM710, Carl Zeiss).

RNA Preparation and Quantitative RT-PCR Analysis

Total RNA was isolated using the Trizol reagent (Life Technologies). The complementary DNA was synthesized using oligo (dT) primers and High Capacity RNA-to-cDNA Kit (AppliedBiosystems). For quantitative RT-PCR analyses, the following primers were used: cxcll2 fwd AAACCAGTCAGCCTGAGCTACC (SEQ ID NO 14), rev GGCTCTGGCGATGTGGC (SEQ ID NO 15); april fwd CTGGAGGCCCAGGGAGACAT (SEQ ID NO 16), rev GCACGGTCAGGATCAGAAGG (SEQ ID NO 17); Igals1 fwd ATCCTCGCTTCAATGCCCATGG (SEQ ID NO 18), rev GGTGATGCACACCTCTGTGATG (SEQ ID NO 19); hprt fwd TCCTCCTCAGACCGCTTTT (SEQ ID NO 20), rev CATAACCTGGTTCATCATCGC (SEQ ID NO 21).

Construction of *Salmonella* Mutant Strains

The strain CS10044 (ΔsiiE::Km) was constructed as followed by λRed and flippase (FLP)-mediated recombination essentially as described by Datsenko and Wanner (Datsenko and Wanner, 2000). PCR products used to construct gene replacements were generated with template plasmid pKD4 and the primer set of siiE-P1-F (TTACCACGCCGC-GTGGTTCAGTGATCATTGTCAATGGCGCTCGTGT-AGGCTGGAGCTGCTT C) (SEQ ID NO 22) and siiE-P2-R (GTGCTGTCCAGCACGATAGTCGGTTCT-GACAGTAGGGTATCGCATATGAATATCCTCCTTA G) (SEQ ID NO 23). 1.4-kbp fragment generated was purified and then introduced into strain χ3306 carrying pKD46 encoding the λRed recombinase, by transformation. The insertion of Km-resistant gene in siiE locus was verified by PCR amplification of the chromosomal DNA with the primer set of siiE-check-F (TAATGC-CAAAGGCGCAAAAG) (SEQ ID NO 24) and siiE-check-R (TACGTTGGTCAGGTGATCGC) (SEQ ID NO 25) and by DNA sequencing. To construct CS10049 (ΔsiiE:: FRT), pCP20 encoding FLP recombinase was introduced into CS10044 by transformation. The FRT insertion in siiE was checked by PCR.

To construct CS3186 (ΔLonΔF1hD) and CS10063 (ΔLonΔSHE), bacteriophage P22 was propagated on CS2022, and the resultant lysates were used for infection of CS2609 and CS10049, respectively. The transductants were selected for chloramphenicol resistance.

Purification of GST-Tapped Fusion SiiE 97-170 Protein

A plasmid, pTKY1271, for purification of SiiE 97-170 protein fused to the C-terminus of the Glutathione S-transferase (GST) was amplified from the chromosome of X3306 by colony direct PCR, using GST-SiiE97-BamHI-F (5'-CTGGGATCCTCTGCTCAGGTAGAAAAGAAAGG-3') (SEQ ID NO 26) and GST-SHE170-Sall-R (5'-CTCGAGTCGACTTACAAAAAGTTCTGCAGCATTTC-3') (SEQ ID NO 27) primers. The fragment generated was cleaved with BamHI at the 5' end and Sall at the 3' end, and cloned into vector pGEX-6P-1.

*E. coli* DH5αZ1 was transformed with the plasmid pTKY1271, and the transformants were grown at 37° C. to an OD600 of 0.5 in 3l of L broth containing 0.5% glucose and 50 μg/ml ampicillin before adding IPTG to 1 mM induced GST-tagged fusion SiiE 97-170 expression. After 3 h incubation at 37° C., cells were pelleted and resuspended in B-PERTM (PBS) Bacterial Protein Extraction Reagent (ThermoFisher) containing 50 μg/ml DNaseI (Sigma-Aldrich). Cells were lysed for 30 min on ice and centrifuged at 8,000 ×g for 30 min at 4° C. The supernatant was added to a MagneGST Glutathione Particles (Promega) equilibrated with PBS and incubated with gentle mixing for 2 h at 4° C. After washing with PBS, the fusion protein was eluted with Elution buffer (50 mM Tris-HCl pH 8.1, 50 mM gultathione). To purified the GST-tagged fusion SiiE 97-170 protein, this fraction was run on gel chromatography (Superose6 10/300; GE Healthcare) with PBS. The peak fraction was concentrated with Centriprep YM-10 (Millipore) and then used as the purified GST-tagged fusion SiiE 97-170 protein.

Characterization of Protein in Culture Supernatant

CS3186 cells were grown in 6 liters of LB broth at 37° C. to an OD600 of 1.0 and removed by centrifugation at 6,000 ×g for 10 min at 4° C. The supernatant was filtered using an Express PLUS filter system (Millipore) and then proteins were precipitated by adding ammonium sulfate to a final concentration of 80%. The precipitated proteins were collected by centrifugation at 6,000 ×g for 10 min at 4° C. and dissolved with 10 ml of 50 mM Tris-HCl pH8.0. After desalting by PD-10 column (GE Healthcare), proteins were loaded onto RESOURSE Q column (1 ml, GE Healthcare), equilibrated in buffer A (20 mM Tris-HCl pH8.0, 10% glycerol) and eluted with buffer A containing a 0-1 M NaCl linear gradient. After dialysis with PBS, the ability to numerically diminish the plasma cells was assessed by inoculation of 200 μl of each fraction into C57BL/6 mice. Proteins in the fractions with this activity were recovered by TCA precipitation and were separated with 7.5% SDS-PAGE. The proteins visualized by Coomassie brilliant blue staining were analyzed by nano LC-MS/MS (Japan Bio Services Co.).

In Vitro Cell Adhesion Assay

As described previously (Hanazawa et al., 2013), 96-well plates (Greiner Bio-One) were immobilized with 30 μg/ml of murine laminin (Sigma) overnight at 4° C., dried, washed with PBS and blocked with 2% fatty acid-free bovine serum albumin for 2 h at 37° C. Ten thousand sorted CD138+ B220-IgM-IgA-cells from BM of C57BL/6 mice were incubated with GST-SiiE 97-170 or GST protein in IMDM with 10% FCS and 1 mM MnCl2 on ice for 30 min and then incubated additionally with 1 ng/ml of phorbol 12-myristate 13-acetate for 1 h at 37° C. Following washing three times with pre-warm PBS including 1 mM CaCl2 and 0.5 mM MgCl2 with automatic microplate washer (Dispense speed 4, Aspirate speed 4, Bio-Tek), adherent cells were measured as viable cells using the Cell-titer Glo reagent (Promega) and a luminometer (SpectraMax, Molecular Devices).

Statistical Analyses

All statistical analyses were performed using two-tailed Student's t-tests.

Growth Curve of Salmonella enterica serovar Typhimurium

Bacterial cells of strains CS2022 (ΔLon, circle) and CS10063 (ΔLonΔSHE, square) were grown overnight at 37° C. and diluted 1:100 into fresh medium. At indicated time points, an aliquot of the culture was diluted with PBS and plated out on LB agar to determine the number of bacteria.

TCA Precipitation of Secreted Proteins

Bacterial cells were grown in 10 ml of LB broth at 37° C. to an OD600 of 1.0 and removed by centrifugation at 6,000×g for 10 min at 4° C. The supernatant was filtrated using a Minisart High Flow syringe filter (Sartrius), then mixed with pre-chilled trichloroacetic acid (TCA; final concentration 10%), chilled on ice for 20 min, and centrifuged at 6,000 ×g for 10 min at 4° C. The pellets were washed once with acetone and suspended in 100 µl of Laemmli's SDS-sample buffer. Proteins were detected by SDS-12.5% PAGE, followed by staining with Coomassie brilliant blue.

Results of the Examples

Summary of the Results

Serum IgG, which is mainly generated from IgG-secreting plasma cells in the bone marrow (BM), protects our body against various pathogens. Here we show that Salmonella specifically reduces numbers of IgG-secreting plasma cells but not IgM-secreting cells in the BM and consequently reduces IgG titers in serum, whilst Salmonella is undetectable in the BM. Using chromatography and mass spectrometry, we identified SiiE protein which is secreted from Salmonella and specifically reduces numbers of IgG-secreting plasma cells in the BM. The reduction was caused by a Salmonella protein SiiE but not by lipopolysaccharide (LPS), flagellin or reduced CXCL12. SiiE-deficient Salmonella failed to reduce numbers of BM IgG-secreting plasma cells and strongly induced production of Salmonella-specific IgG in the infected mice. A forty amino acid-long peptide from the N-terminal domain of SiiE protein with homology to murine laminin β1 also reduced numbers of IgG-secreting plasma cells in the BM, suggesting that SiiE inhibits the interaction between the plasma cells and laminin β1. Histological analysis revealed that laminin β1 specifically binds to IgG- but not IgM-secreting plasma cells. Our study demonstrates that laminin β1 is a component of distinct survival niches for IgG-secreting plasma cells in the BM. We suggest that Salmonella secretes SiiE and inhibits the retention of IgG-secreting plasma cells in the BM as a strategy to escape from humoral immunity. In applied terms, SiiE-deficient Salmonella is promising vaccine candidates and SiiE-derived components would be harnessed for the treatment of autoimmune diseases and multiple myeloma by depleting pathogenic memory plasma cells in the BM.

Example 1

Salmonella Specifically Reduces Numbers of IaG-Secreting Plasma Cells in the BM

Figure 3:
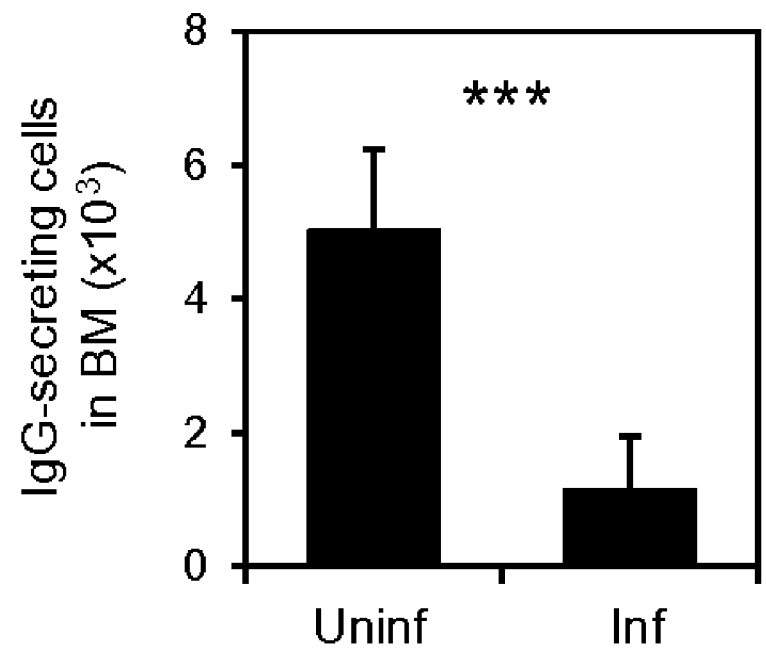
FIG. 3. Wild-type *Salmonella* reduces BM IgG-secreting plasma cells. Mice were infected with *Salmonella* wild-type strain and on day 5 were analyzed for IgG-secreting plasma cells by ELISpot assay. n=6-7. The data are representative of two independent experiments. ***$p<0.001$.
Figure 2:
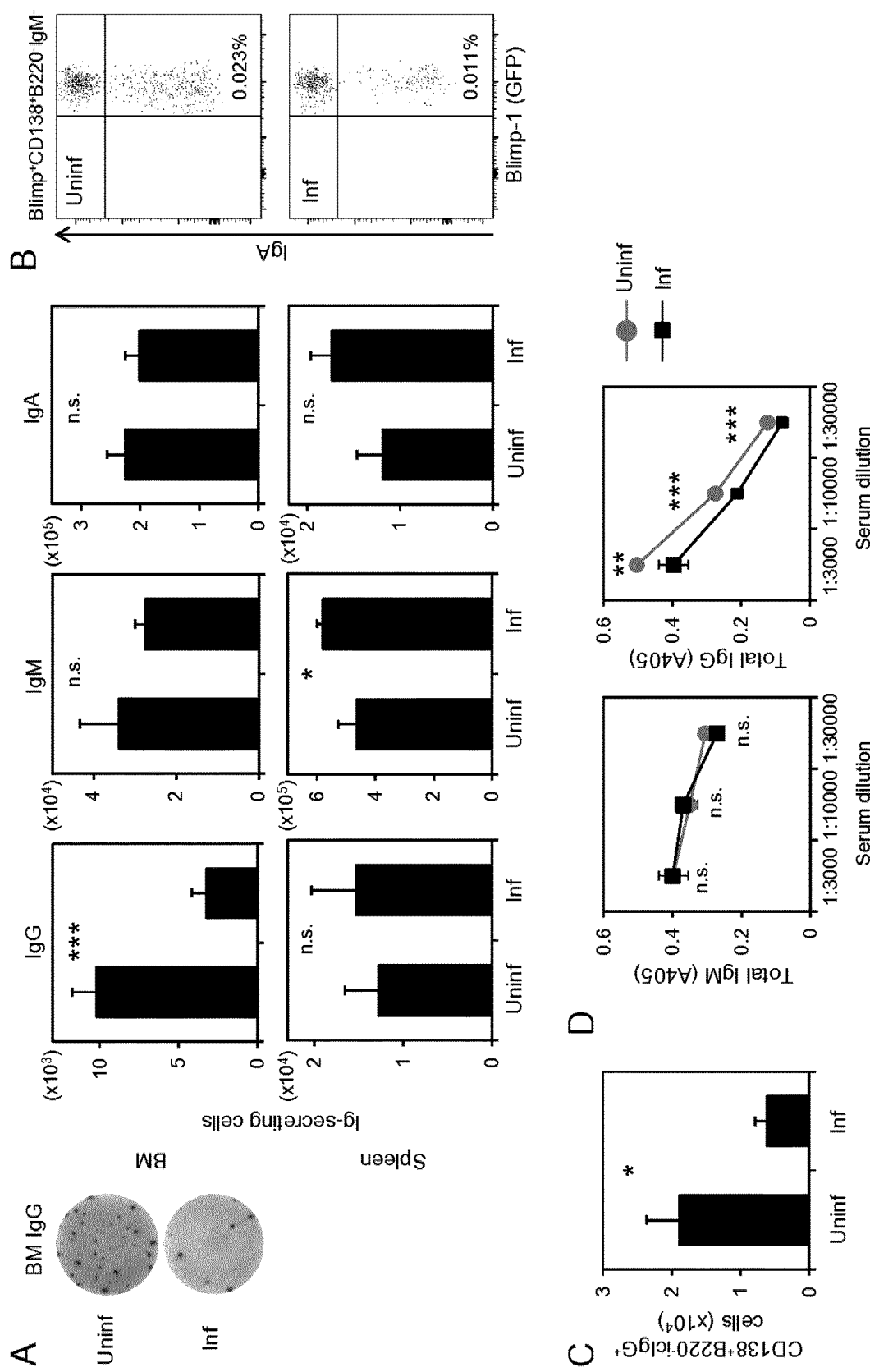
FIG. 2. Numerical reduction of BM IgG-secreting plasma cells by intraperitoneal infection with *Salmonella*. (A) *Salmonella* reduces numbers of IgG-secreting cells in the BM. C57BL/6 mice were infected intraperitoneally (i.p.) with $10^4$ CFU of attenuated *Salmonella* and were sacrificed on day 4 after infection. Cells in the spleen and femurs of *Salmonella*-infected (Inf) or uninfected (Uninf) mice were analyzed for IgM- or IgG-secreting cells by ELISpot assay. Photos show ELISpot data from IgG-secreting cells in the BM of infected or uninfected mice. n=10. (B) *Salmonella* reduces numbers of Blimp-1+IgM-cells in the BM. Blimpgfp mice were infected i.p. with $10^4$ CFU of attenuated *Salmonella* and were sacrificed on day 4 after infection. BM cells were analyzed by flow cytometry for the expression of IgA and Blimp-1 in Blimp-1+CD138+B220-IgM-IgA-cells. Percentages show the frequencies of Blimp-1+CD138+B220-IgM-cells in total live cells. n=4. (C) *Salmonella* numerically reduces intracellular (ic) IgG+ plasma cells in the BM. C57BL/6 mice were infected i.p. with $10^4$ CFU of attenuated *Salmonella* and were sacrificed on day 4 after infection. BM cells were analyzed by flow cytometry for the expression of intracellular IgG in B220-CD138+cells. n=6. (D) *Salmonella* reduces IgG titers in serum. Sera of *Salmonella*-infected and uninfected mice on day 7 post infection were analyzed for titers of total IgM and IgG by ELISA. n=4. The data are representative of at least two independent experiments. *$p<0.05$, $p<0.01$, *$p<0.001$, n.s. not significant.
Figure 4:
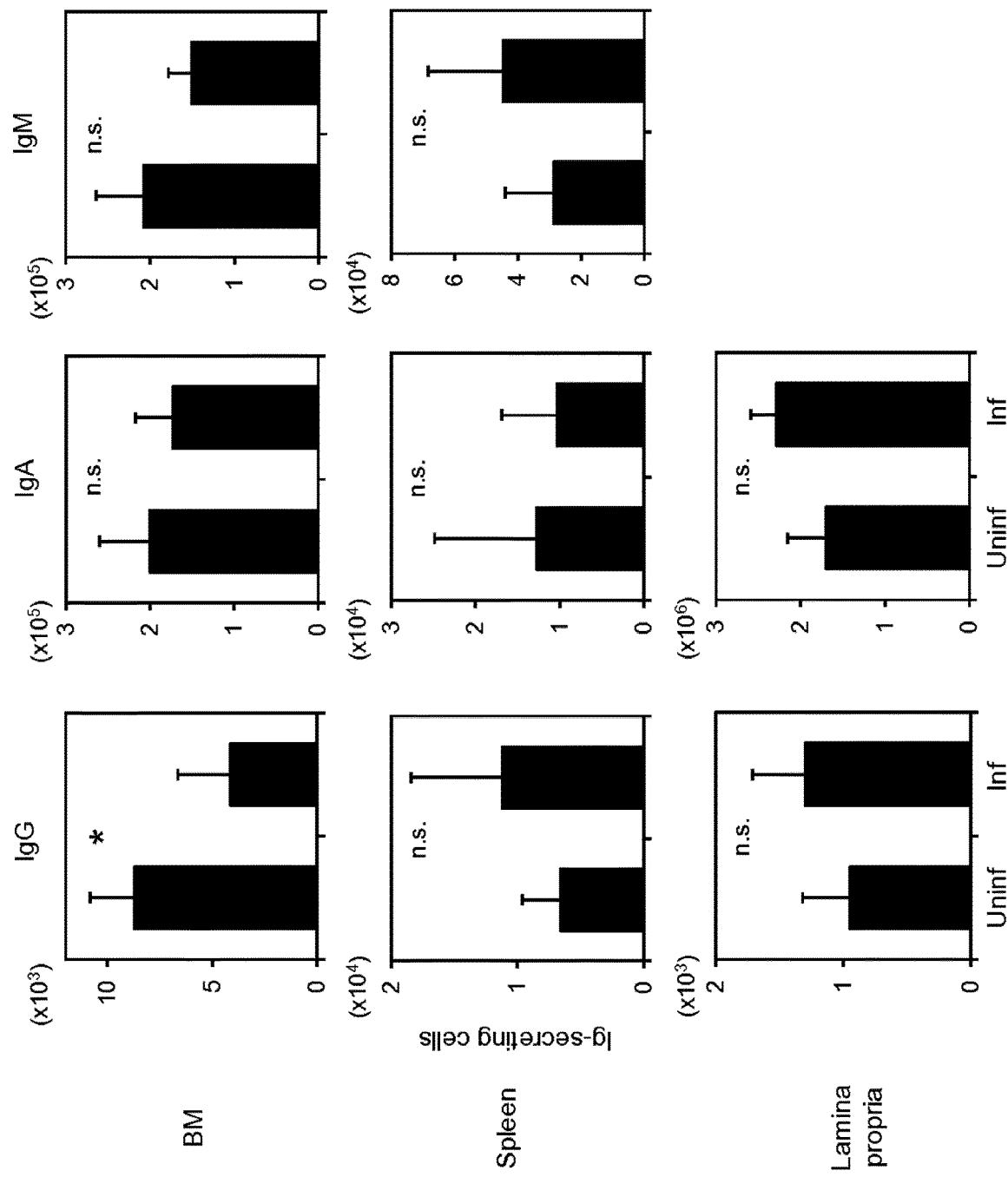
FIG. 4. Numerical reduction of BM IgG-secreting plasma cells by oral infection with *Salmonella*. C57BL/6 mice were infected orally with $10^7$ CFU of attenuated *Salmonella* and were analyzed on day 7. Cells from the spleen, femurs and lamina propia from infected or uninfected mice were analyzed for IgM- or IgG- and IgA-secreting cells by ELISpot assay. n=7. The data are representative of two independent experiments. *$p<0.05$.

Salmonella escapes from humoral immunity and can survive in the body for long time periods, resulting in chronic infectious disease. Long-lasting persistence requires that Salmonella continues to relocate between short-lived macrophages via body fluids containing antibodies. We first examined the influence of Salmonella on the production of antibodies, using a chronic infection model, mimicked by intraperitoneal infection of attenuated Salmonella (Londepletion) (Takaya at el., 2002; Kodama et al., 2005). C57BL/6 mice received 104 colony-forming units (CFU) of the attenuated Salmonella intraperitoneally. Infected Salmonella expanded on days 4-7 in the spleen and liver and stayed there as a small population until day 20, the end of the observation period (FIG. 1). On day 4, at the peak of Salmonella expansion, polyclonal antibody-secreting cells in the spleen and BM were enumerated by ELISpot assay. Surprisingly, numbers of IgG-secreting plasma cells in the BM were reduced, but numbers of BM IgM- and splenic IgG-secreting cells were not affected (FIG. 2A). Numbers of splenic IgM-secreting plasma cells were slightly increased, probably due to a generic bacterial stimulant, e.g. LPS. Moreover, numbers of Blimp-1+CD138+IgM-IgA-B220- cells, mostly including IgG+ plasma cells, and of intracellular IgG+CD138+B220-cells in the BM were also significantly reduced (FIGS. 2B and 2C). The reduction of numbers of BM IgG-secreting cells was also observed after infection with wild-type Salmonella (FIG. 3). The numerical reduction of BM IgG-secreting plasma cells which are the main source of serum IgG, may affect the titers of IgG in serum. On day 7 after infection, polyclonal IgG but not IgM titers in serum were significantly impaired (FIG. 2D). The specific numerical reduction of BM IgG-secreting plasma cells was also shown in case of natural infection with Salmonella. Oral infection with 107 CFU of attenuated Salmonella reduced numbers of BM IgG-secreting plasma cells, but did not affect plasma cell numbers in the spleen and lamina propria (FIG. 4).

Example 2

Salmonella Protein SiiE Reduces BM IaG-Secreting Plasma Cells

Figure 5:
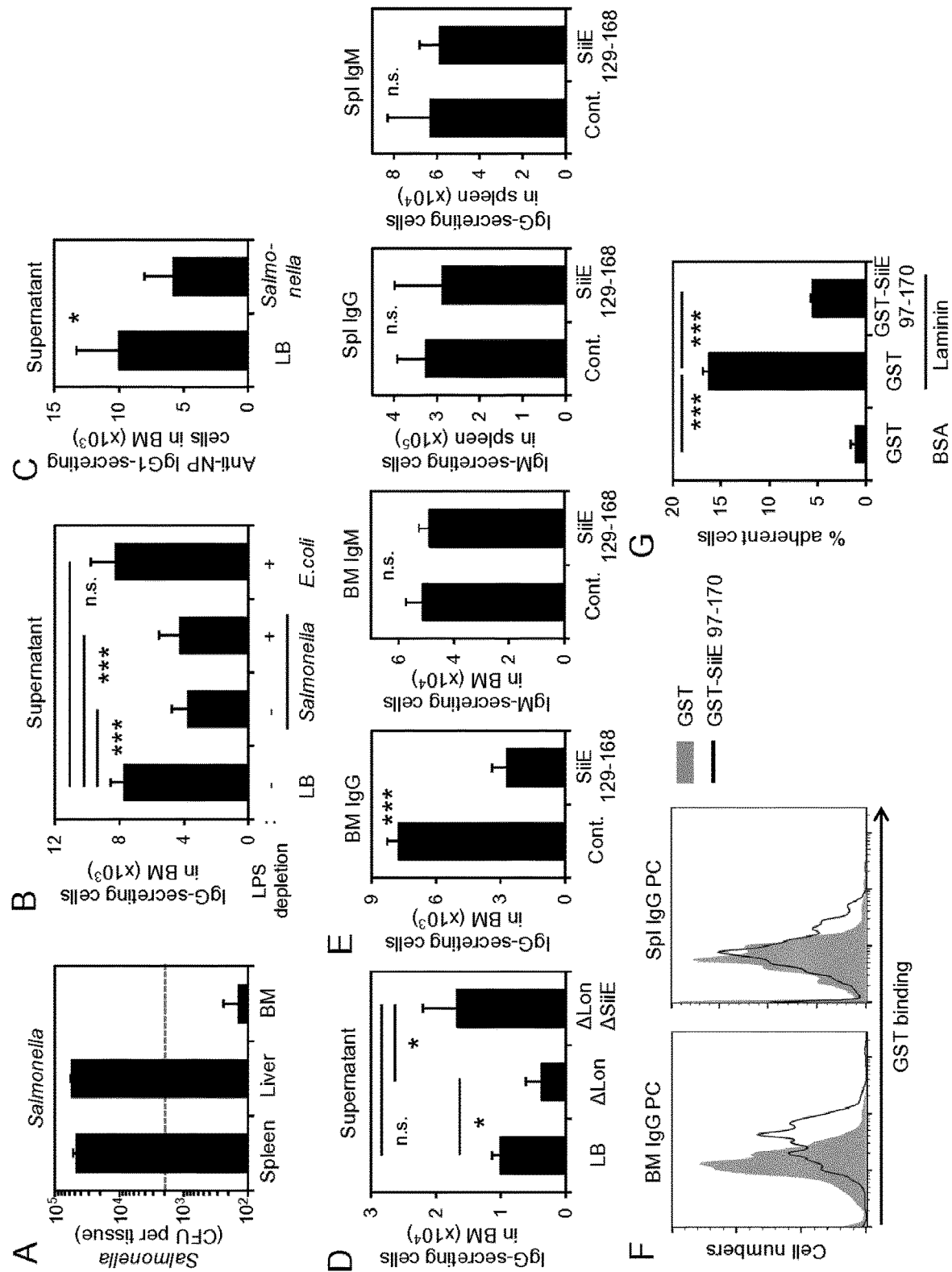
FIG. 5. Identification of the microbial component reducing numbers of BM IgG-secreting plasma cells. (A) *Salmonella* colonizes in the spleen and liver but not in the BM. The CFU of *Salmonella* in the spleen, liver and BM of *Salmonella*-infected mice on day 4 after infection was counted. The dotted line represents the limit of detection. n=3-6. (B) *Salmonella*-specific microbial component reduces numbers of BM IgG-secreting plasma cells. C57BL/6 mice received 200 µl of LB medium, untreated or LPS-depleted culture supernatants from flagellin-deficient attenuated *Salmonella* or *Escherichia coli* (ΔLonΔFlhD) and on the next day (24 h later) were analyzed for IgG-secreting cells by ELISpot assay. n=8. (C) Supernatant from attenuated *Salmonella* reduces numbers of antigen-specific IgG-secreting plasma cells in the BM. C57BL/6 mice were primed i.p. with 100 µg of NP-CGG/IFA (day 0) and were boosted with 50 µg of NP-CGG 4 weeks after priming (day 28). Mice were infected i.p. with 200 µl of LB and LPS-depleted supernatant from flagellin-deficient attenuated *Salmonella* on day 41 and analyzed for IgG-secreting cells on the next day. n=6. (D) Supernatant from SiiE-deficient attenuated *Salmonella* fails to reduce BM IgG-secreting plasma cell numbers. C57BL/6 mice received i.p. 200 µl of LB medium and LPS-depleted supernatants from attenuated *Salmonella* ΔLon or ΔLonΔSiiE and on the next day were analyzed for IgG-secreting cells by ELISpot assay. n=5. (E) Forty amino acid-peptide from the N terminus of SiiE protein reduces numbers of BM IgG-secreting plasma cells. C57BL/6 mice received i.p. 100 µg peptide coding SiiE amino acid 129-168 and on the next day were analyzed for IgG- and IgM-secreting cells in the BM and spleen. n=5. (F) SiiE fragment binds to IgG-secreting plasma cells in the BM but not spleen. BM or splenic cells from C57BL/6 mice were incubated with 30 µg/ml of GST-SiiE 97-170 or GST protein, stained with anti-GST antibodies, and analyzed by flow cytometry. n=3. (G) SiiE fragment inhibits the adhesion of BM IgG-secreting plasma cells to laminin in vitro. Sorted CD138+B220-IgM-IgA-cells from the BM of C57BL/6 mice were treated with GST-SiiE 97-170 or GST protein and incubated with laminin-coated plates. Adherent cells were counted after washing. The data are representative of at least two independent experiments. *$p<0.05$, ***$p<0.001$.

On day 4 after infection, most Salmonella could be detected in the spleen and liver but not in the BM (FIG. 5A), suggesting that Salmonella in the spleen and liver impacts on IgG-secreting plasma cells in the BM from a distance, likely by secreted proteins. The culture supernatant of Salmonella includes several inducers of innate immune activation, like LPS and flagellin. We removed LPS from supernatant of flagellin-deficient attenuated Salmonella and injected the supernatant into C57BL/6 mice. Untreated and LPS-free supernatant from flagellin-deficient Salmonella reduced numbers of BM IgG-secreting plasma cells alike (FIG. 5B). To determine whether the reduction is specific to Salmonella, supernatant from flagellin- and Lon-deficient Escherichia coli was injected. Escherichia coli unaffected numbers of BM IgG-secreting plasma cells (FIG. 5B). The LPS/flagellin-free supernatant also reduced numbers of antigen-specific IgG-secreting plasma cells in the BM, which had been generated by immunization with (4-hydroxy-3-nitrophenyl)acetyl chicken gamma globulin (NP-CGG), as well as polyclonal IgG-secreting plasma cells (FIG. 5C). These data suggest that *Salmonella* supernatant devoid of LPS and flagellin contains a component which impacts on BM IgG-secreting plasma cells.

Figure 6:
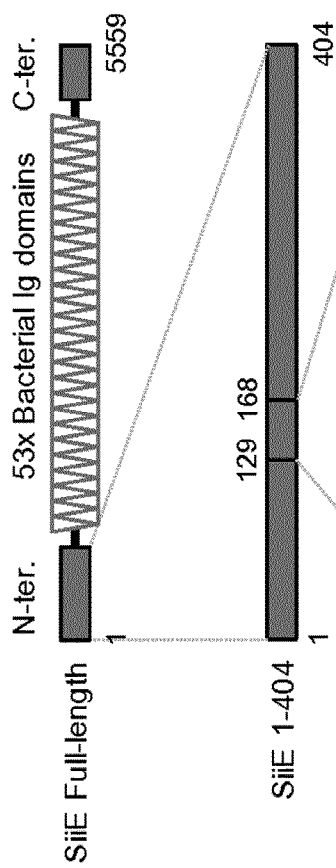
FIG. 6. SiiE has a high homology with conserved sequence of laminin β1.
Figure 7:
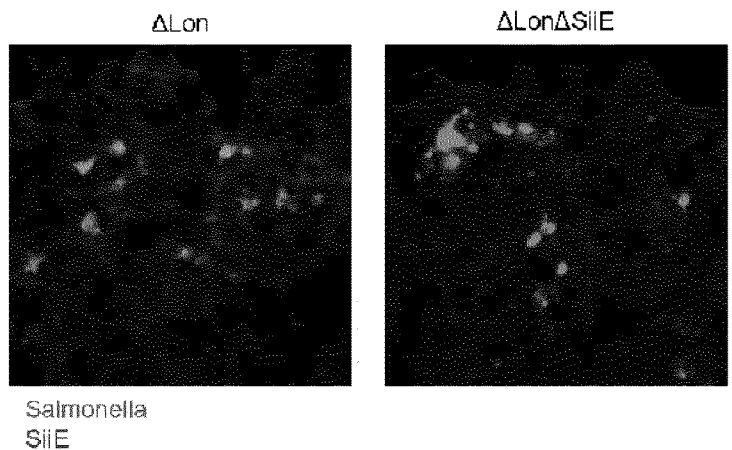
FIG. 7. Distribution of *Salmonella* and SiiE in the spleen of *Salmonella*-infected mice. Splenic frozen sections from C57BL/6 mice infected with *Salmonella* ΔLon or ΔLonΔSHE were stained for *Salmonella* and SiiE protein. The data are representative of two independent experiments.

We fractionated proteins in the supernatant by ion-exchange chromatography and screened each fraction for its impact on BM IgG-secreting plasma cells in vivo. By sodium dodecyl sulfate-polyacrylamide gel electrophoresis (SDS-PAGE) and mass spectrometry, we then identified a protein, SiiE, as most likely active component. Supernatant from SiiE-deficient, attenuated *Salmonella* failed to reduce numbers of IgG-secreting plasma cells in the BM (FIG. 5D). SiiE is a large protein of 5,559 amino acids, with 2 distinct regions in the N- and C-terminus and 53 repeated bacterial Ig domains in between (FIG. 6; Barlag and Hensel, 2015). SiiE is secreted and is involved in the adhesion to gut intestinal epithelial cells (Gerlach et al., 2007). We detected SiiE protein which is secreted by *Salmonella* and which is located on *Salmonella* in the spleen (FIG. 7). From a search with the Basic Local Alignment Search Tool (BLAST, the National Library of Medicine), two sequences of the N-terminal region had high homologies (score <0.01) to murine laminin β1 and myosin 7A, respectively. Since myosin is an intracellular protein, we focused on laminin β1, hypothezising that SiiE competes with laminin β1 for interaction with IgG-secreting plasma cells. SiiE 129-168, a synthetic 40-amino acid peptide with high homology to a conserved sequence of laminin β1 in many species (FIG. 6), also markedly reduced numbers of BM IgG-secreting plasma cells (FIG. 5E). Furthermore, SiiE 97-170 fragment could bind IgG-secreting plasma cells in the BM but not in the spleen (FIG. 5F) and could inhibit the adhesion of BM IgG-secreting plasma cells to laminin in vitro (FIG. 5G). These results suggest that SiiE, a microbial component from *Salmonella*, modulates BM IgG-secreting plasma cells by competing with laminin β1.

Example 3

Figure 8:
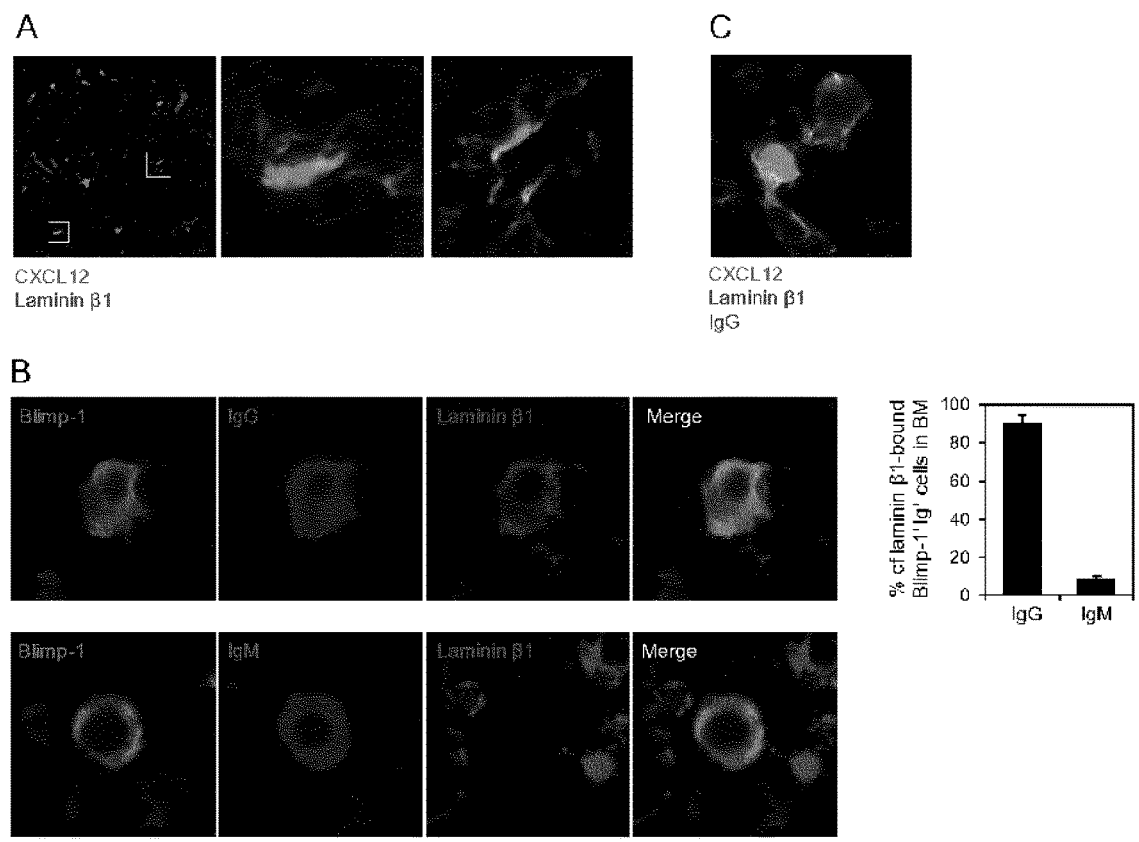
FIG. 8. BM IgG-secreting plasma cells persist in laminin β1+CXCL12-expressing stromal cells. (A) The distribution of laminin β1 on CXCL12+ stromal cells in the BM. BM frozen sections from CXCL12/GFP knock-in mice were stained for laminin β1. (B) IgG- but not IgM-secreting plasma cells contact laminin β1. BM frozen sections from Blimpgfp mice were stained for laminin β1 and IgG or IgM. Bar graph shows the percentages of laminin β1-bound Ig+ plasma cells in total Ig+plasma cells. n=80-100 (3 mice). (C) IgG+cells contact laminin β1+CXCL12+ stromal cells in the BM. BM frozen sections from CXCL12/GFP knock-in mice were stained for laminin β1 and IgG. The data are representative of two independent experiments.
Figure 9:
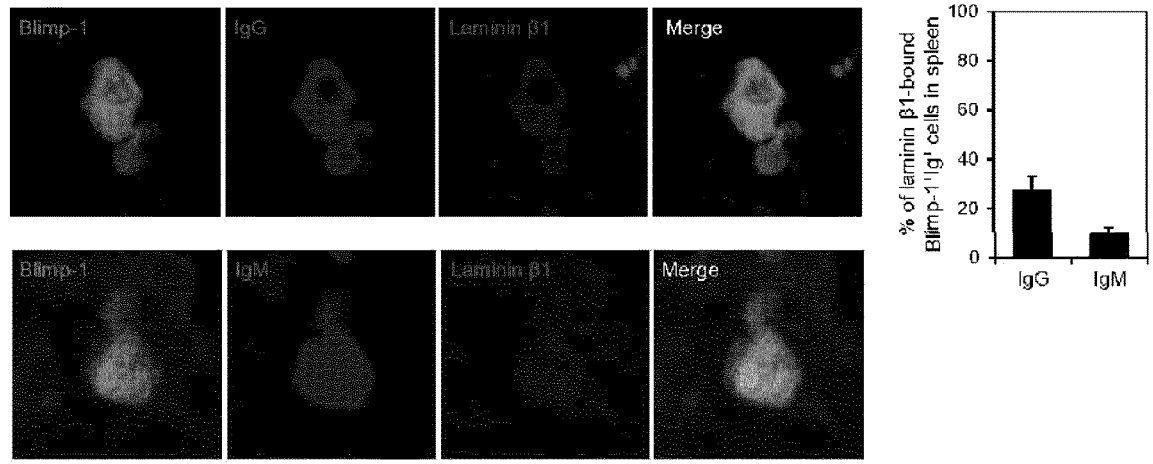
FIG. 9. Splenic plasma cells do not contact laminin β1. Splenic frozen sections from Blimpgfp mice were stained for laminin β1 and IgG or IgM. Bar graph shows the percentages of laminin β1-bound Ig+ plasma cells in total Ig+ plasma cells. n=50. The data are representative of two independent experiments.
Figure 10:
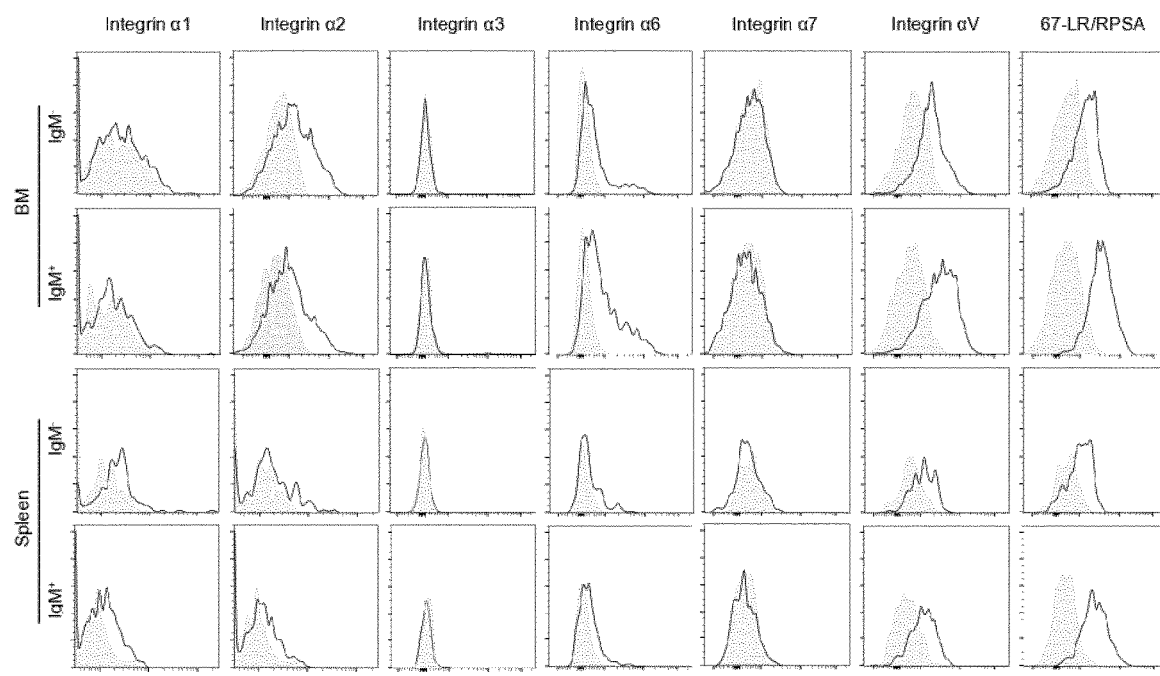
FIG. 10. Potential receptors of laminin on plasma cells. BM and splenic cells from Blimpgfp mice were analyzed for the expression of each laminin receptors on Blimp-1+CD138+B220-IgM-or IgM+ plasma cells. Staining with isotype control is shown in grey. n=3. The data are representative of two independent experiments.

Lamininβ1+CXCL12+Stromal Cells Organize Survival Niches for BM IgG-Secreting Plasma Cells Does laminin β1 bind to BM IgG-secreting plasma cells? Histological analysis showed that laminin β1 is ubiquitously distributed in the marrow (FIG. 8A, left). About 30% of CXCL12+ stromal cells were costained for laminin β1. Laminin β1 is distributed on the cell surface and cellular processes of CXCL12+ stromal cells (FIG. 8A, right). To determine whether laminin β1 interacts with IgG+ or IgM+ Blimp-1+ plasma cells in the BM and spleen, we stained frozen sections of Blimpgfp mice for laminin β1 and IgG or IgM. About 90% of BM IgG+Blimp-1+ plasma cells bound to laminin β1, while fewer IgM+Blimp-1+ and splenic IgG+Blimp-1+ plasma cells attached to laminin β1 (FIGS. 8B and 9). We had already shown earlier that about 90% of the IgG+ plasma cells are in contact with CXCL12-expressing cells (Tokoyoda et al., 2004; Zehentmeier et al., 2014). In fact, most IgG+cells contacted laminin β1-coated CXCL12+cells (FIG. 8C). These histological data suggest that BM IgG-secreting plasma cells preferentially reside in laminin β1+CXCL12+ stromal niches. How do IgG-secreting plasma cells bind to laminin β1? The potential receptors for laminin are integrin α1, α2, α3, α6, α7 and αV and 67 kD laminin receptor (RPSA) (Gu et al., 1999; Belkin and Stepp, 2000). We compared the expression of these receptors on IgM− and IgM+ Blimp-1+ plasma cells in the BM and spleen (FIG. 10). Most receptors were expressed or not on both IgM− and IgM+ plasma cells, although more BM IgM-Blimp-1+ plasma cells expressed integrin α2 than other plasma cells.

Example 4

Loss of SiiE Enhances the Production of Anti-*Salmonella* IaG

Figure 11:
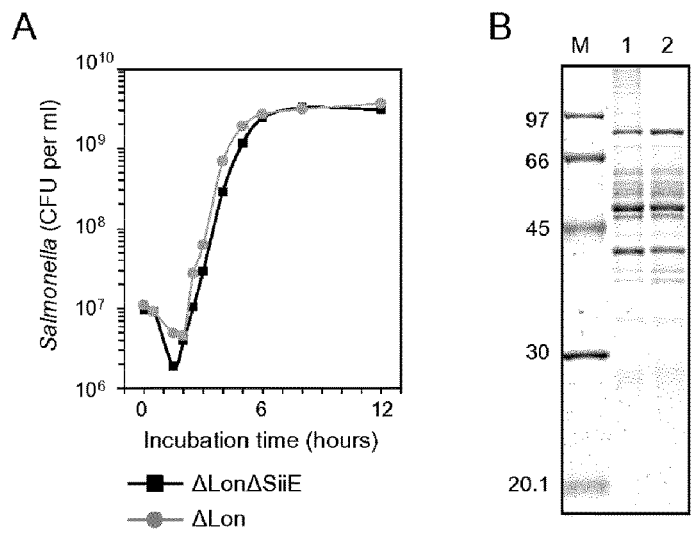
FIG. 11. Microbiological feature of *Salmonella enterica* serovar Typhimurium strains, ΔLon and ΔLonΔSHE. (A) Growth curve of strains ΔLon (circle) and ΔLonΔSHE (square). (B) SDS-12.5% PAGE pattern of secreted proteins in the culture supernatants prepared from strains ΔLon (lane 1) and ΔLonΔSHE (lane 2). Lane M contains low molecular mass standards. The data are representative of two independent experiments.
Figure 12:
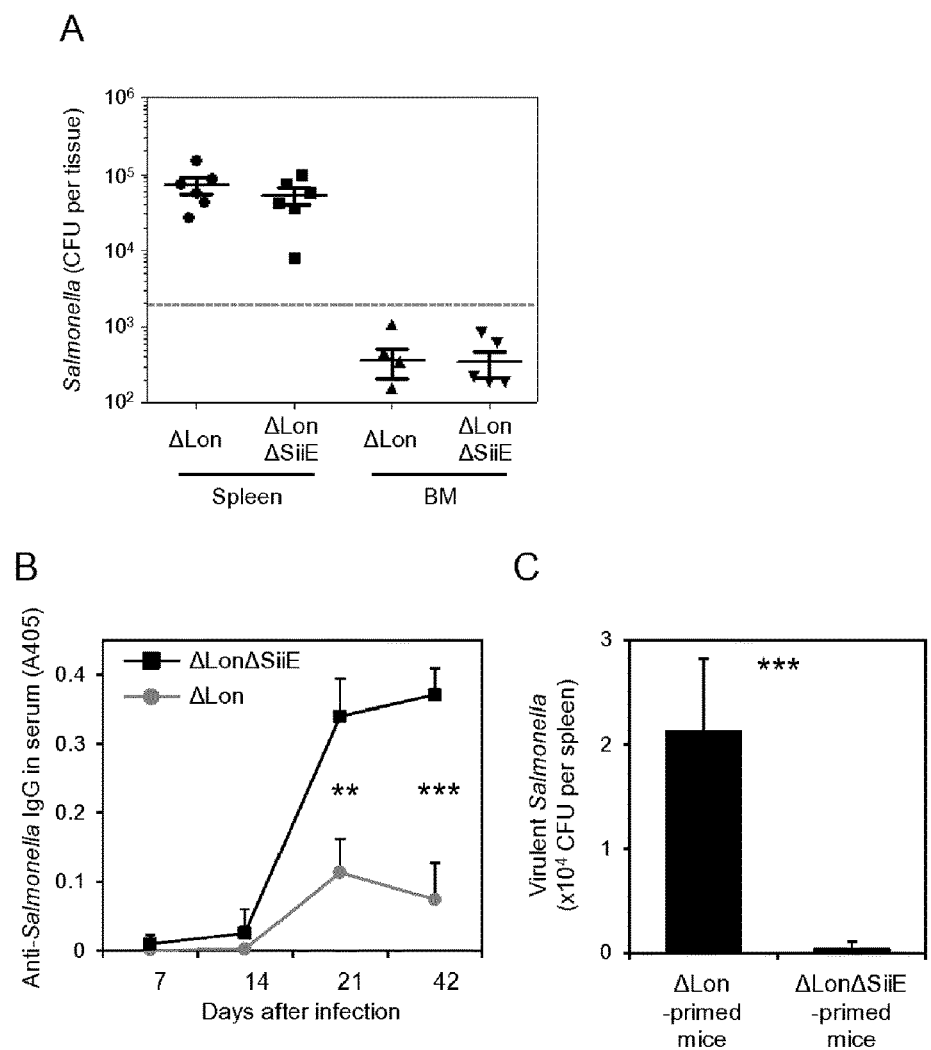
FIG. 12. Loss of SiiE enhances humoral immune response against *Salmonella*. (A) SiiE-deficient attenuated *Salmonella* normally expands in the spleen. C57BL/6 mice were infected i.p. with 104 CFU of SiiE-deficient (ΔLonΔSiiE) or SiiE-abundant (ΔLon) attenuated *Salmonella* and 4 days later were analyzed for CFU of *Salmonella* in the spleen and BM. The dotted line represents the limit of detection. n=6. (B) SiiE-deficient *Salmonella* enhances the provision of anti-*Salmonella* antibodies. C57BL/6 mice were infected i.p. with 104 CFU of attenuated *Salmonella* ΔLonΔSiiE or ΔLon, were bled on days 7, 14, 21 and 42 after infection, and were analyzed for anti-*Salmonella* IgG by ELISA. n=6. (C) Vaccination of SiiE-deficient attenuated *Salmonella* efficiently protects against a lethal dose of *Salmonella*. C57BL/6 mice which were vaccinated i.p. with 104 CFU of attenuated *Salmonella* ΔLonΔSiiE or ΔLon, were challenged i.p. with 103 CFU of wild-type *Salmonella* on day 21 after vaccination. On day 28, the number of *Salmonella* in the spleen of the infected mice was enumerated. n=5. The data are representative of at least two independent experiments. $p<0.01$, *$p<0.001$.

As shown above, SiiE inhibits the residency of BM IgG-secreting plasma cells, since culture supernatant of SiiE-deficient mutant fails to reduce plasma cell numbers. We thus expected that the SiiE mutant, because it does not impact on BM IgG-secreting plasma cells via SiiE, enhances production of antibodies against *Salmonella*. C57BL/6 mice infected with the SiiE mutant bacteria were analyzed for their titers of anti-*Salmonella* IgG. The SiiE-competent and the SiiE mutant strains of *Salmonella* did expand normally in vitro (FIG. 11A) and in vivo (FIG. 12A) and both secreted proteins and LPS into their supernatants (FIG. 11B; data not shown). The SiiE-deficient strain, however, induced significantly more anti-*Salmonella* IgG as compared to the SiiE-competent strain (FIG. 12B). To evaluate the mutant strain as a protective vaccine, mice primed by SiiE-competent or -deficient *Salmonella* were challenged with a lethal dose of wild-type *Salmonella*. On day 7 after challenge, all naive mice had died, while both groups of the vaccinated mice survived. Mice vaccinated with SiiE-deficient *Salmonella* strongly suppressed the expansion of virulent *Salmonella* in the spleen, as compared to mice vaccinated with SiiE-competent *Salmonella* (FIG. 12C). These data characterize SiiE-deficient *Salmonella* as a potential vaccine.

Example 5

CXCL12-Dependent Reduction of B Cells but not IaG-Secreting Plasma Cells by *Salmonella*

Figure 13:
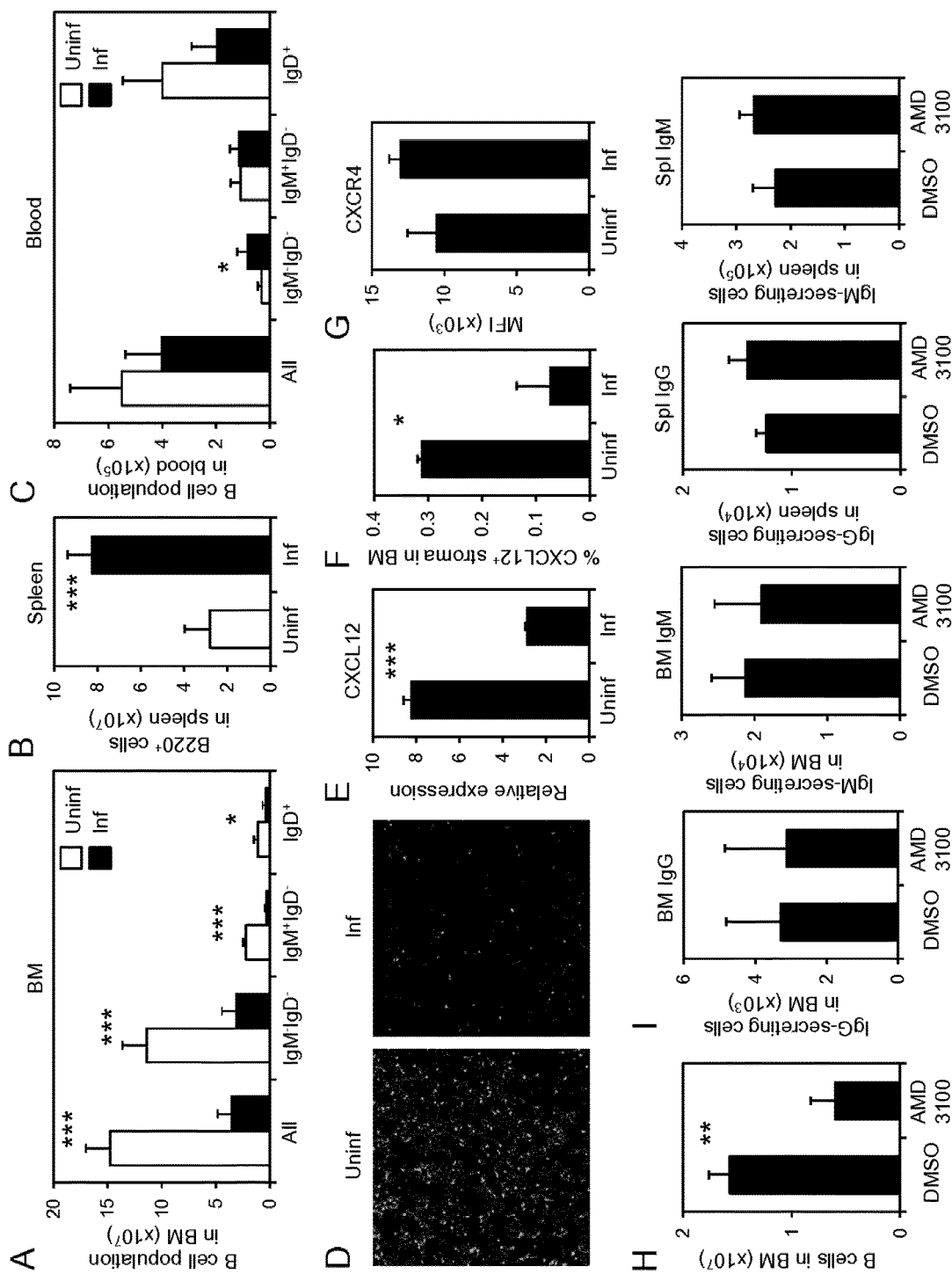
FIG. 13. *Salmonella* reduces numbers of BM IgG-secreting plasma cells in a CXCL12-independent manner. C57BL/6 mice were infected i.p. with 104 CFU of attenuated *Salmonella* and were sacrificed on day 4 post infection. Cells in the BM (A), spleen (B) and blood (C) were stained with antibodies against B220, IgM and IgD and were analyzed by flow cytometry. n=4-6. (D-F) *Salmonella* reduces the expression of CXCL12 in the BM. CXCL12/GFP knock-in mice were infected i.p. with 104 CFU of attenuated *Salmonella* and on day 4 were analyzed for the expression of CXCL12 by histology (D), quantitative RT-PCR (E, whole BM) and flow cytometry as CXCL12+ CD45-Ter119-PECAM-1-P1-cells (F). n=3. (G) *Salmonella* does not affect the expression of CXCR4 on intracellular IgG+ plasma cells. Mean fluorescent intensity (MFI) of CXCR4 on IgG+ plasma cells of infected or uninfected mice on day 4 is shown. n=3. (H and I) AMD3100 numerically reduces B cells but not IgG-secreting plasma cells in the BM. C57BL/6 mice were injected i.p. twice a day with 5 μg of AMD3100 for 4 days. B220+cells and IgG-secreting plasma cells were analyzed on day 4 by flow cytometry (H) and by ELISpot assay (I), respectively. n=5-6. The data are representative of at least two independent experiments. *$p<0.05$, $p<0.01$, *$p<0.001$.
Figure 14:
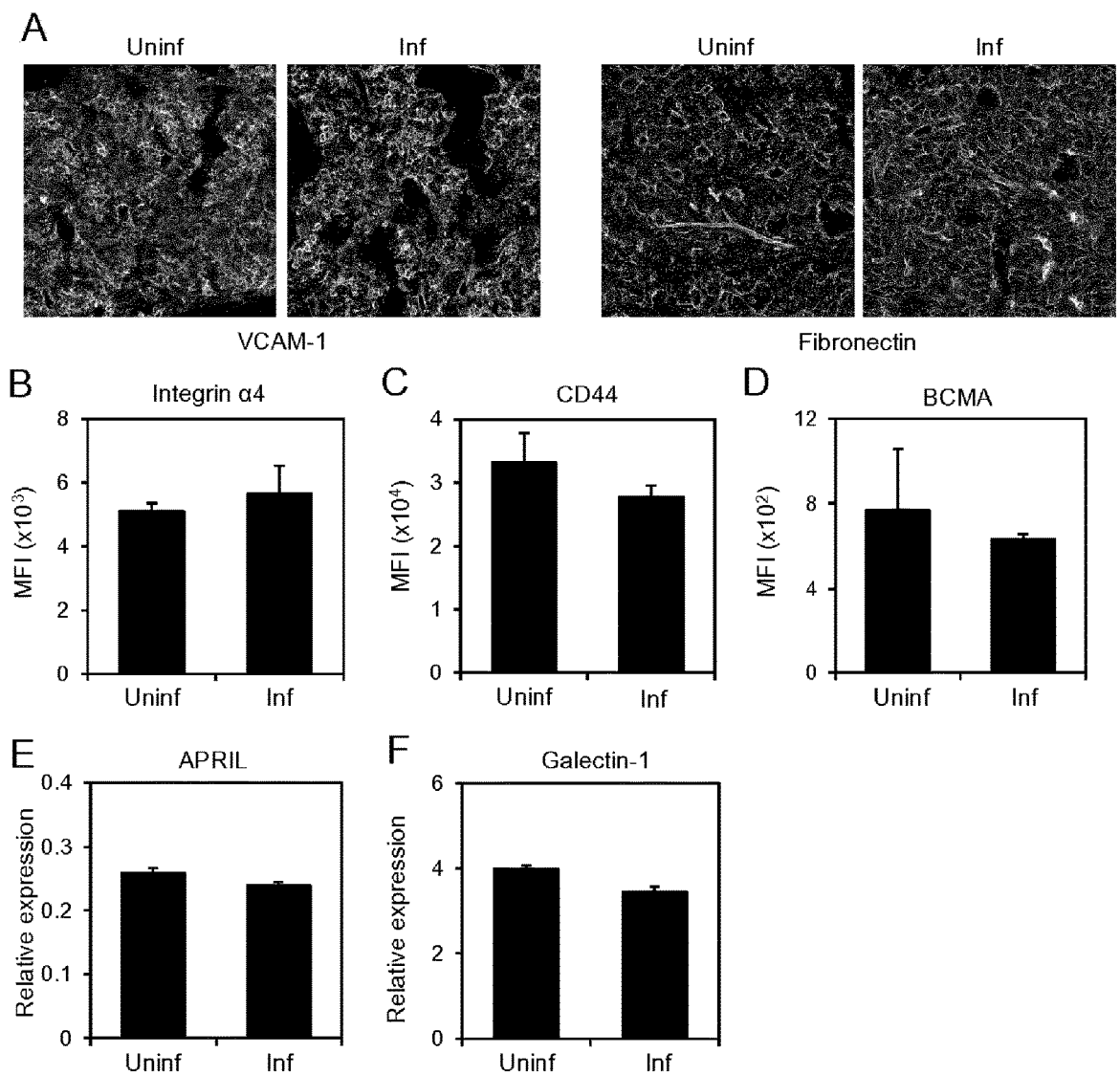
FIG. 14. *Salmonella* does not affect the expression of adhesion molecules and survival factors for plasma cells. C57BL/6 mice were infected i.p. with 104 attenuated *Salmonella* and on day 4 were analyzed for the distribution of VCAM-1 and fibronectin by histological analysis (A), for the expression of integrin a4, CD44 and BCMA on BM intracellular IgG+ plasma cells by flow cytometry (B-D), and for the expression of APRIL and Galectin-1 in the whole BM by quantitative RT-PCR (E and F). n=3. The data are representative of two independent experiments.

Bacterial infection affects the innate and the adaptive immune system. *Salmonella* reduced numbers of B cells in the BM and increased numbers of B cells in the spleen on day 4 after infection (FIGS. 13A and 13B). In the blood, although the total B cell numbers were unaffected, CD43+ IgM-IgD-B cells were significantly increased numerically (FIG. 13C; data not shown). Since numbers of CD43+IgM-IgD-B cell precursors in the BM were dramatically decreased (FIG. 13A), the blood CD43+IgM-IgD-B cells had most likely egressed from the BM. Numbers of IgG-secreting plasma cells were not increased in the spleen (FIG. 2A) and blood (data not shown) after infection with *Salmonella*. Since BM B cell precursors are retained by CXCL12 and VCAM-1/fibronectin (Miyake et al., 1991; Nagasawa et al., 1996; Kawano et al., 2017), we examined the expression of CXCL12 and VCAM-1/fibronectin and their receptors. While the expression of VCAM-1/fibronectin on stromal cells and integrin a4, a receptor of VCAM-1/fibronectin, on IgG+ plasma cells was unaffected (Figures S8A and S8B), the expression of CXCL12 was greatly impaired as shown by histological analysis (FIG. 6D), quantitative RT-PCR (FIG. 13E) and flow cytometry (FIG. 13F). The expression of CXCR4, a receptor of CXCL12, on BM IgG+ plasma cells was not altered by infection with *Salmonella* (FIG. 13G). To determine whether loss of CXCL12 by *Salmonella* affects the reduction of IgG-secreting plasma cell numbers in the BM, we examined the effect of CXCL12/CXCR4 antagonists in the persistence of BM IgG-secreting plasma cells. On day 4 after the first injection of the antagonist, numbers of IgG-secreting plasma cells in the BM were not affected, while B cell numbers in the BM were reduced (FIGS. 13H and 13I). *Salmonella* did not affect other molecules involved in the adhesion and survival of BM plasma cells; CD44, BCMA, APRIL and Galectin-1 (FIGS. 14C-14F). We conclude that reduced numbers of IgG-secreting plasma cells were caused by SiiE from *Salmonella* but not by the downregulation of CXCL12.

Example 15

Figure 15:
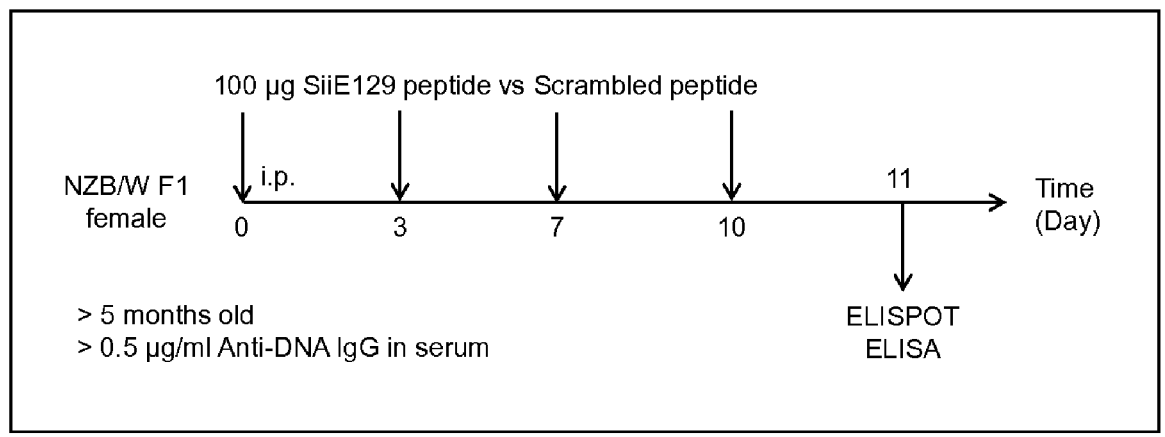
FIG. 15. SiiE129 peptide reduce numbers of DNA-specific IgG-secreting plasma cells in the bone marrow. Forty amino acid-peptide from the N terminus of SiiE protein reduces numbers of anti-DNA IgG-secreting plasma cells in the BM. NZB/VV F1 female mice (5-6 months old) received i.p. 100 μg peptide coding SiiE amino acid 129-168 on days 0, 3, 7 and 10 and on day 11 were analyzed for anti-DNA IgG-secreting cells in the BM by ELISpot assay. n=5-6. The data are representative of two independent experiments.
Figure 15:
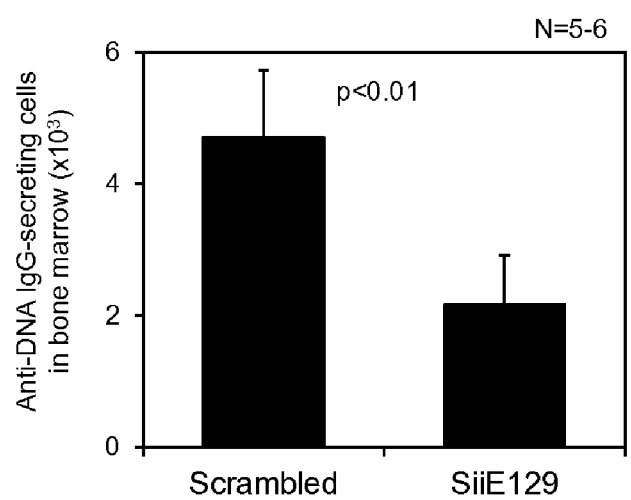

SiiE129 Peptide Reduce Numbers of DNA-Specific IaG-Secreting Plasma Cells in the Bone Marrow in a Murine Model of Systemic lupus Erythematosus NZB/VV F1 female mice (5-6 months old) received i.p. 100 μg peptide coding SiiE amino acid 129-168 on days 0, 3, 7 and 10 and on day 11 were analyzed for anti-DNA IgG-secreting cells in the BM by ELISpot assay. The data show that SiiE 129-168 reduces the number of Anti-DNA IgG-secreting cells in bone marrow (FIG. 15).

Discussion

We here show that *Salmonella* specifically reduces numbers of IgG-secreting plasma cells in the BM, which are a main source of serum IgG, in an SiiE-dependent and CXCL12-independent manner. Since no *Salmonella* could be detected in the BM and the reduction was also induced by culture supernatant of *Salmonella*, we conclude that a secreted component of *Salmonella* is responsible. We have identified the *Salmonella* protein SiiE as the responsible component. A peptide of SiiE, which has high homology to murine laminin 61, was able to reduce numbers of BM IgG-secreting plasma cells. Histological analyses of the BM revealed that IgG- but not IgM-secreting plasma cells bind to laminin 61. Thus, laminin 61+CXCL12+ stromal cells are an integral part of the survival niches for IgG-secreting plasma cells in the BM, a lesson learnt from *Salmonella*.

We had shown earlier that BM IgG+ plasma cells reside in CXCL12+ stromal niches (Tokoyoda et al., 2004). Although the character of IgM-secreting plasma cells remains controversial, they reside in the BM and are the main source of natural IgM in serum (Reynolds et al., 2015). Reynolds et al. suggested that IgM- and IgG-secreting plasma cells localize in distinct niches, because fewer IgM+ plasma cells are in contact with eosinophils in comparison to IgG+ plasma cells. Here we identify one essential difference between survival niches for IgM- and IgG-secreting plasma cells: the presence of laminin 61. The receptor of BM IgG-secreting plasma cells, as well as the intracellular signaling events, remain enigmatic, although more BM IgM-Blimp-1+ plasma cells, which include IgG-secreting plasma cells, express integrin a2 than BM IgM+Blimp-1+ and splenic Blimp-1 + plasma cells.

We posed the question as to how the plasma cells disappeared, e.g. by egress or death. No egress of IgG-secreting plasma cells into the spleen and blood could be detected on day 4 after intraperitoneal infection. Slocombe et al. showed that on days 8 and 16 after intravenous infection with 106 CFU of attenuated *Salmonella*, BM Ig+ plasma cells migrated into the spleen and then failed to return to the BM, perhaps because of the reduced expression of CXCL12 in the BM (Slocombe et al., 2013). The longterm reduction until day 16 suggests that the plasma cells were detached from their survival niches by the *Salmonella*-specific protein SiiE and died by lack of survival factors.

*Salmonella* affects the expression of CXCL12 but not fibronectin, VCAM-1 and APRIL. CXCL12 is required for the formation of long-lived memory plasma cells in the BM, because CXCR4-deficient fetal liver cells fail to generate the plasma cells (Hargreaves et al., 2001). However, it was controversial when CXCL12 is required during the formation; i.e. migration and/or maintenance. Hauser et al. showed that the migratory capacity of newly generated plasma cells is lost between day 8 and 12 after boost, suggesting that CXCL12 is required for the migration of plasma cells into their survival niches but not for their maintenance (Hauser et al., 2002). We here show that CXCR4 antagonist can inhibit the retention of B cells but not IgG-secreting plasma cells. Our data directly support the hypothesis that CXCL12 is not required for the retention and maintenance of IgG-secreting plasma cells in the BM.

Our data suggest that SiiE inhibits the interaction of IgG-secreting plasma cells with laminin β1 in the BM. *Salmonella* thus modulates humoral immunity by reducing numbers of IgG-secreting plasma cells in the BM. Laminin β1 is also expressed on mucosal epithelia. In mice and cattle, the loss of SiiE attenuated the virulence of natural oral infection with *Salmonella*, but not of intraperitoneal infection with *Salmonella* (Morgan et al., 2004; Kiss et al., 2007). Orally-infected *Salmonella* secretes SiiE and invades into the gut, likely blocking the interaction of laminin β1 and its receptors on epithelia. The ability to persist in the gut may be utilized as a side effect to replace BM IgG-secreting plasma cells. The gain of SiiE in *Salmonella* may provide advantage for the residence in animal and human hosts.

*Salmonella* specifically reduced all kinds of IgG-secreting plasma cells in the BM on day 4 after infection. In mice previously infected with *Salmonella*, newly invaded *Salmonella* can reduce long-lived anti-*Salmonella* IgG-secreting plasma cells which the main source of anti-*Salmonella* IgG in circulation. The depletion of humoral immune memory enables the new *Salmonella* to spread in the host. Infection with *Salmonella* induces humoral immune reaction (FIG. 5B; MacLennan, 2014; Di Niro et al., 2015). However, it remained unknown whether *Salmonella* affects humoral immune memory. We here show that *Salmonella* induces immune reaction and impairs immune memory in an SiiE-dependent manner. These data suggest that *Salmonella* escapes from humoral immunity, depleting memory plasma cells and also inhibiting the generation of memory plasma cells.

Infection with *Salmonella* enterica serovar Typhi, which is restricted to humans and causes severe and often fatal typhoid fever, can be prevented by vaccination with attenuated strains, e.g. Ty21a (Anwar et al., 2014). In contrast, vaccination against *Salmonella* enterica serovar Typhimurium, which causes severe food poisoning in humans, cattle, swine, sheep, horses, rodents and galliformes is not yet available. Diseases caused by these invasive nontyphoidal *Salmonella* (iNTS), including *Salmonella* enterica serovar Typhimurium, have been neglected, although the fatality rate at 20-25% is higher than that by infection with *Salmonella* enterica serovar Typhi (MacLennan et al., 2014). The SiiE gene in *Salmonella* enterica serovar Typhi has been reported as two distinct ORFs (9,852 bp and 6,771 bp, Typhimurium has 16,680 bp), suggesting that it is a pseudogene (Main-Hester et al., 2008). Furthermore, siiE gene in *Salmonella* enterica serovar Typhi has a mutation (148 A>T) within the sequence with closed homology to laminin β1. A lack of SiiE or non-functional SiiE in *Salmonella* enterica serovar Typhi may be a reason why potent vaccines against *Salmonella* Typhi are available. We show here that SiiE-deficient mutant of *Salmonella* enterica serovar Typhimurium can induce efficient immune responses, as compared to SiiE-competent *Salmonella*. To establish vaccines against iNTS, including *Salmonella* enterica serovar Typhimurium, we propose SiiE-deficient mutant attenuated *Salmonella* as a novel vaccine.

SiiE peptide homologous to laminin β1 significantly reduced numbers of IgG-secreting plasma cells in the BM. This property could be exploited for the treatment of autoimmune diseases and multiple myeloma. Autoimmune diseases with a substantial contribution of pathogenic IgG autoantibodies, like systemic lupus erythematosous, can be refractory to conventional treatment, because BM plasma cells secreting these autoantibodies are protected in their BM niches (Hoyer et al., 2004; Hiepe et al., 2011; Cheng et al., 2013). The SiiE-derived laminin β1 homologue is a candidate for depletion of refractory autoantibody-secreting BM plasma cells. Multiple myeloma is caused by redundant titers of antibodies generated from plasma cell myeloma in the BM. It has been already reported that myeloma cell lines preferentially contact laminin in vitro (Kibler et al., 1998; Vande Broek et al., 2001), suggesting that targeting of adhesion molecules including laminin should be considered as novel therapy (Neri and Bahlis, 2012). The depletion of BM plasma cell myeloma may directly ameliorate disease.

REFERENCES

Andrews-Polymenis, H. L., Bäumler, A. J., McCormick, B. A., and Fang, F. C. (2010). Taming the elephant: *Salmonella* biology, pathogenesis, and prevention. Infect. Immun. 78, 2356-2369.

Anthony, B., and Link, D. C. (2014). Regulation of hematopoietic stem cells by bone marrow stromal cells. Trends Immunol. 35, 32-37.

Anwar, E., Goldberg, E., Fraser, A., Acosta, C. J., Paul, M., and Leibovici, L. (2014). Vaccines for preventing typhoid fever. Cochrane Database Syst. Rev. 2, CD001261.

Ara, T., Tokoyoda, K., Sugiyama, T., Egawa, T., Kawabata, K., and Nagasawa, T. (2003). Long-term hematopoietic stem cells require stromal cell-derived factor-1 for colonizing bone marrow during ontogeny. Immunity 19, 257-267.

Barlag, B., and Hensel, M. (2015). The giant adhesin SiiE of *Salmonella* enterica. Molecules 20, 1134-1150.

Belkin, A. M., and Stepp, M. A. (2000). Integrins as receptors for laminins. Microsc. Res. Tech. 51, 280-301.

Bueno, S. M., González, P. A., Carreño, L. J., Tobar, J. A., Mora, G. C., Pereda, C. J., Salazar-Onfray, F., and Kalergis, A. M. (2008). The capacity of *Salmonella* to survive inside dendritic cells and prevent antigen presentation to T cells is host specific. Immunology 124, 522-533.

Cheng, Q., Mumtaz, I. M., Khodadadi, L., Radbruch, A., Hoyer, B. F., and Hiepe, F. (2013). Autoantibodies from long-lived "memory" plasma cells of NZB/W mice drive immune complex nephritis. Ann. Rheum. Dis. 72, 2011-2017.

Chu, V. T., Fröhlich, A., Steinhauser, G., Scheel, T., Roch, T., Fillatreau, S., Lee, J. J., Löhning, M., and Berek, C. (2011). Eosinophils are required for the maintenance of plasma cells in the bone marrow. Nat. Immunol. 12, 151-159.

Clark, B. R., and Keating, A. (1995). Biology of bone marrow stroma. Ann. N. Y. Acad. Sci. 770, 70-78.

Datsenko, K. A., and Wanner, B.L. (2000). One-step inactivation of chromosomal genes in *Escherichia coli* K-12 using PCR products. Proc. Natl. Acad. Sci. USA. 97, 6640-6645.

Di Niro, R., Lee, S. J., Vander Heiden, J. A., Elsner, R. A., Trivedi, N., Bannock, J. M., Gupta, N. T., Kleinstein, S. H., Vigneault, F., Gilbert, T. J., Meffre, E., McSorley, S. J., and Shlomchik, M. J. (2015). *Salmonella* Infection Drives Promiscuous B Cell Activation Followed by Extrafollicular Affinity Maturation. Immunity 43, 120-131.

Dougan, G., and Baker, S. (2014). *Salmonella* enterica serovar Typhi and the pathogenesis of typhoid fever. Annu. Rev. Microbiol. 68, 317-336.

Gerlach, R. G., Jäckel, D., Stecher, B., Wagner, C., Lupas, A., Hardt, W. D., and Hensel, M. (2007). *Salmonella* Pathogenicity Island 4 encodes a giant non-fimbrial adhesin and the cognate type 1 secretion system. Cell. Microbiol. 9, 1834-1850.

Gu, Y., Sorokin, L., Durbeej, M., Hjalt, T., Jönsson, J. I., and Ekblom, M. (1999). Characterization of bone marrow laminins and identification of alpha5-containing laminins as adhesive proteins for multipotent hematopoietic FDCP-Mix cells. Blood 93, 2533-2542.

Gulig, P. A., and Curtiss III, R. (1987). Plasmid-associated virulence of *Salmonella* typhimurium. Infect. Immun. 55, 2891-2901.

Hanazawa, A., Hayashizaki, K., Shinoda, K., Yagita, H., Okumura, K., Lohning, M., Hara, T., Tani-ichi, S., Ikuta, K., Eckes, B., Radbruch, A., Tokoyoda, K., Nakayama, T. (2013). CD49b-dependent establishment of T helper cell memory. Immunol. Cell Biol. 91, 524-531.

Hargreaves, D. C., Hyman, P. L., Lu, T. T., Ngo, V. N., Bidgol, A., Suzuki, G., Zou, Y.-R. R., Littman, D. R., and Cyster, J. G. (2001). A coordinated change in chemokine responsiveness guides plasma cell movements. J. Exp. Med. 194, 45-56.

Hauser, A. E., Debes, G. F., Arce, S., Cassese, G., Hamann, A., Radbruch, A., and Manz, R. A. (2002). Chemotactic responsiveness toward ligands for CXCR3 and CXCR4 is regulated on plasma blasts during the time course of a memory immune response. J. Immunol. 169, 1277-1282.

Hiepe, F., Darner, T., Hauser, A. E., Hoyer, B. F., Mei, H., and Radbruch, A. (2011). Long-lived autoreactive plasma cells drive persistent autoimmune inflammation. Nat. Rev. Rheumatol. 7, 170-178.

Hoyer, B. F., Moser, K., Hauser, A. E., Peddinghaus, A., Voigt, C., Eilat, D., Radbruch, A., Hiepe, F., and Manz, R. A. (2004). Short-lived plasmablasts and long-lived plasma cells contribute to chronic humoral autoimmunity in NZB/W mice. J. Exp. Med. 199, 1577-1584.

Kamata, T., Nogaki, F., Fagarasan, S., Sakiyama, T., Kobayashi, I., Miyawaki, S., Ikuta, K., Muso, E., Yoshida, H., Sasayama, S., and Honjo, T. (2000). Increased frequency of surface IgA-positive plasma cells in the intestinal lamina propria and decreased IgA excretion in hyper IgA (HIGA) mice, a murine model of IgA nephropathy with hyperserum IgA. J. Immunol. 165, 1387-1394.

Kallies, A., Hasbold, J., Tarlinton, D. M., Dietrich, W., Corcoran, L. M., Hodgkin, P. D., and Nutt, S. L. (2004). Plasma cell ontogeny defined by quantitative changes in blimp-1 expression. J. Exp. Med. 200, 967-977.

Kawamoto, T., and Kawamoto, K. (2014). Preparation of thin frozen sections from nonfixed and undecalcified hard tissues using Kawamoto's film method (2012). Methods Mol. Biol. 1130, 149-164.

Kawano, Y., Petkau, G., Wolf, I., Tornack, J., and Melchers, F. (2017). IL-7 and immobilized Kit-ligand stimulate serum- and stromal cell-free cultures of precursor B-cell lines and clones. Eur. J. Immunol. 47, 206-212.

Kibler, C., Schermutzki, F., Waller, H. D., Timpl, R., Müller, C. A., and Klein, G. (1998). Adhesive interactions of human multiple myeloma cell lines with different extracellular matrix molecules. Cell Adhes. Commun. 5, 307-323.

Kiss, T., Morgan, E., and Nagy, G. (2007). Contribution of SPI-4 genes to the virulence of *Salmonella* enterica. FEMS Microbiol. Lett. 275, 153-159.

Kodama, C., Eguchi, M., Sekiya, Y., Yamamoto, T., Kikuchi, Y., and Matsui, H. (2005). Evaluation of the Lon-deficient *Salmonella* strain as an oral vaccine candidate. Microbiol. Immunol. 49, 1035-1045.

MacLennan, C. A. (2014). Antibodies and protection against invasive salmonella disease. Front. Immunol. 5, 635.

MacLennan, C. A., Martin, L. B., and Micoli, F. (2014). Vaccines against invasive *Salmonella* disease: current status and future directions. Hum. Vaccin. Immunother. 10, 1478-1493.

Main-Hester, K. L., Colpitts, K. M., Thomas, G. A., Fang, F. C., and Libby, S. J. (2008). Coordinate regulation of *Salmonella* pathogenicity island 1 (SPI1) and SPI4 in *Salmonella* enterica serovar typhimurium. Infect. Immun. 76, 1024-1035.

Miyake, K., Weissman, I. L., Greenberger, J. S., and Kincade, P. W. (1991). Evidence for a role of the integrin VLA-4 in lympho-hemopoiesis. J. Exp. Med. 173, 599-607.

Morgan, E., Campbell, J. D., Rowe, S. C., Bispham, J., Stevens, M. P., Bowen, A. J., Barrow, P. A., Maskell, D. J., and Wallis, T. S. (2004). Identification of host-specific colonization factors of *Salmonella* enterica serovar Typhimurium. Mol. Microbiol. 54, 994-1010.

Nagasawa, T., Hirota, S., Tachibana, K., Takakura, N., Nishikawa, S., Kitamura, Y., Yoshida, N., Kikutani, H., and Kishimoto, T. (1996). Defects of B-cell lymphopoiesis and bone-marrow myelopoiesis in mice lacking the CXC chemokine PBSF/SDF-1. Nature 382, 635-638.

Nagasawa, T. (2006). Microenvironmental niches in the bone marrow required for B-cell development. Nat. Rev. Immunol. 6, 107-116.

Neri, P., and Bahlis, N. J. (2012). Targeting of adhesion molecules as a therapeutic strategy in multiple myeloma. Curr. Cancer Drug Targets 12, 776-796.

O'Connor, B. P., Raman, V. S., Erickson, L. D., Cook, W. J., Weaver, L. K., Ahonen, C., Lin, L.-L., Mantchev, G. T., Bram, R. J., and Noelle, R. J. (2004). BCMA is essential for the survival of long-lived bone marrow plasma cells. J. Exp. Med. 199, 91-98.

Radbruch, A., Muehlinghaus, G., Luger, E. O., Inamine, A., Smith, K. G. C., Darner, T., and Hiepe, F. (2006). Competence and competition: the challenge of becoming a long-lived plasma cell. Nat. Rev. Immunol. 6, 741-750.

Reynolds, A. E., Kuraoka, M., and Kelsoe, G. (2015). Natural IgM is produced by CD5-plasma cells that occupy a distinct survival niche in bone marrow. J. Immunol. 194, 231-242.

Santos, R. L., Zhang, S., Tsolis, R. M., Kingsley, R. A., Adams, L. G., and Baumler, A. J. (2001). Animal models of *Salmonella* infections: enteritis versus typhoid fever. Microbes Infect. 3, 1335-1344.

Slocombe, T., Brown, S., Miles, K., Gray, M., Barr, T. A., and Gray, D. (2013). Plasma cell homeostasis: the effects of chronic antigen stimulation and inflammation. J. Immunol. 191, 3128-3138.

Takaya, A., Tomoyasu, T., Tokumitsu, A., Morioka, M., and Yamamoto, T. (2002). The ATP-dependent Lon protease of *Salmonella* enterica serovar Typhimurium regulates invasion and expression of genes carried on *Salmonella* pathogenicity island 1. J. Bacteriol. 184, 224-232.

Tam, J. W., Kullas, A. L., Mena, P., Bliska, J. B., and Van der Velden, A. W. M. (2014). CD11b+Ly6ChiLy6G-immature myeloid cells recruited in response to *Salmonella* enterica serovar typhimurium infection exhibit protective and immunosuppressive properties. Infect. Immun. 82, 2606-2614.

Tokoyoda, K., Egawa, T., Sugiyama, T., Choi, B. II, and Nagasawa, T. (2004). Cellular niches controlling B lymphocyte behavior within bone marrow during development. Immunity 20, 707-718.

Tokoyoda, K., Zehentmeier, S., Hegazy, A.N., Albrecht, I., Grün, J. R., Lohning, M., Radbruch, A. (2009). Professional memory CD4+ T lymphocytes preferentially reside and rest in the bone marrow. Immunity 30, 721-730.

Tokoyoda, K., Hauser, A. E., Nakayama, T., and Radbruch, A. (2010). Organization of immunological memory by bone marrow stroma. Nat. Rev. Immunol. 10, 193-200.

Tomoyasu, T., Mogk, A., Langen, H., Goloubinoff, P., and Bukau, B. (2001). Genetic dissection of the roles of chaperones and proteases in protein folding and degradation in the *Escherichia coli* cytosol. Mol. Microbiol. 40, 397-413.

Tomoyasu, T., Takaya, A., Isogai, E., and Yamamoto, T. (2003). Turnover of FlhD and FlhC, master regulator proteins for *Salmonella* flagellum biogenesis, by the ATP-dependent ClpXP protease. Mol. Microbiol. 48, 443-452.

Vande Broek, I., Vanderkerken, K., De Greef, C., Asosingh, K., Straetmans, N., Van Camp, B., and Van Riet, I. (2001). Laminin-1-induced migration of multiple myeloma cells involves the high-affinity 67 kD laminin receptor. Br. J. Cancer 85, 1387-1395.

Wilson, A., and Trumpp, A. (2006). Bone-marrow haematopoietic-stem-cell niches. Nat. Rev. Immunol. 6, 93-106.

Winter, O., Moser, K., Mohr, E., Zotos, D., Kaminski, H., Szyska, M., Roth, K., Wong, D. M., Dame, C., Tarlinton, D. M., et al. (2010). Megakaryocytes constitute a functional component of a plasma cell niche in the bone marrow. Blood 116, 1867-1875.

Zehentmeier, S., Roth, K., Cseresnyes, Z., Sercan, Ö., Horn, K., Niesner, R. A., Chang, H. D., Radbruch, A., and Hauser, A. E. (2014). Static and dynamic components synergize to form a stable survival niche for bone marrow plasma cells. Eur. J. Immunol. 44, 2306-2317.

The invention claimed is:

1. An isolated polypeptide comprising the amino acid sequence according to SEQ ID NO 1 (EEAEKAKEAAEKALNEAFE), wherein the polypeptide is no longer than 200 amino acids.

2. The polypeptide according to claim 1, wherein the polypeptide comprises the amino acid sequence according to SEQ ID NO 2 (KEADKAKEEAEKAKEAAEKALNEAFEVQNSSKQIEEMLQN).

3. The polypeptide according to claim 1, wherein the polypeptide comprises the amino acid sequence according to SEQ ID NO 3 (SAQVEKKGNGKRRNKKEEEELKKQLDDAENAKKEADKAKEEAEKAKEAAEKALNEAFEVQNSSKQIEEMLQNFL).

4. The polypeptide according to claim 1, wherein the polypeptide comprises the amino acid sequence according to SEQ ID NO 4 (MGNKSIQKFFADQNSVIDLSSLGNAKGAKVSLSGPDMNITTPRGSVIIVNGALY SSIKGNNLAVKFKDKTITGAKILGSVDLKDIQLERIDSSLVDSAQVEKKGNGKRRNKKEEEELKKQLDDAENAKKEADKAKEEAEKAKEAAEKALNEAFEVQNSSKQIEEMLQNFL).

5. The polypeptide according to claim 1, wherein the polypeptide competes with laminin β1 interaction with long-lived plasma cells (LLPC).

6. A pharmaceutical composition for use in the treatment of a disease associated with pathogenic long-lived plasma cells comprising the polypeptide of claim 1, and a pharmaceutically accepted carrier.

7. An isolated nucleic acid molecule that encodes the polypeptide according to claim 1.

8. A cell, wherein
the cell is a *Salmonella* bacterium comprising a nucleic acid region encoding a polypeptide according to claim 1, or
the cell is genetically modified and comprises an exogenous nucleic acid region encoding a polypeptide according to claim 1, and wherein the exogenous nucleic acid region is operably linked to a promoter.

9. A pharmaceutical composition for use in the treatment of a disease associated with pathogenic long-lived plasma cells comprising a nucleic acid molecule according to claim 7 and a pharmaceutically accepted carrier.

10. A pharmaceutical composition for use in the treatment of a disease associated with pathogenic long-lived plasma cells comprising a cell according to claim 8, and a pharmaceutically accepted carrier.

11. A method of treating a disease associated with pathogenic long-lived plasma cells in a subject in need thereof, the method comprising administering to the subject the polypeptide according to claim 1.

12. The method according to claim 11, wherein the disease associated with pathogenic long-lived plasma cells is multiple myeloma.

13. The method according to claim 11, wherein the disease associated with pathogenic long-lived plasma cells is an auto-antibody-associated autoimmune disease.

14. The method according to claim 11, wherein the pathogenic long-lived plasma cells are IgG-secreting plasma cells and/or reside in the bone marrow and/or interact with laminin β1-positive stroma cells.

15. The method according to claim 13, wherein the disease associated with pathogenic long-lived plasma cells is rheumatoid arthritis or systemic lupus erythematosus.

* * * * *